United States Patent
Schweizer et al.

(10) Patent No.: US 9,222,104 B2
(45) Date of Patent: Dec. 29, 2015

(54) METHOD FOR CREATING BROAD-SPECTRUM RESISTANCE TO FUNGI IN TRANSGENIC PLANTS

(75) Inventors: Patrick Schweizer, Ballenstedt (DE); Goetz Hensel, Koethen (DE); Alexandra Gay, Odenthal (DE); Jochen Kumlehn, Postdam (DE)

(73) Assignee: The Leibniz Institute of Plant Genetics and Crop Plant Research, Gatersleben (DE)

( * ) Notice: Subject to any disclaimer, the term of this patent is extended or adjusted under 35 U.S.C. 154(b) by 516 days.

(21) Appl. No.: 12/922,454

(22) PCT Filed: Mar. 12, 2009

(86) PCT No.: PCT/EP2009/001805
§ 371 (c)(1),
(2), (4) Date: Dec. 1, 2010

(87) PCT Pub. No.: WO2009/112270
PCT Pub. Date: Sep. 17, 2009

(65) Prior Publication Data
US 2011/0067144 A1 Mar. 17, 2011

(30) Foreign Application Priority Data
Mar. 13, 2008 (DE) .......................... 10 2008 014 041

(51) Int. Cl.
C12N 15/82 (2006.01)

(52) U.S. Cl.
CPC ........ *C12N 15/8282* (2013.01); *C12N 15/8279* (2013.01)

(58) Field of Classification Search
None
See application file for complete search history.

(56) References Cited

U.S. PATENT DOCUMENTS

| 5,168,053 A | * | 12/1992 | Altman et al. | ............... 514/44 R |
| 2006/0123505 A1 | | 6/2006 | Kikuchi | |
| 2007/0044171 A1 | * | 2/2007 | Kovalic et al. | ................ 800/278 |
| 2007/0061918 A1 | | 3/2007 | Baltz et al. | |

FOREIGN PATENT DOCUMENTS

| WO | WO 00/01722 | 1/2000 |
| WO | WO 2005/019408 | 3/2005 |
| WO | WO 2006/047495 | 5/2006 |
| WO | WO 2006/097465 | 9/2006 |

OTHER PUBLICATIONS

Chen (Genetics, 167, p. 607-617, 2004).*
Semighini et al (FEMS Microbiology Letters, 279(2), p. 259-264, Jan. 2008; "Semighini").*
Fairbairn et al (Planta, 226, p. 1525-1533, 2007; "Fairbairn").*
Lin et al (Biochemical and Biophysical Research Communications, 310, p. 754-760, 2003; "Lin").*
Miki et al., Plant Physiol., 138(4), pp. 1903-1913, 2005.*
Kaur et al., The Plant cell, 18(3), pp. 545-559, 2006.*
Douchkov, et al. "A high-throughput gene-silencing system for the functional assessment of defense-related genes in barley epidermal cells," *Molecular Plant-Microbe Interactions*, vol. 18, No. 8, pp. 755-761, Aug. 1, 2005.
Paddison, et al. "A resource for large-scale RNZ-interference-based screens in mammals," *Nature*, vol. 428, No. 6981, Mar. 25, 2004, pp. 427-431.
PCT, International Search Report and Written Opinion issued in corresponding International application No. PCT/EP2009/001805, mailed on Aug. 28, 2009, 11 pages.
Schweizer, et al. "Double-stranded RNA interferes with gene function at the single-cell level in cereals," *Plant Journal*, vol. 24, No. 6, Dec. 1, 2000, pp. 895-903.
Waterhouse, et al. "Virus resistance and gene silencing in plants can be induced by simultaneous expression of sense and antisense RNA," *Proceedings of the National Academy of Sciences of USA*, vol. 95, Nov. 1, 1998, pp. 13959-13964.

* cited by examiner

*Primary Examiner* — Elizabeth McElwain
*Assistant Examiner* — Stephen Uyeno
(74) *Attorney, Agent, or Firm* — Hahn Loeser & Parks LLP

(57) ABSTRACT

The present invention relates to the creation of broad-spectrum resistance in transgenic plants by inserting inhibitory nucleic acid sequences inhibiting the expression of fungal genes.
The nucleic acid sequences of genes which are crucial to development, growth and profilation of fungi, i.e. sequences of genes with an essential function in fungi, are often conserved and/or have a high sequence identity. Regions having a particularly high sequence identity between various fungi are used in order to produce inhibitory gene constructs, e.g. on basis of antisense, siRNA, shRNA, ribozyme technology and other technologies imparting the inhibition of the expression and activation of genes. Since said methods base on the sequence-specific hybridization of the inhibitory RNA molecules with respective target sequences in certain fungal genes, the expression of all corresponding genes from various fungi is thus inhibited as well. Due to the high sequence identity of such conserved gene sections, transgenic plants are thus produced, which have broad-spectrum resistance to various fungi.

13 Claims, 17 Drawing Sheets

FIG. 1

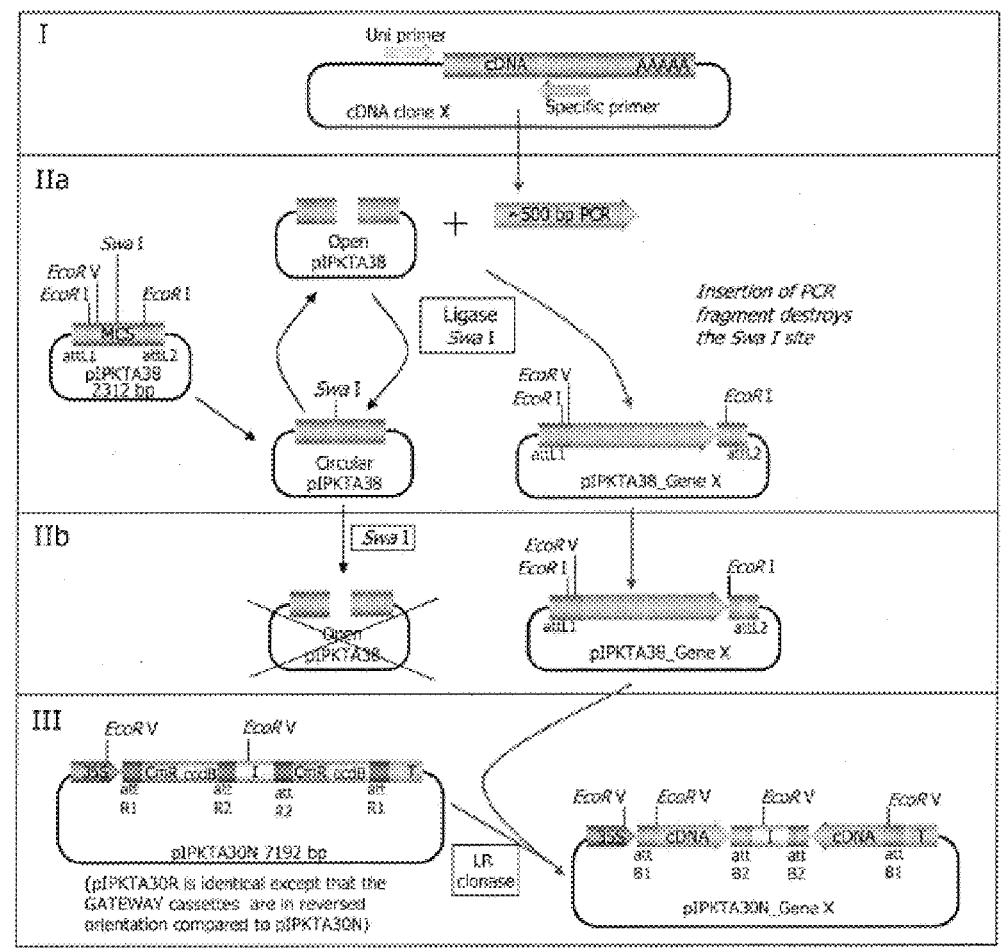

Fig. 1: Flow diagram for the high-throughput production of RNAi constructs. I, PCR amplification of cDNA fragments of fungal genes of interest; IIa, Ligation of the PCR fragments in the intermediate vector pIPKTA38 in the presence of the restriction endonuclease, Swa I, which inhibits the re-ligation of the vector; IIb, Re-cutting all re-ligated vector molecules; III, Recombination of the cloned cDNA fragments in the RNAi vector pIPKTA30 by means of LR clonase.

FIG. 2

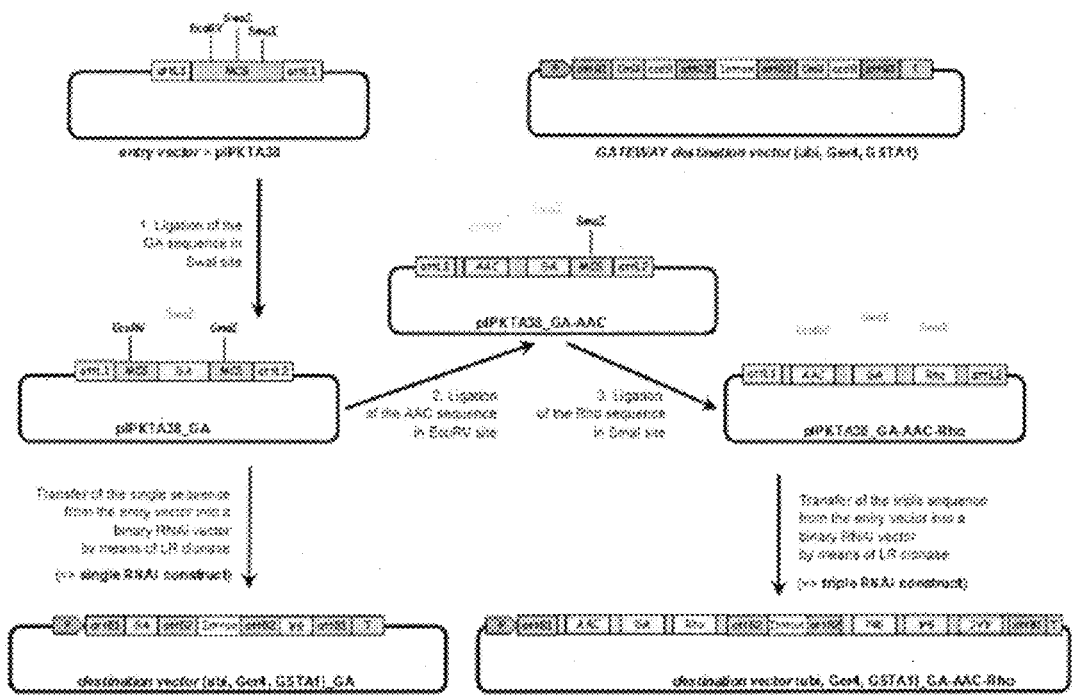

Fig. 2: Schematic representation of the synthesis pathway of simple (single) as well as combined (triple) RNAi constructs by means of the modified GATEWAY technology as to Douchkov et al. (2005) using the example of a sequence from gamma-actin (*single RNAi construct*), and a sequence combination of three components (gamma-actin, ADP/ATP carrier as well as RhoGTPase; *triple RNAi construct*). pIPKb007 (ubi), p6UGER4deltaSwaIntronRNAi (Ger4) and pIPKb010 (GSTA1) were used as binary RNAi *destination vectors*.

FIG. 3

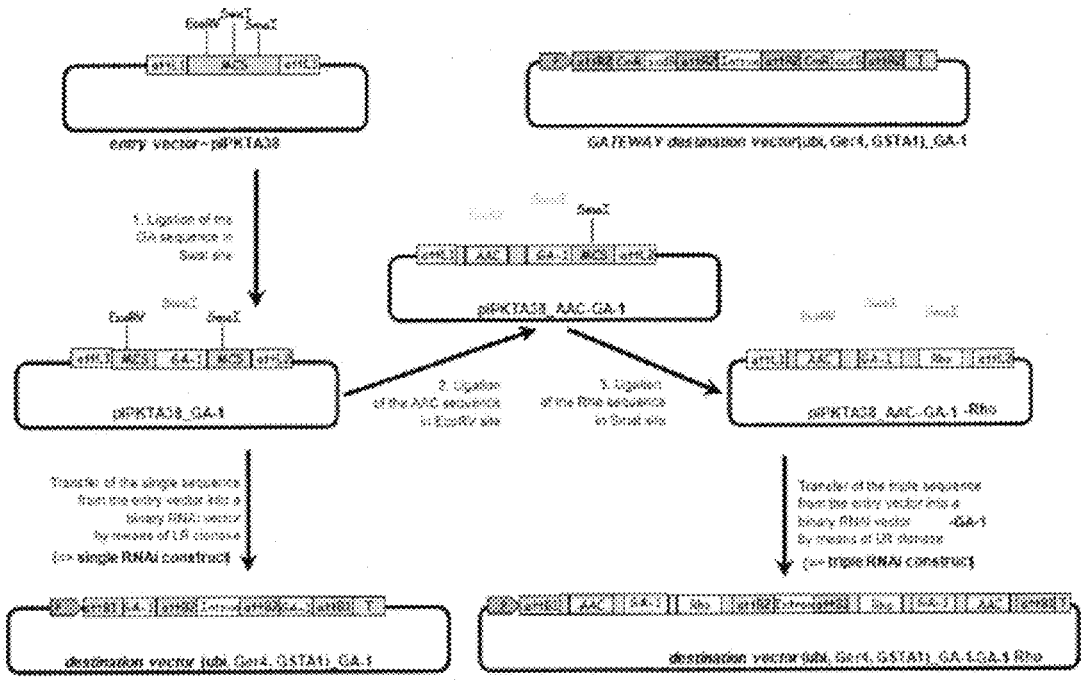

Fig. 3: Schematic representation of an alternative synthesis pathway of simple (single) as well as combined (triple) RNAi constructs by means of the modified GATEWAY technology as to Douchkov et al. (2005) using the example of a sequence from gamma-actin (*single RNAi construct*), and a sequence combination of three components (ADP/ATP carrier, gamma-actin as well as RhoGTPase; *triple RNAi construct*). pIPKb007 (ubi), p6UGER4deltaSwaIntronRNAi (Ger4) and pIPKb010 (GSTA1) were used as binary RNAi *destination vectors*.

Figure 4:
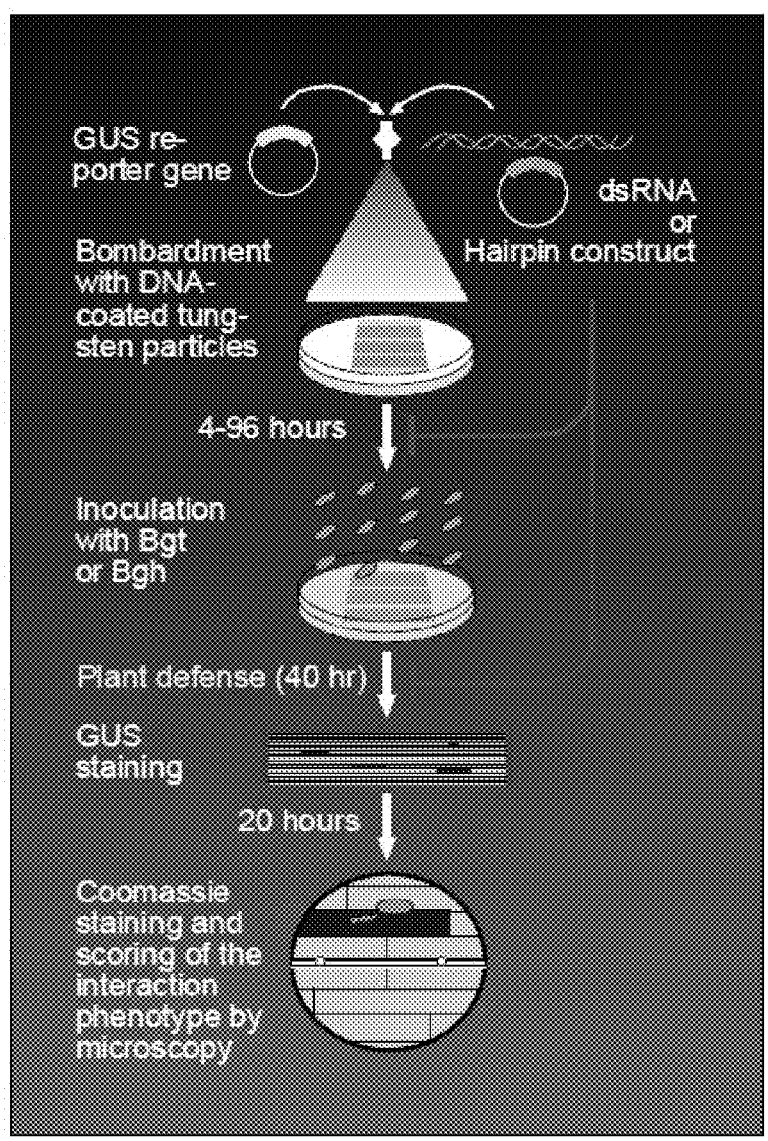

Fig.4: Flow diagram of the HIGS system. The RNAi constructs are directed against fungal transcripts.

Figure 5:
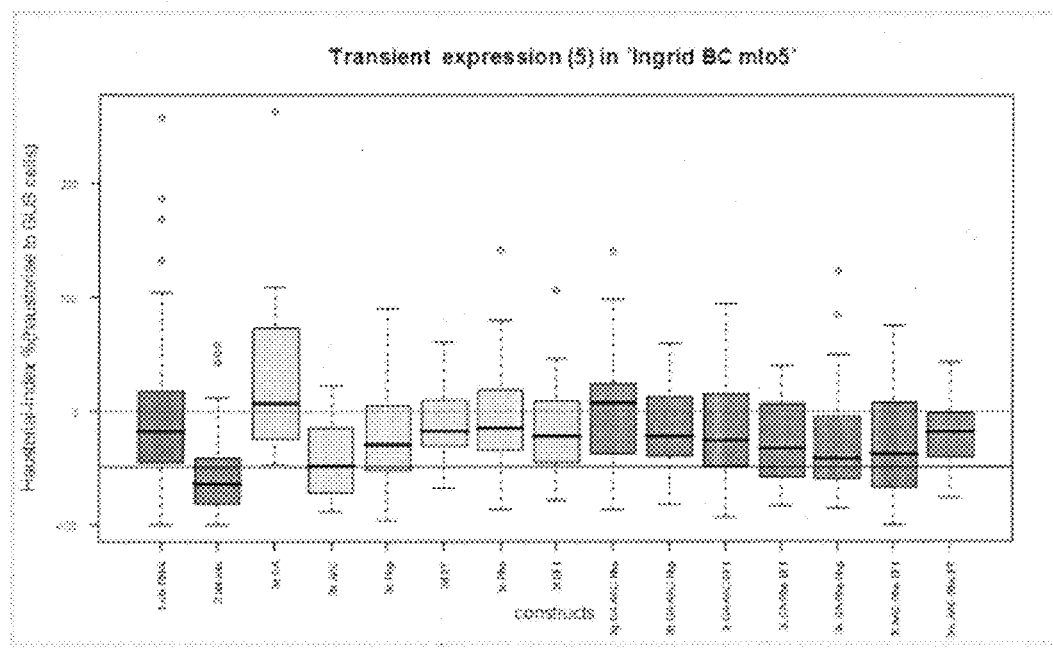

Fig. 5: Transient transformation experiments with barley leaves of the sort Ingrid BC mlo5 (*Hordeum vulgare*). Spores of the phytopathogenic *Blumeria graminis* f. sp. *hordei* (barley powdery mildrew) were used as inoculum. In said system, *single* and *triple target* RNAi constructs were tested in combination with the vector pIPKb007.

Figure 6:
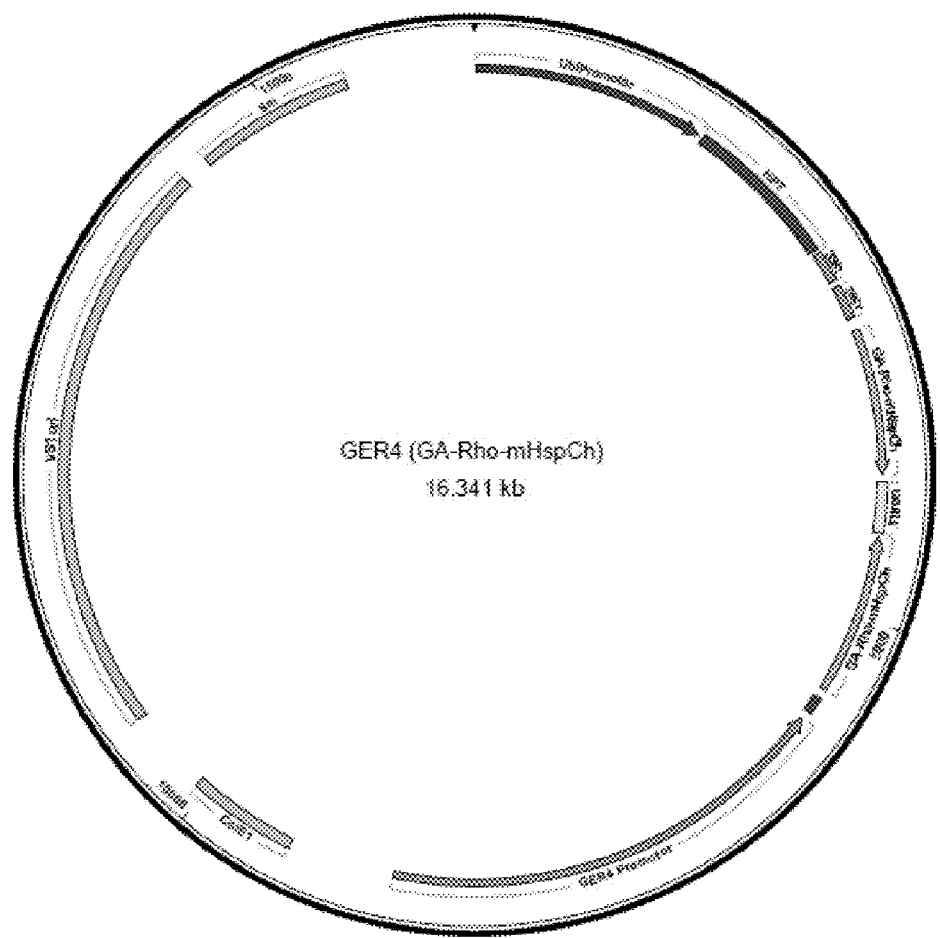

Fig. 6: Schematic structure of a construct having the GER4 promotor as well as an insert of a triple sequence combination (e.g. gamma-actin, RhoGTPase and mitochondrial heat shock protein 70 chaperone):

Fig. 6B

Components of the construct in Fig. 6:
- LB *(16041-16063 bp)*
- ori Col E1 *(9374-10071 bp)*
- ori p VS1 *(10620-14325 bp)*
- Sm *(14509-15319 bp)*
- Ubi promotor *(10-1517 bp)*
- HPT *(1544-2569 bp)*
- 35ST *(2592-2795 bp)*
- 35ST *(2835-3058 bp)*
- Inverted repeat 1: gamma-actin – RhoGTPase – mitochondrial heat shock protein 70 chaperone *(3140-4083 bp)*
- Intron *(5579-5692 bp)*
- Inverted repeat 2: gamma-actin – RhoGTPase – mitochondrial heat shock protein 70 chaperone *(4478-5516 bp)*
- GER4 promotor *(5742-8694 bp)*

Figure 7A:

Fig. 7: Schematic structure of a construct having the p6UubiRNAi promotor as well as an insert of a triple sequence combination (e.g. gamma-actin, RhoGTPase and mitochondrial heat shock protein 70 chaperone):

FIG. 7B

Components of the construct in Fig. 7:
- RB *(7283-7306 bp)*
- ori T Col E1 *(7841-8538 bp)*
- ori p VS1 *(9087-14792 bp)*
- Sm *(12976-13986 bp)*
- Ubi promotor *(10-1517 bp)*
- HPT *(1544-2569)*
- 35ST *(2592-2795 bp)*
- 35ST *(2835-3058 bp)*
- Inverted repeat 1: gamma-actin – RhoGTPase – mitochondrial heat shock protein 70 chaperone *(3141-4135 bp)*
- Intron *(4178-4508 bp)*
- Inverted repeat 2 : gamma-actin – RhoGTPase – mitochondrial heat shock protein 70 chaperone *(4554-5548 bp)*
- Ubi promotor *(5688-7194 bp)*

Figure 8A:
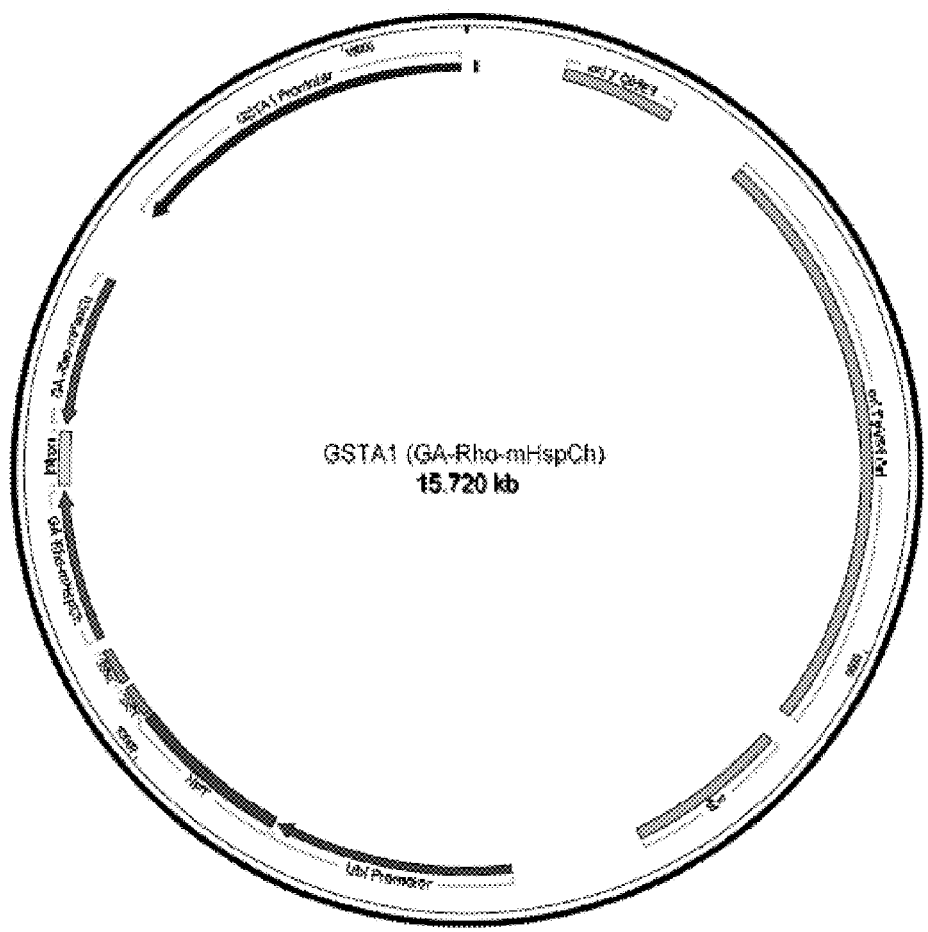

Fig. 8: Schematic structure of a construct having the GSTA1 promotor and an insert of a triple sequence combination (e.g. gamma-actin, RhoGTPase and mitochondrial heat shock protein 70 chaperone):

FIG. 8B

Components of the construct in Fig. 8:
- RB *(48-71 bp)*
- ori T Col E1 *(606-1303 bp)*
- ori T pVS1 *(1852-5557 bp)*
- Sm *(5741-6731 bp)*
- Ubi promotor *(7583-9090 bp)*
- HPT *(9117-10142 bp)*
- 35ST *(1048-10631 bp)*
- 35ST *(10165-10368 bp)*
- Inverted repeat 1: gamma-actin – RhoGTPase – mitochondrial heat shock protein 70 chaperone *(10714-11656 bp)*
- Intron *(11699-12029 bp)*
- Inverted repeat 2: gamma-actin – RhoGTPase – mitochondrial heat shock protein 70 chaperone *(12075-13017 bp)*
- GSTA1 promotor *(13483-15680 bp)*

Figure 9A:
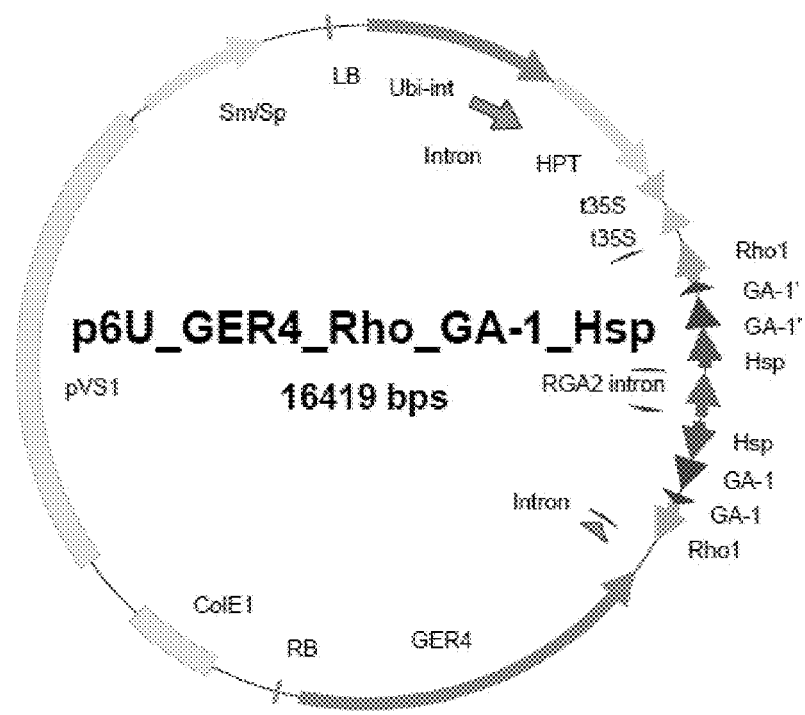

Fig. 9: Schematic structure of the construct No. 35 (p6U_GER4_Rho_GA-1_Hsp) having the GER4 promotor and an insert of a triple sequence combination (e.g. RhoGTPase, gamma-actin and mitochondrial heat shock protein 70 chaperone):

FIG. 9B

Components of the construct in Fig. 9:
- LB *(16118-16141 bp)*
- ori ColE1 *(9452-10149 bp)*
- ori pVS1 *(10698-14403 bp)*
- Sm/Sp *(14587-15597 bp)*
- Ubi promotor *(10-1517 bp)*
- HPT *(1544-2569 bp)*
- 35ST *(2594-2795 bp)*
- 35ST *(2840-3030 bp)*
- Inverted repeat 1: RhoGTPase – gamma-actin – mitochondrial heat shock protein 70 chaperone *(3141-4122 bp)*
- Intron *(4165-4500 bp)*
- Inverted repeat 2: RhoGTPase – gamma-actin – mitochondrial heat shock protein 70 chaperone *(4448-5529 bp)*
- Intron *(5657-5770 bp)*
- GER4 promotor *(5820-8729 bp)*
- RB *(8894-8917 bp)*

Figure 10A:
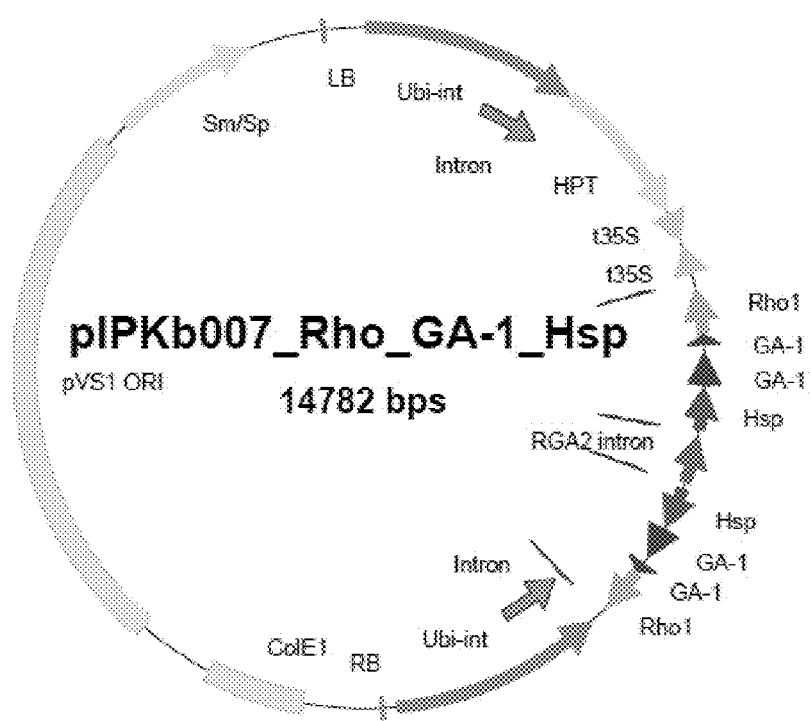

Fig. 10: Schematic structure of the construct No. 29 (pIPKb007_Rho_GA-1_Hsp) having the ubiquitin1 promotor and an insert of a triple sequence combination (e. g. RhoGTPase, gamma-actin and mitochondrial heat shock protein 70 chaperone):

FIG. 10B

Components of the construct in Fig. 10:
- LB *(14481-14504 bp)*
- ori T ColE1 *(7815-8512 bp)*
- ori pVS1 *(9061-12766 bp)*
- Sm/Sp *(12950-13960 bp)*
- Ubi promotor *(10-1517 bp)*
- HPT *(1544-2569 bp)*
- 35ST *(2594-2795 bp)*
- 35ST *(2840-3030 bp)*
- Inverted repeat 1: RhoGTPase – gamma-actin – mitochondrial heat shock protein 70 chaperone *(3141-4122 bp)*
- Intron *(4165-4500 bp)*
- Inverted repeat 2: RhoGTPase – gamma-actin – mitochondrial heat shock protein 70 chaperone *(4548-5529 bp)*
- Ubi promotor *(5662-7169 bp)*
- RB *(7257-7280 bp)*

Figure 11A:
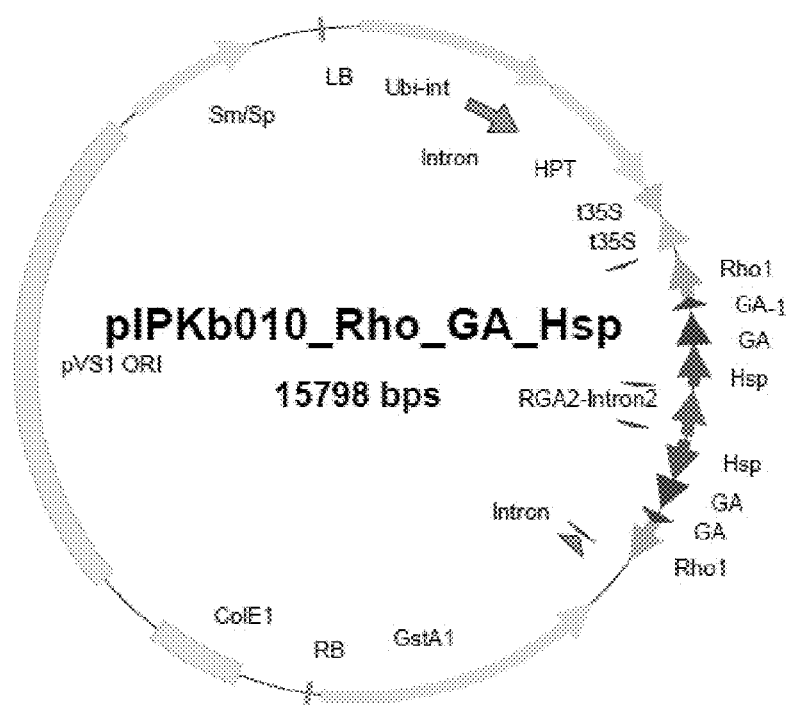

Fig. 11: Schematic structure of the construct No. 41 (pIPKb010_Rho_GA-1_Hsp) having the GstA1 promotor and an insert of a triple sequence combination (e. g. RhoGTPase, gamma-actin and mitochondrial heat shock protein 70 chaperone):

FIG. 11B

Components of the construct in Fig. 11:
- LB *(15497-15520 bp)*
- ori T ColE1 *(8831-9528 bp)*
- ori T pVS1 *(10077-13782 bp)*
- Sm/Sp *(13966-14976 bp)*
- Ubi promotor *(10-1517 bp)*
- HPT *(1544-2569 bp)*
- 35ST *(2594-2795 bp)*
- 35ST *(2834-3058 bp)*
- Inverted repeat 1: RhoGTPase – gamma-actin – mitochondrial heat shock protein 70 chaperone *(3141-4122 bp)*
- Intron *(4165-4500 bp)*
- Inverted repeat 2: RhoGTPase – gamma-actin – mitochondrial heat shock protein 70 chaperone *(4548-5529 bp)*
- GSTA1 promotor *(5988-8185 bp)*
- RB *(8273-8296 bp)*

SEQUENCE LISTING

<160> NUMBER OF SEQ ID NOS: 39

<210> SEQ ID NO 1
<211> LENGTH: 774
<212> TYPE: DNA
<213> ORGANISM: Fusarium sporotrichioides
<220> FEATURE:
<221> NAME/KEY: gene
<222> LOCATION: (1)..(774)
<223> OTHER INFORMATION: FsCon[0026] AAC

<400> SEQUENCE: 1
ttttctctcg actccctcca ttctctcttc cttctttcat cctcaatctc ccctcaatcc      60
tttcttcttg ttcaagggaa agaccatcac agccgctacc atgtctcctc ctgctgatca     120 aggacccag aaggtcttgg gcatgccccc cttcgtcgct gacttcctca tgggtggtgt      180
ctccgccgct gtctccaaga ctgctgctgc ccccatcgag cgtgtcaagc tcctcatcca     240
gaaccaggat gagatgctca agaccggtcg tctcgaccgc aagtacaacg gcattggtga     300

| | |
|---|---|
| ctgcttcaag cgcaccatgg ccgatgaggg tgtcatgtcc ctctggcgag gaaacaccgc | 360 |
| caacgtcatc cgatacttcc ccacccaggc cctgaacttc gctttccgtg acaagttcaa | 420 |
| gaagatgttc ggctacaaga aggacaagga tggctacgcc atgtggatgg ctggtaacct | 480 |
| tgcctccggt ggtgctgctg gtgccacttc tctgctcttc gtctactctc tggactacgc | 540 |
| ccgtactcgt cttgccaacg atgccaagaa cgccaagtcc ggtggtgacc gtcagttcaa | 600 |
| cggtctcgtc gacgtctaca agaagaccct cgcctctgac ggtattgccg gtctctaccg | 660 |
| tggtttcatg ccctccgttg ctggtatcgt tgtctaccgt ggtctctact cggaatgta | 720 |
| cgactccatc aagcccgtcg tcctcaccgg taacctccag ggcaacttcc ttgc | 774 |

<210> SEQ ID NO 2
<211> LENGTH: 1767
<212> TYPE: DNA
<213> ORGANISM: Gibberella zeae
<220> FEATURE:
<221> NAME/KEY: gene
<222> LOCATION: (1)..(1767)
<223> OTHER INFORMATION: GzCon[0015] EF1

<400> SEQUENCE: 2

| | |
|---|---|
| ctgagaagcw mgtcgcacga ggcccggcac gagcatccga tctgcgaatc tcacgttcat | 60 |
| cacaaacgta cacacaaacc atccacaacc gtcaaaatgg gtaaggagga aagactcac | 120 |
| cttaacgtcg tcgtcatcgg ccacgtcgac tctggcaagt cgaccactac cggtcacttg | 180 |
| atctaccagt gcggtggtat cgacaagcga accatcgaga agttcgagaa ggaagccgcc | 240 |
| gagctcggta agggttcctt caagtacgcc tgggttcttg acaagctcaa agccgagcgt | 300 |
| gagcgtggta tcaccattga tatcgccctc tggaagttcg agactcctcg ctactatgtc | 360 |
| accgtcattg acgctcccgg tcaccgtgat ttcatcaaga acatgatcac tggtacttcc | 420 |
| caggccgatt gcgccattct catcattgcc gccggtactg gtgagttcga ggctggtatc | 480 |
| tccaaggatg ccagacccg tgagcacgct ctccttgcct acacccttgg tgtcaagaac | 540 |
| ctcattgttg ccatcaacaa gatggacacc accaagtggt ctgaggcccg ttaccaggag | 600 |
| atcatcaagg agacctcttc tttcatcaag aaggtcggct acaaccccaa ggctgtcgct | 660 |
| ttcgtcccca tctccggttt caacggtgac aacatgctta ctgcctccac caactgcccc | 720 |
| tggtacaagg ttgggagcg tgagatcaag tctggcaagc tctccggaaa gaccctcctt | 780 |
| gaggccattg actccatcga gcccccaag cgtcccaacg caagcccct ccgacttccc | 840 |
| ctccaggatg tctacaagat tggcggtatt ggaacggttc ctgtcggccg tatcgagact | 900 |
| ggtatcatca agcccggtat ggtcgttacc ttcgctcctt ccaacgtcac cactgaagtc | 960 |
| aagtccgttg agatgcacca cgagcagctc actgagggac agcccggtga caacgttggt | 1020 |
| ttcaacgtga agaacgtttc cgtcaaggac atccgacgtg gtaacgtcgc tggtgactcc | 1080 |
| aagaacgacc ccccccatgg tgtgccgctt ctttcaccgcc caggtcatcg tcctcaacca | 1140 |
| ccccggtcag gtcggtgctg gttacgctcc cgtcctcgat tgccacactg cccacattgc | 1200 |
| ctgcaagttc gccgagatcc aggagaagat cgaccgccga accggtaagg ctactgaggc | 1260 |
| cgcccccaag ttcatcaagt ctggtgactc cgccatcgtc aagatggttc cctccaagcc | 1320 |
| catgtgtgtt gaggctttca ccgactaccc tcctctgggt cgtttcgccg tccgtgacat | 1380 |
| gcgacagacc gtcgccgtcg gtgtcatcaa ggccgtcgag aagtccactg gcgctgctgg | 1440 |
| caaggtcacc aagtccgctg ccaaggctgg taagaaataa gcgcattatt tctgaaatga | 1500 |
| caaccttcgg tgggatctta cgactctggt ctcacgccca agggctgatg tactcgcttc | 1560 |

```
tacgacgaaa tgatcatgtt ggcatgagca ctcggcttat gtctgggggc acgagatgag    1620
gcgaaaataa aagcctggga tcttgtgcaa atcaaaaata ggaatagaga gtctagaagt    1680
gattcgtgca aaaaaaaaaa aaaaaaaaa aaaaaaaaa aaaaaaaact cgagaaactc      1740
gagactagtt ctctctctcc ctcgtgc                                         1767
```

<210> SEQ ID NO 3
<211> LENGTH: 1579
<212> TYPE: DNA
<213> ORGANISM: Gibberella zeae
<220> FEATURE:
<221> NAME/KEY: gene
<222> LOCATION: (1)..(1579)
<223> OTHER INFORMATION: GzCon[0219] GA

<400> SEQUENCE: 3

```
gctcttcttt tcccgtaagc ttgctcctca ctaattctag catcgcatct catcacattt      60
gtcttcttta taccactttg tccttcttt ttcttcctcg ccttgcaatc ttgggcacga      120
ggcgtctctt cttttccct ttcccataca cacaccgtaa tccacagcca tggaggaaga     180
agttgctgct ctcgtcattg acaatggttc gggtatgtgc aaggccggtt tcgccggtga    240
tgatgctccc cgagctgttt tcccttccat tgtcggtcgc ccccgtcacc atggtatcat    300
gatcggtatg ggtcagaagg actcttacgt tggtgatgag gctcagtcca agcgtggtat    360
cctcacactg cgatacccca tcgagcacgg tgttgttacc aactgggacg acatggagaa    420
gatttggcac cacaccttct acaacgagct gcgtgtcgcc cccgaggagc accccgtcct    480
gctcaccgag gctcccatca ccccaagtc caaccgtgag aagatgaccc agattgtctt    540
cgagaccttc aacgccccg ctttctacgt ctctatccag gccgttctgt ccctgtacgc    600
ctccggtcgt accaccggta tcgttctgga ctctggtgat ggtgtcactc acgttgtccc    660
catttacgag ggtttcgccc ttccccacgc cattgcccgt gtcgacatgg ctggtcgtga    720
tcttaccgac tacctcatga agattcttgc tgagcgcggt tacaccttct ccaccactgc    780
cgagcgagaa atcgtccgtg acatcaagga gaagctctgc tacgtcgccc ttgacttcga    840
gcaggagatc cagactgctg cccagagctc cagcttggag aagtcttacg agcttcctga    900
cggtcaggtt atcaccattg gtaacgagcg attccgtgct cctgaggctc tcttccagcc    960
ttctgtcctt ggtcttgaga gcggtggtat ccacgtcacc actttcaact ccatcatgaa    1020
gtgtgatgtc gatgtccgaa aggatctcta cggaaacatt gtcatgtctg gtggtaccac    1080
catgtacccc ggtctctccg accgtatgca gaaggagatc actgctcttg ctccttcttc    1140
catgaaggtc aagatcattg ctcctcccga gcgaaagtac tccgtctgga tcggtggttc    1200
cattctcgct tccctgtcca ccttccagca aatgtggatc tccaagcagg agtacgacga    1260
gagcggtcct tcaatcgttc accgcaagtg cttctaagct acccgaccga caaattaaat    1320
cctcccactc gcctaacgac aagatcatgg aggtggcgac agacgctaag ctttgggtgg    1380
ttggccaacg tcaatgtcga atctcgtatc tacgaaaagt ttttgacatg gtcgaaagag    1440
tgggcgttgc gcttgttacg aagagatgtg atggccccct tcttgtagt tcgcgtataa    1500 tgcgtgccta ggggtagaag ccgaggttga catacaaata ctttttact ttccgmwwar    1560 aaaaaaaaaa actcgaggg                                                 1579
```

<210> SEQ ID NO 4
<211> LENGTH: 1668
<212> TYPE: DNA
<213> ORGANISM: Gibberella zeae -continued
<220> FEATURE:
<221> NAME/KEY: gene
<222> LOCATION: (1)..(1668)
<223> OTHER INFORMATION: GzCon[2886] Hsp

<400> SEQUENCE: 4

```
gcacgaggag agagagagag aactagtttc gagttttttt tttttttttt tttttttwtg     60
aatgtatgat tcattgattc attmaagtac ataraycacc ttagcttttc ataaccgtaa    120
agtcgcataa aaacagaaaa aaggaaaatc taatctcatc atcccatgaa aacgactagc    180
ctccgcatta tacccatgga tatatgaccg ctctagaagt cgagactgat gttattgggg    240
tatcaaagaa tttagtcgac ctcctcgacg gtgggaccat cgtcaccacc ggcaccgggg    300
gcggggccac cagcaccagg gaagccacca gggccgccgg gcatgccggg catgccaccg    360
ggagcaccct caccaccagc tccgtagaac ttcatcatga tggggttagc cttgccctcg    420
agctccttct ggtgctcctc atactcctca cgagtagcct gctggttgtc atcgagccac    480
tggacgacct tgtcaatctc agcagtgagg gtctccttgt cggaagcctc aatcttctcc    540
tcgaccttgg ggtcggagag agtgttgcgg agagagtaag cgtaagactc aagaccgttc    600
ttggcagcga cacgcttgcc ctcggcctca tcctcctcct tgtacttctc agcatcgttg    660
agcatgcgct cgatctcctc cttggacagg cggcccttgt cgttggtgat gacgatcttg    720
ttggacttgc cggtaccctt ctcgacggcg gaaacgttca tgataccgtt ggcatcgaga    780
tcgaaggtga cctcaatctg ggaacaccca cggggagcag gggggatacc agtgagctcg    840
aacttgccca tgaggttgtt gtccttggtg cgctggcgct caccctcgta gacctggata    900
aggacaccag gctggttgtc ggagaaggta gagaagacct cggacttctt ggtgggaatg    960
gtggtgttgc gggggatgag cttggtcatc ataccaccag cggtctcgat accgagagag   1020
agggggcga cgtcgaggag cagaatctcg ttggtggcct tgctagaggt gtcaccagag   1080
agaatagcag cctggacagc ggcaccgtag gcaacagcct catcaggatt gatggacttg   1140
ttgggctcct ttccgttgaa gtagtcggtg atgagcttct ggacacgggg gatacgggta   1200
gatccaccga cgaggacgat ctcgtggacg agggacttgt cgatcttggc gtcggtaagg   1260
acacggtcga cgggctggat ggtggatcgg aagagatcct ggcagagctc ctcgaaacga   1320
gcacgggtga tggaagtgta gaaatcaata ccctcgaaga gagagtcgat ctcaatggag   1380
gtctgagcgg aagaagagag agttcgcttg gcgcgctcac aagcggttcg gagacgtcga   1440
agagcacgga cgttggtgct tagatccttc ttatgctttc gcttgaactc gttaacgaag   1500
tggttaacga ggcggttgtc gaaatcttca ccacccaagt gagtgtcacc ggcagtagac   1560
ttgacctcga agataccctc ctcaatggta aggagagaga catcgaagsy wcswscrcca   1620
agatcgaaga tgaggacgtt gcgctcaccc tcaaccttct cctcgtgc                1668
```

<210> SEQ ID NO 5
<211> LENGTH: 468
<212> TYPE: DNA
<213> ORGANISM: Fusarium sporotrichioides
<220> FEATURE:
<221> NAME/KEY: gene
<222> LOCATION: (1)..(468)
<223> OTHER INFORMATION: FsCon[0840] Rho

<400> SEQUENCE: 5

```
ccaagctcaa ctcaagctca agctcgcatt ctacgccagc aaattcgtcc atttctcaca     60
acttcttcac ccaaaaacac ttctaatcaa taaccatggc tgagatccgc cgaaagctcg    120
```

```
tcattgtcgg cgatggtgct tgtggtaaaa cctgtttgtt gatcgttttc tccaagggca    180
ctttccccga ggtctacgtc cccaccgtct tcgagaacta tgtcgccgat gtcgaggttg    240
acggcaagca cgtcgagctc gccctatggg atactgctgg tcaggaggat tacgaccgtc    300
ttcgacctct ctcttacccc gactcccacg ttatcttgat ctgcttcgct gttgactctc    360
ccgactctct cgacaacgtc caggagaagt ggatctctga ggttctgcac ttctgccagg    420
gkctccctat catccttgtc ggctgcaaga aggatttgcg atacgacc                 468

<210> SEQ ID NO 6
<211> LENGTH: 301
<212> TYPE: DNA
<213> ORGANISM: Fusarium sporotrichioides
<220> FEATURE:
<221> NAME/KEY: gene
<222> LOCATION: (1)..(301)
<223> OTHER INFORMATION: FsCon[0026] AAC Nt. 322-622

<400> SEQUENCE: 6
cgatgagggt gtcatgtccc tctggcgagg aaacaccgcc aacgtcatcc gatacttccc     60
cacccaggcc ctgaacttcg ctttccgtga caagttcaag aagatgttcg gctacaagaa    120
ggacaaggat ggctacgcca tgtggatggc tggtaacctt gcctccggtg gtgctgctgg    180
tgccacttct ctgctcttcg tctactctct ggactacgcc cgtactcgtc ttgccaacga    240
tgccaagaac gccaagtccg gtggtgaccg tcagttcaac ggtctcgtcg acgtctacaa    300
g                                                                   301

<210> SEQ ID NO 7
<211> LENGTH: 298
<212> TYPE: DNA
<213> ORGANISM: Gibberella zeae
<220> FEATURE:
<221> NAME/KEY: gene
<222> LOCATION: (1)..(298)
<223> OTHER INFORMATION: GzCon[0015] EF1 Nt. 907-1204

<400> SEQUENCE: 7
atcaagcccg gtatggtcgt taccttcgct ccttccaacg tcaccactga agtcaagtcc     60
gttgagatgc accacgagca gctcactgag ggacagcccg tgacaacgt tggtttcaac    120 gtgaagaacg tttccgtcaa ggacatccga cgtggtaacg tcgctggtga ctccaagaac    180 gaccccccc atgggtgccg cttctttcac cgcccaggtc atcgtcctca accacccgg    240 tcaggtcggt gctggttacg ctcccgtcct cgattgccac actgcccaca ttgcctgc    298

<210> SEQ ID NO 8
<211> LENGTH: 305
<212> TYPE: DNA
<213> ORGANISM: Gibberella zeae
<220> FEATURE:
<221> NAME/KEY: gene
<222> LOCATION: (1)..(305)
<223> OTHER INFORMATION: GzCon[0219] GA Nt. 837-1141

<400> SEQUENCE: 8
tcgagcagga gatccagact gctgcccaga gctccagctt ggagaagtct tacgagcttc     60
ctgacggtca ggttatcacc attggtaacg agcgattccg tgctcctgag gctctcttcc    120
agccttctgt ccttggtctt gagagcggtg gtatccacgt caccactttc aactccatca    180
tgaagtgtga tgtcgatgtc cgaaaggatc tctacgaaa cattgtcatg tctggtggta    240
```

```
ccaccatgta ccccggtctc tccgaccgta tgcagaagga gatcactgct cttgctcctt        300
cttcc                                                                    305

<210> SEQ ID NO 9
<211> LENGTH: 356
<212> TYPE: DNA
<213> ORGANISM: Gibberella zeae
<220> FEATURE:
<221> NAME/KEY: gene
<222> LOCATION: (1)..(356)
<223> OTHER INFORMATION: GA-1

<400> SEQUENCE: 9
ttcgagcagg agatccagac tgctgcccag agctccagct tggagaagtc ttacgagctt        60
cctgacggtc aggttatcac cattggtaac gagcgattcc gtgctcctga ggctctcttc       120
cagccttctg tccttggtct tgagagcggt ggtatccacg tcaccacttt caactccatc       180
atgaagtgtg atgtcgatgt ccgaaaggat ctctacggaa acattgtcat ggtaagttct       240
gcaaatcgaa agcactccaa ctgttctaac atgtctttag tctggtggta ccaccatgta       300
ccccggtctc tccgaccgta tgcagaagga gatcactgct cttgctcctt cttcca          356

<210> SEQ ID NO 10
<211> LENGTH: 356
<212> TYPE: DNA
<213> ORGANISM: Gibberella zeae
<220> FEATURE:
<221> NAME/KEY: gene
<222> LOCATION: (1)..(356)
<223> OTHER INFORMATION: GzCon[2886] Hsp Nt. 842-1197

<400> SEQUENCE: 10
acttgcccat gaggttgttg tccttggtgc gctggcgctc accctcgtag acctggataa        60
ggacaccagg ctggttgtcg gagaaggtag agaagacctc ggacttcttg gtgggaatgg       120
tggtgttgcg ggggatgagc ttggtcatca taccaccagc ggtctcgata ccgagagaga       180
ggggggcgac gtcgaggagc agaatctcgt tggtggcctt gctagaggtg tcaccagaga       240
gaatagcagc ctggacagcg gcaccgtagg caacagcctc atcaggattg atggacttgt       300
tgggctcctt tccgttgaag tagtcggtga tgagcttctg gacacggggg atacgg          356

<210> SEQ ID NO 11
<211> LENGTH: 308
<212> TYPE: DNA
<213> ORGANISM: Fusarium sporotrichioides
<220> FEATURE:
<221> NAME/KEY: gene
<222> LOCATION: (1)..(308)
<223> OTHER INFORMATION: FsCon[0840] Rho Nt. 137-444

<400> SEQUENCE: 11
tgcttgtggt aaaacctgtt tgttgatcgt tttctccaag ggcactttcc ccgaggtcta        60
cgtccccacc gtcttcgaga actatgtcgc cgatgtcgag gttgacggca agcacgtcga       120
gctcgcccta tgggatactg ctggtcagga ggattacgac cgtcttcgac ctctctctta       180
ccccgactcc cacgttatct tgatctgctt cgctgttgac tctcccgact ctctcgacaa       240
cgtccaggag aagtggatct ctgaggttct gcacttctgc cagggkctcc ctatcatcct       300
tgtcggct                                                                 308
```

<210> SEQ ID NO 12
<211> LENGTH: 588
<212> TYPE: DNA
<213> ORGANISM: Artificial
<220> FEATURE:
<223> OTHER INFORMATION: recombinant nucleic acid molecule
<220> FEATURE:
<221> NAME/KEY: misc_feature
<222> LOCATION: (1)..(588)
<223> OTHER INFORMATION: AAC consensus sequence shortened

<400> SEQUENCE: 12

```
gcagaccgtt cttgggcatg cccccctttcg tcgctgactt cctcatgggt ggtgtctccg      60
ccgctgtctc caagaccgct gcygccccca tygagcgtgt caagctcctc atccagaacc     120
aggatgagat gctgaagacc ggtcgtctyg accgcaagta cgacggcatt ggtgastgct     180
tcaagcgyac caccgcsgat gagggtgtca tgtccctctg gcgwgghaac actgccaacg     240
tcatccgtta cttccctacc caggccctga acttcgcttt ccgtgacaag ttcaagtcga     300
tgttcggcta caagaaggac cgtgatggct acgccatgtg gatggcyggt aacytkgcct     360
ccggtggtgc tgctggtgcc acttccctcc tcttcgtcta ctccctcgac tacgcccgta     420
cycgtcttgc caacgacgcc aagaacgcca agaccggtgg tgaccgtcag ttcaacggtc     480
tsgtcgatgt ctacaagaag accctcgcct ctgacggtat tgccggtctc taccgtggtt     540
tcggtccttc cgttgctggt atcgtcgtyt accgtggtct ctacttcg                 588
```

<210> SEQ ID NO 13
<211> LENGTH: 1353
<212> TYPE: DNA
<213> ORGANISM: Artificial
<220> FEATURE:
<223> OTHER INFORMATION: recombinant nucleic acid molecule
<220> FEATURE:
<221> NAME/KEY: misc_feature
<222> LOCATION: (1)..(1353)
<223> OTHER INFORMATION: EF1 consensus sequence shortened

<400> SEQUENCE: 13

```
atgggtaaag gagaagactc acatcaacgt cgtcgtcatc ggccacgtcg actccggcaa      60
gtcgaccacc accggtcact tgatctacaa gtgcggtggt atcgacaagc gtaccatcga     120
gaagttcgag aaggaagccg ccgagctcgg yaagggttcc ttcaagtacg cctgggttct     180
tgacaagctc aaggccgagc gtgagcgtgg tatcaccatc gacatcgccc tctggaagtt     240
cgagacyccc aagtactatg ttaccgtcat tgacgcccct ggtcaccgtg acttcatcaa     300
gaacatgatc actggtacct cccaggccga ctgcgccatt ctcatcattg ccgctggtac     360
tggtgagttc gaggctggta tctccaagga tggccagact cgtgagcacg ctctcctcgc     420
ctacaccctc ggtgtcaagc agctcatcgt ygccatcaac aagatggaca ccaccaagtg     480
gtccgaggac cgttwccagg agatcatcaa ggagacctcc aacttcatca agaaggtcgg     540
ctacaaccce aagacygtcg ccttcgtccc catctccggt ttcaacggtg acaacatgmt     600
cgacgcctcc accaactgcc cctggtacaa gggttgggag aaggagacca agkcwggcaa     660
ggycaccggc aagaccctcc tcgaggccat cgacgccatc gagcccccca gcgtcccac      720
cgacaagccc ctccgtcttc ccctccagga tgtctacaag atcggyggta ttggmactgt     780
tcccgtcggc cgtrtcgaga cyggtatcat caagcccggy atggtcgtca ccttcgctcc     840
cgccaacgtc accactgaag tcaagtccgt cgagatgcac cacagcagc tcactgaggg     900
tstteccggt gacaacgtcg gtttcaacgt caagaacgtt tccgtcaagg acattcgccg     960
```

```
tggtaacgtc gctggtgact ccaagaacga ccccccccaag ggtgccgctt ccttcaacgc    1020
ycaggtcaty gtcctyaacc accctggtca ggtcggtgct ggttacgccc ccgttctcga    1080
ttgccacact gcccacattg cctgcaagtt ctccgagctc ctcgagaaga tcgaccgccg    1140
taccggtaag tccattgagg actcccccaa gttcatcaag tctggtgacg ctgccatcgt    1200
caagatggtt ccctccaagc ccatgtgtgt tgaggccttc acygactacc ctcctctggg    1260
mcgtttcgcc gtccgtgaca tgcgtcagac cgtcgctgtc ggtgtcatca agtccgtcga    1320
caagtccacg acactgccgg taaggtcacc aag                                 1353
```

<210> SEQ ID NO 14
<211> LENGTH: 1038
<212> TYPE: DNA
<213> ORGANISM: Artificial
<220> FEATURE:
<223> OTHER INFORMATION: recombinant nucleic acid molecule
<220> FEATURE:
<221> NAME/KEY: misc_feature
<222> LOCATION: (1)..(1038)
<223> OTHER INFORMATION: GA consensus sequence shortened

<400> SEQUENCE: 14

```
atggaggaag aagtcgcwgc tctcgtcaty gacaatggtt cgggtatgtg caaggccggt      60
ttcgccggtg acgatgctcc ccgagctgtc ttcccttcca ttgtcggtcg ccccgtcac     120 catggtatca tgattggtat gggccagaag gactcgtacg ttggtgatga ggcccagtcc    180
aagcgtggta tcctcactct gcggtacccc atcgagcacg gtgtygtcac caactgggac    240
gacatggaga agatctggca ccacaccttc tacaacgagc tgcgtgtcgc ccccgaggag    300 cacccccgtcc tgctgactga ggctcccatc aacccccaagt ccaaccgtga agagatgacg    360
cagatcgtct tcgagacctt caacgccccc gccttctacg tctccatcca ggccgtkctg    420
tccctgtacg cctccggtcg taccactggt atcgtgctcg actcyggtga cggtgttact    480
cacgttgtgc ccatctacga gggttttckc ctkccccacg ccattgcccg tgtcgacatg    540
gctggtcgtg acttgaccga ctacctgatg aagatcttgg ctgagcgcgg ttacaccttc    600
tccaccactg ccgagcgwga aatcgtccgt gacatcaagg agaagctctg ctacgtcgcc    660
cttgacttcg agcaggagat ccagactgct gcccagtcct ccagcytgga gaagtcctac    720
gagcttcccg acggacaggt tatcaccatc ggcaacgagc gcttccgtgc tcctgaggct    780
ctgttccagc cttctgtcct gggtcttgag agcggtggta tccacgtcac cacttttcaac    840 tccatcatga agtgtgatgt cgatgtccga aaggatctgt acggcaacat tgtcatgtct    900
ggtggtacca ccatgtaccc tggtatctcc gaccgtatgc agaaggagat cactgctctt    960
gccccktcct csatgaaggt caagatcatt gctcctcccg agcgcaagta ctccgtctgg   1020
atcggtggtt ccattctc                                                 1038
```

<210> SEQ ID NO 15
<211> LENGTH: 601
<212> TYPE: DNA
<213> ORGANISM: Artificial
<220> FEATURE:
<223> OTHER INFORMATION: recombinant nucleic acid molecule
<220> FEATURE:
<221> NAME/KEY: misc_feature
<222> LOCATION: (1)..(601)
<223> OTHER INFORMATION: Hsp consensus sequence shortened

<400> SEQUENCE: 15

```
tccacgagat cgtcctcgty ggyggwtcya cccgtatccc ccgtgtccag aagctcatca    60
ccgactactt caacggaaag gagcccaaca agtccatcaa cccygatgag gctgttgcct   120
acggtgctgc cgtccaggct gccattctct ctggtgacac cacctccaag tccaccaacg   180
agatcctgct yctcgatgtc gccccsctst ctctcggtat cgagaccgct ggtggtatga   240
tgaccaagct catccccgc aacaccacca tccccaccaa gaagtcygag gtcttctcca    300
ccttctccga caaccagcct ggtgtgctca tccaggtcta cgagggtgag cgccagcgca   360
ccaaggacaa caacctsctg gcaagttcg agcttaccgg catcccmcct gctccccgtg   420
gtgttcccca gattgaggtc accttcgacc tsgatgccaa cggtatcatg aacgtctccg   480
ccgtcgagaa gggcaccggc aagaccaaca agattgtcat caccaacgac aagggccgyc   540
tgtccaagga ggagatygag cgcatgcttg cygaggccga aagtacaag gaggaggatg    600
a                                                                  601
```

<210> SEQ ID NO 16
<211> LENGTH: 414
<212> TYPE: DNA
<213> ORGANISM: Artificial
<220> FEATURE:
<223> OTHER INFORMATION: recombinant nucleic acid molecule
<220> FEATURE:
<221> NAME/KEY: misc_feature
<222> LOCATION: (1)..(414)
<223> OTHER INFORMATION: Rho consensus sequence shortened

<400> SEQUENCE: 16

```
aatccatmac catggctgaa atccgccgaa agctcgtcat tgtcgghgay ggtgcttgtg    60
gtaagacytg tttgttgatt gtcttctcca agggcachtt cccmgaggtc tacgtcccma   120
ccgtcttcga gaactatgtc gccgatgtcg aggtcgatgg caagcacgtc gagctcgcgc   180
tatgggatac bgctggtcag gaggattacg accgtcttcg acctctctca taccccgact   240
cscacgttat cctgatctgc ttcgccgttg actctcccga ttccctcgay aacgtycagg   300
agaagtggat ctccgaggtc ctscayttct gccagggtct ccctatcatc cttgtcggct   360
gcaagaagga tttgcgayac gaccagaaga ccattgagga gctccacaag acca         414
```

<210> SEQ ID NO 17
<211> LENGTH: 1597
<212> TYPE: DNA
<213> ORGANISM: Artificial
<220> FEATURE:
<223> OTHER INFORMATION: DNA sequence
<220> FEATURE:
<221> NAME/KEY: misc_feature
<222> LOCATION: (1)..(1597)
<223> OTHER INFORMATION: consensus sequence for AAC

<400> SEQUENCE: 17

```
gcagaccgtt cttgggcatg cccccttcg tcgctgactt cctcatgggt ggtgtctccg     60
ccgctgtctc caagaccgct gcygccccca tygagcgtgt caagctcctc atccagaacc   120
aggatgagat gctgaagacc ggtcgtctyg accgcaagta cgacggcatt ggtgastgct   180
tcaagcgyac caccgcsgat gagggtgtca tgtccctctg gcgwgghaac actgccaacg   240
tcatccgtta cttccctacc caggcctga acttcgcttt ccgtgacaag ttcaagtcga   300
tgttcggcta caagaaggac cgtgatggct acgccatgtg gatggcyggt aacytkgcct   360
ccggtggtgc tgctggtgcc acttccctcc tcttcgtcta ctccctcgac tacgcccgta   420
```

-continued

| | |
|---|---|
| cycgtcttgc caacgacgcc aagaacgcca agaccggtgg tgaccgtcag ttcaacggtc | 480 |
| tsgtcgatgt ctacaagaag accctcgcct ctgacggtat tgccggtctc taccgtggtt | 540 |
| tcggtccttc cgttgctggt atcgtcgtyt accgtggtct ctacttcggw atgtacgayt | 600 |
| ccatcaagcc agtcctcctc ayyggwmmyc tygagggyaa cttccttgcw tccttcttgc | 660 |
| tcggatggac cgtcaccact ggtgccggta tcgcctctta cccattggac accatccgtc | 720 |
| gtcgtatgat gatgacttct ggtgaggccg tcaagtacaa gtcttccttg gatgctgsyc | 780 |
| gycaratcgt ygccaaggag ggwgtyaagt ctctcttcaa gggtgctggt gccaacattc | 840 |
| tccgtggtgt tgcaggtgct ggtgtcytgt ccatctacga tcaratgcar gtcytgatgt | 900 |
| tcggaaaggc attcaagtaa aygwatcgta gaatggagtg aagggatgag ttgaktgtag | 960 |
| aggtggttga tgataatgcg aaatgagcgc cttgrggtcg gtccgtggtt gaaactaaaa | 1020 |
| ggttgagats gtagtacaga tcsattgcat tgtgttrsag atacttgmcg tgtagtctgm | 1080 |
| cacarcawga tctatacrat ytgagtsgct tmtgcacaga gtctttatct aatcttkcwt | 1140 |
| tgccttccgt tctatgcckv tgtaatttat acaccaattc aavttcccntt tactgtctrt | 1200 |
| tcncttaact gagddttmaa tttkrmkcmt stmktcatcc tkktcaktgc tgacycytrt | 1260 |
| ktctmcactc trtctwttcs ytttcwtcca tttgcymywc ycmctcctat cmktagcata | 1320 |
| ctwcgtaywa tcyktsttgc ctaacgtmyk wactaccycy mtttmytrct twkcgattac | 1380 |
| tmtyyctwtm tyyctycgkt wmcmytcwcs twymtgttkc attmtctctg actctctctm | 1440 |
| tyctcccctc tmtayacyyk yyttrtyctk tygccmytmr ycctmtcttc tmattttcct | 1500 |
| acttctattc tcttgctatt tctctccctat ctgttccatc ccttcattca tcatttctct | 1560 |
| ctctctgctt caacgattat catcactatt ctatctc | 1597 |

<210> SEQ ID NO 18
<211> LENGTH: 2085
<212> TYPE: DNA
<213> ORGANISM: Artificial
<220> FEATURE:
<223> OTHER INFORMATION: DNA sequence
<220> FEATURE:
<221> NAME/KEY: misc_feature
<222> LOCATION: (1)..(2085)
<223> OTHER INFORMATION: consensus sequence for EF1

<400> SEQUENCE: 18

| | |
|---|---|
| atgggtaaag gagaagactc acatcaacgt cgtcgtcatc ggccacgtcg actccggcaa | 60 |
| gtcgaccacc accggtcact tgatctacaa gtgcggtggt atcgacaagc gtaccatcga | 120 |
| gaagttcgag aaggaagccg ccgagctcgg yaagggttcc ttcaagtacg cctgggttct | 180 |
| tgacaagctc aaggccgagc gtgagcgtgg tatcaccatc gacatcgccc tctggaagtt | 240 |
| cgagacyccc aagtactatg ttaccgtcat tgacgcccct ggtcaccgtg acttcatcaa | 300 |
| gaacatgatc actggtacct cccaggccga ctgcgccatt ctcatcattg ccgctggtac | 360 |
| tggtgagttc gaggctggta tctccaagga tggccagact cgtgagcacg ctctcctcgc | 420 |
| ctacaccctc ggtgtcaagc agctcatcgt ygccatcaac aagatggaca ccaccaagtg | 480 |
| gtccgaggac cgttwccagg agatcatcaa ggagacctcc aacttcatca agaaggtcgg | 540 |
| ctacaacccc aagacygtcg ccttcgtccc catctccggt ttcaacggtg acaacatgmt | 600 |
| cgacgcctcc accaactgcc cctggtacaa gggttgggag aaggagacca agkcwggcaa | 660 |
| ggycaccggc aagaccctcc tcgaggccat cgacgccatc gagccccca agcgtcccac | 720 |
| cgacaagccc ctccgtcttc ccctccagga tgtctacaag atcggyggta ttggmactgt | 780 |

```
tcccgtcggc cgtrtcgaga cyggtatcat caagcccggy atggtcgtca ccttcgctcc      840
cgccaacgtc accactgaag tcaagtccgt cgagatgcac cacgagcagc tcactgaggg      900
tsttcccggt gacaacgtcg gtttcaacgt caagaacgtt tccgtcaagg acattcgccg      960
tggtaacgtc gctggtgact ccaagaacga ccccccaag ggtgccgctt ccttcaacgc      1020
ycaggtcaty gtcctyaacc accctggtca ggtcggtgct ggttacgccc ccgttctcga      1080
ttgccacact gcccacattg cctgcaagtt ctccgagctc ctcgagaaga tcgaccgccg      1140
taccggtaag tccattgagg actcccccaa gttcatcaag tctggtgacg ctgccatcgt      1200
caagatggtt ccctccaagc ccatgtgtgt tgaggccttc acygactacc ctcctctggg      1260
mcgtttcgcc gtccgtgaca tgcgtcagac cgtcgctgtc ggtgtcatca agtccgtcga      1320
caagtccacg acactgccgg taaggtcacc aagkccgccg ycaaggctgg tgccaagaaa      1380
taaacttatt tatgaatgac gaccttcagt bggatsttgc gastttgwtt caygctcatg      1440
aggctgatct actggcttgt acgccgaatc gatcatttgc atgagcactc gkgtaatgac      1500
ttgsagaktc ttsagagatw ttcaaatgcc tgctgatsac gttgtggcac atcacataga      1560
acacttmgtc kagaaatgac ttcaragaaa aaaaaaaaa acawgtcatg accaaacgcc      1620
gagatcactt ctgaggactc tatgtagact aaagcacatg tcaagaattt ttttgagtta      1680
cgaaatccca aaccgtcatt tcatcatgtg ccccaataaa aaccgagtac tcttttgtga      1740
taaagccaaa attgaccgga aaacctgcgt ttgcgaacga ggaaagtgcc caagatgcta      1800
cgacatgctt cctggcttgt cgtggctcga cattagatgt ttgctgkttg gttgatcgca      1860
gcvtyatatt tctttkggcs ggcccttgg ccacgcgggr accttgggtg acccttgscc      1920
ctggggtacc ctggggactt ggtcgacggc tcttgatgac accgaacagc gacggtctga      1980
cgcatgtcac ggacggcgaa acgaccaagg ggagggtact cggagaaagt ctcgacacac      2040
atgggcttgg actcgtscgc bcmmgratmm ctagcagacc ggrgg                     2085
```

<210> SEQ ID NO 19
<211> LENGTH: 1807
<212> TYPE: DNA
<213> ORGANISM: Artificial
<220> FEATURE:
<223> OTHER INFORMATION: DNA sequence
<220> FEATURE:
<221> NAME/KEY: misc_feature
<222> LOCATION: (1)..(1807)
<223> OTHER INFORMATION: consensus sequence for GA

<400> SEQUENCE: 19

```
ccacgcgtcc gccctttcct gcccaacaac tttcctctcy btcaacgatc twcttttccc       60
atcaacttgt cgcctgcaac aatctctgct ctacatcttc agatctatca ttcctccgcg      120
actttcgcga ttcttctwtc tcctgacctt gattcatccg ccagctctct tmatctccct      180
attccactac acaccttaat cmatcacgat ggaggaagaa gtcgcwgctc tcgtcatyga      240
caatggttcg ggtatgtgca aggccggttt cgccggtgac gatgctcccc gagctgtctt      300
cccttccatt gtcggtcgcc cccgtcacca tggtatcatg attggtatgg gccagaagga      360
ctcgtacgtt ggtgatgagg cccagtccaa gcgtggtatc ctcactctgc ggtacccat      420 cgagcacggt gtygtcacca actgggacga catggagaag atctggcacc acaccttcta      480
caacgagctg cgtgtcgccc cgaggagca cccgtcctg ctgactgagg ctcccatcaa      540
ccccaagtcc aaccgtgaga agatgacgca gatcgtcttc gagaccttca acgccccgc      600 cttctacgtc tccatccagg ccgtkctgtc cctgtacgcc tccggtcgta ccactggtat      660
```

| cgtgctcgac tcyggtgacg gtgttactca cgttgtgccc atctacgagg gtttckccct | 720 |
| kccccacgcc attgcccgtg tcgacatggc tggtcgtgac ttgaccgact acctgatgaa | 780 |
| gatcttggct gagcgcggtt acaccttctc caccactgcc gagcgwgaaa tcgtccgtga | 840 |
| catcaaggag aagctctgct acgtcgccct tgacttcgag caggagatcc agactgctgc | 900 |
| ccagtcctcc agcytggaga agtcctacga gcttcccgac ggacaggtta tcaccatcgg | 960 |
| caacgagcgc ttccgtgctc ctgaggctct gttccagcct tctgtcctgg gtcttgagag | 1020 |
| cggtggtatc cacgtcacca ctttcaactc catcatgaag tgtgatgtcg atgtccgaaa | 1080 |
| ggatctgtac ggcaacattg tcatgtctgg tggtaccacc atgtaccctg gtatctccga | 1140 |
| ccgtatgcag aaggagatca ctgctcttgc cccktcctcs atgaaggtca agatcattgc | 1200 |
| tcctcccgag cgcaagtact ccgtctggat cggtggttcc attctcgctt cgctgtcgac | 1260 |
| cttccagcag atgtggatct cgaagcagga gtacgacgag agcggaccct csatcgtsca | 1320 |
| ccgcaagtgc ttctaagcgc ctgaccgacg attgtgctcc aactcgctta cgaactggak | 1380 |
| cagaaatgtc gcgacagacg ctaagcktcg dgaggttggg tgcttcgaag ctcgtccgaa | 1440 |
| actcgtrtct gcgaacattt attacatggt cgatgagtsa acgttgcgca tgtacgagag | 1500 |
| atggatggcc tgwtttcttg caggtcgagt acaatgcgtc tagggctasa agbcgaggtt | 1560 |
| gacatacgaa tacgtgtcta ctwtccgctt agarctgacg acatawtcga ggggttgatc | 1620 |
| atgcarcgyg agtchgtccc ttgctctaga gaatcramtt amawggtmgw aamtgaaaag | 1680 |
| agbtcrgtgg mcatcctgsc rmrcartraw msatmygmya acgmmamwma rwaramrwrd | 1740 |
| mammmwwmaaa aaaaaaaaaa aaaaaaaaaa aaaaaaaaaa aaaaaaaaaa aagggcggcc | 1800 |
| gctctan | 1807 |

<210> SEQ ID NO 20
<211> LENGTH: 1687
<212> TYPE: DNA
<213> ORGANISM: Artificial
<220> FEATURE:
<223> OTHER INFORMATION: DNA sequence
<220> FEATURE:
<221> NAME/KEY: misc_feature
<222> LOCATION: (1)..(1687)
<223> OTHER INFORMATION: consensus sequence for Hsp

<400> SEQUENCE: 20

| gcacgaggag aaggttgagg gtgagcgcaa cgtcctcatc ttcgatcttg gygswsgwrs | 60 |
| cttcgatgtc tctctcctta ccattgagga gggtatcttc gaggtcaagt ctactgccgg | 120 |
| tgacactcac ttgggtggtg aagatttcga caaccgcctc gttaaccact tcgttaacga | 180 |
| gttcaagcga aagcataaga aggatctaag caccaacgtc cgtgctcttc gacgtctccg | 240 |
| aaccgcttgt gagcgcgcca agcgaactct ctcttcttcc gctcagacct ccattgagat | 300 |
| cgactckcts twcgagggta ttgacttcta cacctccatc acccgtgccc gtttcgagga | 360 |
| gctctgccag gatctcttcc gatccaccat ccagcccgtc gaccgtgtcc ttaccgacgc | 420 |
| caagatcgac aagtccctbg tccacgagat cgtcctcgty ggyggwtcya cccgtatccc | 480 |
| ccgtgtccga aagctcatca ccgactactt caacggaaag gagcccaaca agtccatcaa | 540 |
| cccygatgag gctgttgcct acggtgctgc cgtccaggct gccattctct ctggtgacac | 600 |
| cacctccaag tccaccaacg agatcctgct yctcgatgtc gccccsctst ctctcggtat | 660 |
| cgagaccgct ggtggtatga tgaccaagct catccccgc aacaccacca tcccaccaa | 720 |
| gaagtcygag gtcttctcca ccttctccga caaccagcct ggtgtgctca tccaggtcta | 780 |

```
cgagggtgag cgccagcgca ccaaggacaa caacctsctg ggcaagttcg agcttaccgg      840
catcccmcct gctccccgtg gtgttcccca gattgaggtc accttcgacc tsgatgccaa      900
cggtatcatg aacgtctccg ccgtcgagaa gggcaccggc aagaccaaca agattgtcat      960
caccaacgac aagggccgyc tgtccaagga ggagatygag cgcatgcttg cygaggccga     1020
gaagtacaag gaggaggatg aggcygaggs crmccgtgtc tctgccaaga acggcctyga     1080
gtcktacgcc tactccctsc gcaacaccct stccgacycc aaggtcgasg agaagcttga     1140
kgctkccgac aaggagamsc tcamygctga gatyracaag rtygtccagc tggctygayg     1200
asarccagca ggctacymrk gaggagtayg aggagcacca gaaggagcty gaggsyrwkg     1260
cyaaccccat catgatgaar ttctacggag ctgstggtga gggygctccc ggtggcatgc     1320
ccggyryrcc cggtsgtgcc cctggtggct tccctggtgc yggtggcccy gcyccyggyg     1380
ccggyggyga cgatggyccc acygtcgagg aggtcgacta aaywmytygm tacycywrta     1440
mcatcaktcy ckamttstwk wkygrkcaya kmtssrtkkk twtwatgcgg wkkytagtmg     1500
tttkmaygsk mtggrtswga ttasattgtt cmttttctyc wrttttttmtc gtaaygacwt     1560 yacgrwtrkr aaaagtcwmm ggygvtyyat ryacgtggkg rwtgtatwty aattagratc     1620
wtwcawtsrd aamaamarww maaaawaaaa aaaactcgaa actagttctc tctctctctc     1680
ctcgtgc                                                              1687

<210> SEQ ID NO 21
<211> LENGTH: 580
<212> TYPE: DNA
<213> ORGANISM: Artificial
<220> FEATURE:
<223> OTHER INFORMATION: DNA sequence
<220> FEATURE:
<221> NAME/KEY: misc_feature
<222> LOCATION: (1)..(580)
<223> OTHER INFORMATION: consensus sequence for Rho

<400> SEQUENCE: 21
aatccatmac catggctgaa atccgccgaa agctcgtcat tgtcgghgay ggtgcttgtg       60
gtaagacytg tttgttgatt gtcttctcca agggcachtt cccmgaggtc tacgtcccma      120
ccgtcttcga gaactatgtc gccgatgtcg aggtcgatgg caagcacgtc gagctcgcgc      180
tatgggatac bgctggtcag gaggattacg accgtcttcg acctctctca tacccccgact      240 cscacgttat cctgatctgc ttcgccgttg actctcccga ttccctcgay aacgtycagg      300
agaagtggat ctccgaggtc ctscayttct gccagggtct ccctatcatc cttgtcggct      360
gcaagaagga tttgcgayac gaccagaaga ccattgagga gctccacaag accasccaga      420
ascccgtcac cccwgarcag ggtgaagagg tccgcaagaa gattggtgct tacaagtatc      480
ttgagtgctc agccaagacc aatgaaggtg tccgygaggt gttcgagcac gccactcgcg      540
cygctctcct gacgcggaag aagcagaaga agcgcgcaag                            580

<210> SEQ ID NO 22
<211> LENGTH: 411
<212> TYPE: DNA
<213> ORGANISM: Artificial
<220> FEATURE:
<223> OTHER INFORMATION: DNA construct
<220> FEATURE:
<221> NAME/KEY: misc_feature
<223> OTHER INFORMATION: AAC (mitochondrial ADP/ATP carrier)-siRNA
       insert
```

<400> SEQUENCE: 22

```
gtacaaaaaa gcaggcttta aaggaaccaa ttcagtcgac ctcgagcacc tgcgcggccg      60
cgaattcgat atcatttctt gtagacgtcg acgagaccgt tgaactgacg gtcaccaccg     120
gacttggcgt tcttggcatc gttggcaaga cgagtacggg cgtagtccag agagtagacg     180
aagagcagag aagtggcacc agcagcacca ccggaggcaa ggttaccagc catccacatg     240
gcgtagccat ccttgtcctt cttgtagccg aacatcttct tgaacttgtc acggaaagcg     300
aagttcaggg cctgggtggg aagtatcgga tgacgttgg cggtgtttcc tcgccagagg      360
gacatgacac cctcatcgaa atgcccgggc gaattctcta gacccagctt t              411
```

<210> SEQ ID NO 23
<211> LENGTH: 408
<212> TYPE: DNA
<213> ORGANISM: Artificial
<220> FEATURE:
<223> OTHER INFORMATION: DNA construct
<220> FEATURE:
<221> NAME/KEY: misc_feature
<223> OTHER INFORMATION: EF1 (elongation factor 1)-siRNA insert

<400> SEQUENCE: 23

```
gtacaaaaaa gcaggcttta aggaaccaa ttcagtcgac ctcgagcacc tgcgcggccg       60
cgaattcgat atcatttgca ggcaatgtgg gcagtgtggc aatcgaggac gggagcgtaa     120
ccagcaccga cctgaccggg gtggttgagg acgatgacct gggcggtgaa agaagcggca     180
cccatggggg gggtcgttct tggagtcacc agcgacgtta ccacgtcgga tgtccttgac     240
ggaaacgttc ttcacgttga aaccaacgtt gtcaccgggc tgtccctcag tgagctgctc     300
gtggtgcatc tcaacggact tgacttcagt ggtgacgttg aaggagcga aggtaacgac      360
cataccgggc ttgataaatg cccgggcgaa ttctctagac ccagcttt                  408
```

<210> SEQ ID NO 24
<211> LENGTH: 415
<212> TYPE: DNA
<213> ORGANISM: Artificial
<220> FEATURE:
<223> OTHER INFORMATION: DNA construct
<220> FEATURE:
<221> NAME/KEY: misc_feature
<223> OTHER INFORMATION: GA (gamma actin)-siRNA insert

<400> SEQUENCE: 24

```
gtacaaaaaa gcaggcttta aaggaaccaa ttcagtcgac ctcgagcacc tgcgcggccg     60
cgaattcgat atcatttgga agaaggagca agagcagtga tctccttctg catacggtcg    120
gagagaccgg ggtacatggt ggtaccacca gacatgacaa tgtttccgta gagatccttt    180
cggacatcga catcacactt catgatggag ttgaaagtgg tgacgtggat accaccgctc    240
tcaagaccaa ggacagaagg ctggaagaga gcctcaggag cacggaatcg ctcgttacca   300
atggtgataa cctgaccgtc aggaagctcg taagacttct ccaagctgga gctctgggca   360
gcagtctgga tctcctgctc gaaaatgccc gggcgaattc tctagaccca gcttt         415
```

<210> SEQ ID NO 25
<211> LENGTH: 465
<212> TYPE: DNA
<213> ORGANISM: Artificial
<220> FEATURE:
<223> OTHER INFORMATION: DNA construct

```
<220> FEATURE:
<221> NAME/KEY: misc_feature
<223> OTHER INFORMATION: GA-1 (gamma actin 1)-siRNA insert

<400> SEQUENCE: 25
gtacaaaaaa gcaggcttta aaggaaccaa ttcagtcgac ctcgagcacc tgcgcggccg      60
ctaattcgat atcatttgga agaaggagca agagcagtga tctccttctg catacggtcg     120
gagagaccgg ggtacatggt ggtaccacca gactaaagac atgttagaac agttggagtg     180 cttttcgattt gcagaactta ccatgacaat gtttccgtag agatcctttc ggacatcgac    240
atcacacttc atgatggagt tgaaagtggt gacgtggata ccaccgctct caagaccaag     300
gacagaaggc tggaagagag cctcaggagc acggaatcgc tcgttaccaa tggtgataac     360
ctgaccgtca ggaagctcgt aagacttctc caagctggag ctctgggcag cagtctggat     420
ctcctgctcg aaaaatgccc gggcgaattc tctagaccca gcttt                     465

<210> SEQ ID NO 26
<211> LENGTH: 466
<212> TYPE: DNA
<213> ORGANISM: Artificial
<220> FEATURE:
<223> OTHER INFORMATION: DNA construct
<220> FEATURE:
<221> NAME/KEY: misc_feature
<223> OTHER INFORMATION: hsp (heat shock protein chaperone)-siRNA insert

<400> SEQUENCE: 26
gtacaaaaaa gcaggcttta aaggaaccaa ttcagtcgac ctcgagcacc tgcgcggccg      60
cgaattcgat atcatttact tgcccatgag gttgttgtcc ttggtgcgct ggcgctcacc     120
ctcgtagacc tggataagga caccaggctg gttgtcggag aaggtagaga agacctcgga     180
cttcttggtg ggaatggtgg tgttgcgggg gatgagcttg gtcatcatac caccagcggt     240
ctcgataccg agagagaggg gggcgacgtc gaggagcaga atctcgttgg tggccttgct     300
agaggtgtca ccagagagaa tagcagcctg gacagcggca ccgtaggcaa cagcctcatc     360
aggattgatg gacttgttgg gctcctttcc gttgaagtag tcggtgatga gcttctggac     420 acggggata cggaaatgcc cgggcgaatt ctctagaccc agcttt                      466

<210> SEQ ID NO 27
<211> LENGTH: 418
<212> TYPE: DNA
<213> ORGANISM: Artificial
<220> FEATURE:
<223> OTHER INFORMATION: DNA construct
<220> FEATURE:
<221> NAME/KEY: misc_feature
<223> OTHER INFORMATION: Rho (Rho GTPase)-siRNA insert

<400> SEQUENCE: 27
gtacaaaaaa gcaggcttta aaggaaccaa ttcagtcgac ctcgagcacc tgcgcggccg      60
cgaattcgat atcattttgc ttgtggtaaa acctgtttgt tgatcgtttt ctccaagggc     120
actttccccg aggtctacgt ccccaccgtc ttcgagaact atgtcgccga tgtcgaggtt     180
gacggcaagc acgtcgagct cgccctatgg gatactgctg gtcaggagga ttacgaccgt     240
cttcgacctc tctcttaccc cgactccac gttatcttga tctgcttcgc tgttgactct      300
cccgactctc tcgacaacgt ccaggagaag tggatctctg aggttctgca cttctgccag     360
ggkctcccta tcatccttgt cggctaaatg cccgggcgaa ttctctagac ccagcttt       418
```

<210> SEQ ID NO 28
<211> LENGTH: 1024
<212> TYPE: DNA
<213> ORGANISM: Artificial
<220> FEATURE:
<223> OTHER INFORMATION: DNA construct
<220> FEATURE:
<221> NAME/KEY: misc_feature
<223> OTHER INFORMATION: GA_AAC_Rho_siRNA-insert

<400> SEQUENCE: 28

```
gtacaaaaaa gcaggcttta aaggaaccaa ttcagtcgac ctcgagcacc tgcgcggccg      60
cgaattcgat cttgtagacg tcgacgagac cgttgaactg acggtcacca ccggacttgg     120
cgttcttggc atcgttggca agacgagtac gggcgtagtc cagagagtag acgaagagca     180
gagaagtggc accagcagca ccaccggagg caaggttacc agccatccac atggcgtagc     240
catccttgtc cttcttgtag ccgaacatct tcttgaactt gtcacggaaa gcgaagttca     300
gggcctgggt ggggaagtat cggatgacgt tggcggtgtt tcctcgccag agggacatga     360
caccctcatc gatcatttgg aagaaggagc aagagcagtg atctccttct gcatacggtc     420
ggagagaccg gggtacatgg tggtaccacc agacatgaca atgtttccgt agagatcctt     480
tcggacatcg acatcacact tcatgatgga gttgaaagtg gtgacgtgga taccaccgct     540
ctcaagacca aggacagaag gctggaagag agcctcagga gcacggaatc gctcgttacc     600
aatggtgata acctgaccgt caggaagctc gtaagacttc tccaagctgg agctctgggc     660
agcagtctgg atctcctgct cgaaaatgcc ctgcttgtgg taaaacctgt tgttgatcg      720
ttttctccaa gggcactttc cccgaggtct acgtccccac cgtcttcgag aactatgtcg     780
ccgatgtcga ggttgacggc aagcacgtcg agctcgccct atgggatact gctggtcagg     840
aggattacga ccgtcttcga cctctctctt accccgactc ccacgttatc ttgatctgct     900
tcgctgttga ctctcccgac tctctcgaca acgtccagga gaagtggatc tctgaggttc     960
tgcacttctg ccagggkctc cctatcatcc ttgtcggctg ggcgaattct ctagacccag    1020
cttt                                                                 1024
```

<210> SEQ ID NO 29
<211> LENGTH: 1020
<212> TYPE: DNA
<213> ORGANISM: Artificial
<220> FEATURE:
<223> OTHER INFORMATION: DNA construct
<220> FEATURE:
<221> NAME/KEY: misc_feature
<223> OTHER INFORMATION: GA_AAC_mHspCh siRNA-insert

<400> SEQUENCE: 29

```
gtacaaaaaa gcaggcttta aaggaaccaa ttcagtcgac ctcgagcacc tgcgcggccg      60
cgaattcgat cttgtagacg tcgacgagac cgttgaactg acggtcacca ccggacttgg     120
cgttcttggc atcgttggca agacgagtac gggcgtagtc cagagagtag acgaagagca     180
gagaagtggc accagcagca ccaccggagg caaggttacc agccatccac atggcgtagc     240
catccttgtc cttcttgtag ccgaacatct tcttgaactt gtcacggaaa gcgaagttca     300
gggcctgggt ggggaagtat cggatgacgt tggcggtgtt tcctcgccag agggacatga     360
caccctcatc gatcatttgg aagaaggagc aagagcagtg atctccttct gcatacggtc     420
ggagagaccg gggtacatgg tggtaccacc agacatgaca atgtttccgt agagatcctt     480
tcggacatcg acatcacact tcatgatgga gttgaaagtg gtgacgtgga taccaccgct     540
```

```
ctcaagacca aggacagaag gctggaagag agcctcagga gcacggaatc gctcgttacc    600
aatggtgata acctgaccgt caggaagctc gtaagacttc tccaagctgg agctctgggc    660
agcagtctgg atctcctgct cgaaaatgcc cctcaccctc gtagacctgg ataaggacac    720
caggctggtt gtcggagaag gtagagaaga cctcggactt cttggtggga atggtggtgt    780
tgcgggggat gagcttggtc atcataccac cagcggtctc gataccgaga gagaggggg     840 cgacgtcgag gagcagaatc tcgttggtgg ccttgctaga ggtgtcacca gagagaatag    900
cagcctggac agcggcaccg taggcaacag cctcatcagg attgatggac ttgttgggct    960
cctttccgtt gaagtagtcg gtgatgagct tctgggggcg aattctctag acccagcttt   1020
```

<210> SEQ ID NO 30
<211> LENGTH: 1013
<212> TYPE: DNA
<213> ORGANISM: Artificial
<220> FEATURE:
<223> OTHER INFORMATION: DNA construct
<220> FEATURE:
<221> NAME/KEY: misc_feature
<223> OTHER INFORMATION: GA_AAC_EF1 siRNA-insert

<400> SEQUENCE: 30

```
tacaaaaaag caggctttaa aggaaccaat tcagtcgacc tcgagcacct gcgcggccgc     60
gaattcgatc ttgtagacgt cgacgagacc gttgaactga cggtcaccac cggacttggc    120
gttcttggca tcgttggcaa gacgagtacg ggcgtagtcc agagagtaga cgaagagcag    180
agaagtggca ccagcagcac caccggaggc aaggttacca gccatccaca tggcgtagcc    240
atccttgtcc ttcttgtagc cgaacatctt cttgaacttg tcacggaaag cgaagttcag    300
ggcctgggtg gggaagtatc ggatgacgtt ggcggtgttt cctcgccaga gggacatgac    360
accctcatcg atcatttgga agaaggagca agagcagtga tctccttctg catacggtcg    420
gagagaccgg ggtacatggt ggtaccacca gacatgacaa tgtttccgta gagatccttt    480
cggacatcga catcacactt catgatggag ttgaaagtgg tgacgtggat accaccgctc    540
tcaagaccaa ggacagaagg ctggaagaga gcctcaggag cacgaatcg ctcgttacca     600 atggtgataa cctgaccgtc aggaagctcg taagacttct ccaagctgga gctctgggca    660
gcagtctgga tctcctgctc gaaaatgccc gcaggcaatg tgggcagtgt ggcaatcgag    720
gacgggagcg taaccagcac cgacctgacc ggggtggttg aggacgatga cctgggcggt    780
gaaagaagcg gcacccatgg gggggtcgt tcttggagtc accagcgacg ttaccacgtc     840
ggatgtcctt gacggaaacg ttcttcacgt tgaaaccaac gttgtcaccg ggctgtccct    900
cagtgagctg ctcgtggtgc atctcaacgg acttgacttc agtggtgacg ttggaaggag    960
cgaaggtaac gaccataccg ggcttgatgg gcgaattctc tagacccagc ttt          1013
```

<210> SEQ ID NO 31
<211> LENGTH: 1021
<212> TYPE: DNA
<213> ORGANISM: Artificial
<220> FEATURE:
<223> OTHER INFORMATION: DNA construct
<220> FEATURE:
<221> NAME/KEY: misc_feature
<223> OTHER INFORMATION: GA_Rho_EF1 siRNA-insert

<400> SEQUENCE: 31

```
gtacaaaaaa gcaggcttta aaggaaccaa ttcagtcgac ctcgagcacc tgcgcggccg     60
cgaattcgat tcggctgttc ctactatccc tckgggaccg tcttcacgtc ttggagtctc    120
```

```
taggtgaaga ggacctgcaa cagctctctc agccctctca gttgtcgctt cgtctagttc    180
tattgcaccc tcagccccat tctctctcca gcttctgcca gcattaggag gactggtcgt    240
cataggtat cccgctcgag ctgcacgaac ggcagttgga gctgtagccg ctgtatcaag    300
agcttctgcc accctgcat ctggagcccc tttcacggga acctcttttg ctagttgttt    360
gtccaaaatg gtgttcgtat catttggaag aaggagcaag agcagtgatc tccttctgca    420
tacggtcgga gagaccgggg tacatggtgg taccaccaga catgacaatg tttccgtaga    480
gatcctttcg gacatcgaca tcacacttca tgatggagtt gaaagtggtg acgtggatac    540
caccgctctc aagaccaagg acagaaggct ggaagagagc ctcaggagca cggaatcgct    600
cgttaccaat ggtgataacc tgaccgtcag gaagctcgta agacttctcc aagctggagc    660
tctgggcagc agtctggatc tcctgctcga aaatgcccgc aggcaatgtg gcagtgtgg    720
caatcgagga cgggagcgta accagcaccg acctgaccgg ggtggttgag gacgatgacc    780
tgggcggtga agaagcggc acccatgggg ggggtcgttc ttggagtcac cagcgacgtt    840
accacgtcgg atgtccttga cggaaacgtt cttcacgttg aaaccaacgt tgtcaccggg    900
ctgtccctca gtgagctgct cgtggtgcat ctcaacggac ttgacttcag tggtgacgtt    960
ggaaggagcg aaggtaacga ccataccggg cttgatgggc gaattctcta gacccagctt   1020
t                                                                    1021
```

<210> SEQ ID NO 32
<211> LENGTH: 1027
<212> TYPE: DNA
<213> ORGANISM: Artificial
<220> FEATURE:
<223> OTHER INFORMATION: DNA construct
<220> FEATURE:
<221> NAME/KEY: misc_feature
<223> OTHER INFORMATION: GA_Rho_mHspCh siRNA-insert

<400> SEQUENCE: 32

```
gtacaaaaaa gcaggcttta aaggaaccaa ttcagtcgac ctcgagcacc tgcgcggccg     60
cgaattcgat agccgacaag gatgatagg agmccctggc agaagtgcag aacctcagag    120
atccacttct cctggacgtt gtcgagagag tcgggagagt caacagcgaa gcagatcaag    180
ataacgtggg agtcggggta agagagaggt cgaagacggt cgtaatcctc ctgaccagca    240
gtatcccata gggcgagctc gacgtgcttg ccgtcaacct cgacatcggc gacatagttc    300
tcgaagacgg tggggacgta gacctcgggg aaagtgccct tggagaaaac gatcaacaaa    360
caggttttac cacaagcaat catttggaag aaggagcaag agcagtgatc tccttctgca    420
tacggtcgga gagaccgggg tacatggtgg taccaccaga catgacaatg tttccgtaga    480
gatcctttcg gacatcgaca tcacacttca tgatggagtt gaaagtggtg acgtggatac    540
caccgctctc aagaccaagg acagaaggct ggaagagagc ctcaggagca cggaatcgct    600
cgttaccaat ggtgataacc tgaccgtcag gaagctcgta agacttctcc aagctggagc    660
tctgggcagc agtctggatc tcctgctcga aaatgcccct caccctcgta gacctggata    720
aggacaccag gctggttgtc ggagaaggta gagaagacct cggacttctt ggtgggaatg    780
gtggtgttgc gggggatgag cttggtcatc ataccaccag cggtctcgat accgagagag    840
aggggggcga cgtcgaggag cagaatctcg ttggtgcct tgctagaggt gtcaccagag    900
agaatagcag cctggacagc ggcaccgtag gcaacagcct catcaggatt gatggacttg    960
```
ttgggctcct ttccgttgaa gtagtcggtg atgagcttct gggggcgaat tctctagacc    1020
cagctttt    1027

<210> SEQ ID NO 33
<211> LENGTH: 1017
<212> TYPE: DNA
<213> ORGANISM: Artificial
<220> FEATURE:
<223> OTHER INFORMATION: DNA construct
<220> FEATURE:
<221> NAME/KEY: misc_feature
<223> OTHER INFORMATION: AAC_Rho_EF1 siRNA-insert

<400> SEQUENCE: 33
gtacaaaaaa gcaggcttta aggaaccaa ttcagtcgac ctcgagcacc tgcgcggccg    60
cgaattcgat tgcttgtggt aaaacctgtt tgttgatcgt tttctccaag ggcactttcc    120
ccgaggtcta cgtccccacc gtcttcgaga actatgtcgc cgatgtcgag gttgacggca    180
agcacgtcga gctcgcccta tgggatactg ctggtcagga ggattacgac cgtcttcgac    240
ctctctctta ccccgactcc cacgttatct tgatctgctt cgctgttgac tctcccgact    300
ctctcgacaa cgtccaggag aagtggatct ctgaggttct gcacttctgc cagggkctcc    360
ctatcatcct tgtcggctat catttcttgt agacgtcgac gagaccgttg aactgacggt    420
caccaccgga cttggcgttc ttggcatcgt tggcaagacg agtacgggcg tagtccagag    480
agtagacgaa gagcagagaa gtggcaccag cagcaccacc ggaggcaagg ttaccagcca    540
tccacatggc gtagccatcc ttgtccttct tgtagccgaa catcttcttg aacttgtcac    600
ggaaagcgaa gttcagggcc tgggtgggga agtatcggat gacgttggcg gtgtttcctc    660
gccagaggga catgacaccc tcatcgaaat gcccatcaag cccggtatgg tcgttacctt    720
cgctccttcc aacgtcacca ctgaagtcaa gtccgttgag atgcaccacg agcagctcac    780
tgagggacag cccggtgaca cgttggtttt caacgtgaag aacgtttccg tcaaggacat    840
ccgacgtggt aacgtcgctg gtgactccaa gaacgacccc cccatgggt gccgcttctt    900 tcaccgccca ggtcatcgtc ctcaaccacc ccggtcaggt cggtgctggt tacgctcccg    960
tcctcgattg ccacactgcc acattgcct gcgggcgaat tctctagacc cagctttt    1017

<210> SEQ ID NO 34
<211> LENGTH: 1073
<212> TYPE: DNA
<213> ORGANISM: Artificial
<220> FEATURE:
<223> OTHER INFORMATION: DNA construct
<220> FEATURE:
<221> NAME/KEY: misc_feature
<223> OTHER INFORMATION: AAC_GA-1_Rho siRNA-insert

<400> SEQUENCE: 34
gtacaaaaaa gcaggcttta aggaaccaa ttcagtcgac ctcgagcacc tgcgcggccg    60
cgaattcgat cttgtagacg tcgacagagac cgttgaactg acggtcacca ccggacttgg    120
cgttcttggc atcgttggca agacgagtac gggcgtagtc cagagagtag acgaagagca    180
gagaagtggc accagcagca ccaccggagg caaggttacc agccatccac atggcgtagc    240
catccttgtc cttcttgtag ccgaacatct tcttgaactt gtcacggaaa gcgaagttca    300
gggcctgggt ggggaagtat cggatgacgt tggcggtgtt tcctcgccag agggacatga    360 cacccctcatc gatcatttgg aagaaggagc aagagcagtg atctccttct gcatacggtc    420
ggagagaccg gggtacatgg tggtaccacc agactaaaga catgttagaa cagttggagt    480

| | |
|---|---|
| gctttcgatt tgcagaactt accatgacaa tgtttccgta gagatccttt cggacatcga | 540 |
| catcacactt catgatggag ttgaaagtgg tgacgtggat accaccgctc tcaagaccaa | 600 |
| ggacagaagg ctggaagaga gcctcaggag cacggaatcg ctcgttacca atggtgataa | 660 |
| cctgaccgtc aggaagctcg taagacttct ccaagctgga gctctgggca gcagtctgga | 720 |
| tctcctgctc gaaaatgccc tgcttgtggt aaaacctgtt tgttgatcgt tttctccaag | 780 |
| ggcactttcc ccgaggtcta cgtccccacc gtcttcgaga actatgtcgc cgatgtcgag | 840 |
| gttgacggca agcacgtcga gctcgcccta tgggatactg ctggtcagga ggattacgac | 900 |
| cgtcttcgac ctctctctta ccccgactcc acgttatct tgatctgctt cgctgttgac | 960 |
| tctcccgact ctctcgacaa cgtccaggag aagtggatct ctgaggttct gcacttctgc | 1020 |
| cagggkctcc ctatcatcct tgtcggctgg gcgaattctc tagacccagc ttt | 1073 |

<210> SEQ ID NO 35
<211> LENGTH: 1061
<212> TYPE: DNA
<213> ORGANISM: Artificial
<220> FEATURE:
<223> OTHER INFORMATION: DNA construct
<220> FEATURE:
<221> NAME/KEY: misc_feature
<223> OTHER INFORMATION: AAC_GA-1_mHspCh siRNA-insert

<400> SEQUENCE: 35

| | |
|---|---|
| gtacaaaaaa gcaggcttta aaggaaccaa ttcagtcgac ctcgagcacc tgcgcggccg | 60 |
| ctaattcgat tgtagacgtc gacgagaccg ttgaactgac ggtcaccacc ggacttggcg | 120 |
| ttcttggcat cgttggcaag acgagtacgg gcgtagtcca gagagtagac gaatagaaga | 180 |
| gaagtggcac cagcagcacc accggaggca aggttaccgg ccatccacat ggcgtagcca | 240 |
| tccttgtcct tcttgtaacc gaacatcttc ttgaacttgt cacggaaagc gaagttcaga | 300 |
| gcctgggtag ggaagtatcg gatgacgttg gcggtgtttc ctcgccagag ggacatgaca | 360 |
| ccctcatcga tcatttggaa gaaggagcaa gagcagtgat ctccttctgc atacggtcgg | 420 |
| agagaccggg gtacatggtg gtaccaccag actaaagaca tgttagaaca gttggagtgc | 480 |
| tttcgatttg cagaacttac catgacaatg tttccgtaga gatcctttcg gacatcgaca | 540 |
| tcacacttca tgatggagtt gaaagtggtg acgtggatac caccgctctc aagaccaagg | 600 |
| acagaaggct ggaagagagc ctcaggagca cggaatcgct cgttaccaat ggtgataacc | 660 |
| tgaccgtcag gaagctcgta agacttctcc aagctggagc tctgggcagc agtctggatc | 720 |
| tcctgctcga aaatgccct cgtagacctg ataaggaca ccaggctggt tgtcggagaa | 780 |
| agtagagaag acctcggact tcttggtggg aatggtggtg ttgcggggga tgagcttggt | 840 |
| catcatacca ccagcggtct cgataccgag agagagaggg gcaacgtcga ggagcagaat | 900 |
| ctcgttggtg gccttgctag aggtgtcacc agagagaata gcagcctgga cagcggcacc | 960 |
| gtaggcaaca gcctcatcag ggttgatgga cttgttgggc tcctttccgt tgaagtagtc | 1020 |
| ggtgatgagc ttctgggggc gaattctcta gacccagctt t | 1061 |

<210> SEQ ID NO 36
<211> LENGTH: 1058
<212> TYPE: DNA
<213> ORGANISM: Artificial
<220> FEATURE:
<223> OTHER INFORMATION: DNA construct
<220> FEATURE:
<221> NAME/KEY: misc_feature
<223> OTHER INFORMATION: AAC_GA-1_EF1 siRNA-insert

<400> SEQUENCE: 36

```
gtacaaaaaa gcaggcttta aaggaaccaa ttcagtcgac ctcgagcacc tgcgcggccg      60
ctaattcgat tgtagacgtc gacgagaccg ttgaactgac ggtcaccacc ggacttggcg     120
ttcttggcat cgttggcaag acgagtacgg gcgtagtcca gagagtagac gaatagaaga     180
gaagtggcac cagcagcacc accggaggca aggttaccgg ccatccacat ggcgtagcca     240
tccttgtcct tcttgtaacc gaacatcttc ttgaacttgt cacggaaagc gaagttcaga     300
gcctgggtag ggaagtatcg gatgacgttg gcggtgtttc ctcgccagag ggacatgaca     360
ccctcatcga tcatttggaa gaaggagcaa gagcagtgat ctccttctgc atacggtcgg     420
agagaccggg gtacatggtg gtaccaccag actaaagaca tgttagaaca gttggagtgc     480
tttcgatttg cagaacttac catgacaatg tttccgtaga gatcctttcg gacatcgaca     540
tcacacttca tgatggagtt gaaagtggtg acgtggatac caccgctctc aagaccaagg     600
acagaaggct ggaagagagc ctcaggagca cggaatcgct cgttaccaat ggtgataacc     660
tgaccgtcag gaagctcgta agacttctcc aagctggagc tctgggcagc agtctggatc     720
tcctgctcga aaaatgcccg caggcaatgt gggcagtgtg gcaatcgagg acgggagcgt     780
aaccagcacc gacctgaccg gggtggttga ggacgatgac ctgggcggtg aaagaagcgg     840
cacccatggg ggggtcgttc ttggagtcac cagcgacgtt accacgtcgg atgtccttga     900
cggaaacgtt cttcacgttg aaaccaacgt tgtcaccggg ctggccctca gtgagctgct     960
cgtggtgcat ctcaacggac ttgacttcag tggtgacgtt ggaaggagcg aaggtaacga    1020
ccataccggg cttgatggaa ttctctagac ccagcttt                             1058
```

<210> SEQ ID NO 37
<211> LENGTH: 1070
<212> TYPE: DNA
<213> ORGANISM: Artificial
<220> FEATURE:
<223> OTHER INFORMATION: DNA construct
<220> FEATURE:
<221> NAME/KEY: misc_feature
<223> OTHER INFORMATION: Rho_GA-1_EF1 siRNA-insert

<400> SEQUENCE: 37

```
gtacaaaaaa gcaggcttta aaggaaccaa ttcagtcgac ctcgagcacc tgcgcggccg      60
cgaattcgat tgcttgtggt aaaacctgtt tgttgatcgt tttctccaag ggcactttcc     120
ccgaggtcta cgtccccacc gtcttcgaga actatgtcgc cgatgtcgag gttgacggca     180
agcacgtcga gctcgcccta tgggatactg ctggtcagga ggattacgac cgtcttcgac     240
ctctctctta ccccgactcc cacgttatct tgatctgctt cgctgttgac ctcccgact      300
ctctcgacaa cgtccaggag aagtggatct ctgaggttct gcacttctgc cagggkctcc     360
ctatcatcct tgtcggctat catttggaag aaggagcaag agcagtgatc tccttctgca     420
tacggtcgga gagaccgggg tacatggtgg taccaccaga ctaaagacat gttagaacag     480
ttggagtgct ttcgatttgc agaacttacc atgacaatgt ttccgtagag atcctttcgg     540
acatcgacat cacacttcat gatggagttg aaagtggtga cgtggatacc accgctctca     600
agaccaagga cagaaggctg aagagagcc tcaggagcac ggaatcgctc gttaccaatg     660
gtgataacct gaccgtcagg aagctcgtaa gacttctcca agctggagct ctgggcagca     720
gtctggatct cctgctcgaa aatgcccgca ggcaatgtgg gcagtgtggc aatcgaggac     780
gggagcgtaa ccagcaccga cctgaccggg gtggttgagg acgatgacct gggcggtgaa     840
```

```
agaagcggca cccatggggg gggtcgttct tggagtcacc agcgacgtta ccacgtcgga      900
tgtccttgac ggaaacgttc ttcacgttga accaacgtt gtcaccgggc tgtccctcag       960
tgagctgctc gtggtgcatc tcaacggact tgacttcagt ggtgacgttg aaggagcga      1020 aggtaacgac cataccgggc ttgatgggcg aattctctag acccagcttt               1070
```

<210> SEQ ID NO 38
<211> LENGTH: 1077
<212> TYPE: DNA
<213> ORGANISM: Artificial
<220> FEATURE:
<223> OTHER INFORMATION: DNA construct
<220> FEATURE:
<221> NAME/KEY: misc_feature
<223> OTHER INFORMATION: Rho_GA-1_mHspCh siRNA-insert

<400> SEQUENCE: 38

```
gtacaaaaaa gcaggcttta aaggaaccaa ttcagtcgac ctcgagcacc tgcgcggccg       60
ctaattcgat cagccgacaa ggatgatagg gagaccctgg cagaagtgca gaacctcaga      120
gatccacttc tcctgaacgt tgtcgaggga gtcgggagag tcaacggcga agcagatcaa      180
gataacgtgg gagtcggggt aagaaagagg tcgaagacgg tcgtaatcct cctgaccagc      240
agtatcccat agggcgagct cgacgtgctt gccgtcaacc tcgacatcgg caacatagtt      300
ctcgaagacg gtggggacgt aaacctcggg aaagtgccct ggagaaaaac aatcaacaaa      360
caggttttac cacaagcacc atcgatcatt tggaagaagg agcaagagca gtgatctcct      420
tctgcatacg gtcggagaga ccggggtaca tggtggtacc accagactaa agacatgtta      480
gaacagttgg agtgctttcg atttgcagaa cttaccatga caatgtttcc gtagagatcc      540
tttcggacat cgacatcaca cttcatgatg gagttgaaag tggtgacgtg gataccaccg      600
ctctcaagac caaggacaga aggctggaag agagcctcag gagcacggaa tcgctcgtta      660
ccaatggtga taacctgacc gtcaggaagc tcgtaagact tctccaagct ggagctctgg      720
gcagcagtct ggatctcctg ctcgaaaaat tgccctcgta gacctggata aggacaccag      780
gctgggtgtc ggagaaggta gagaagacct cggacttctt ggtgggaatg gtggtgttgc      840 ggggatgag cttggtcatc ataccaccag cggtctcgat accgagagag agaggggcaa      900
cgtcgaggag cagaatctcg ttggtggtct tgctagaggt gtcaccagag agaatagcag      960 cctgacagc ggcaccgtag gcaacagcct catcagggtt gatggacttg ttgggctcct     1020
ttccgttgaa gtagtcggtg atgagcttct gggggcgaat tctctagacc cagcttt        1077
```

<210> SEQ ID NO 39
<211> LENGTH: 1019
<212> TYPE: DNA
<213> ORGANISM: Artificial
<220> FEATURE:
<223> OTHER INFORMATION: DNA construct
<220> FEATURE:
<221> NAME/KEY: misc_feature
<223> OTHER INFORMATION: Rho_AAC_EF1 siRNA-insert

<400> SEQUENCE: 39

```
gtacaaaaaa gcaggcttta aaggaaccaa ttcagtcgac ctcgagcacc tgcgcggccg       60
ctaattcgat cgatggtgct tgtggtaaaa cctgtttgtt gattgttttc tccaagggca      120
ctttccccga ggtttacgtc cccaccgtct tcgagaacta tgttgccgat gtcgaggttg      180
acggcaagca cgtcgagctc gccctatggg atactgctgg tcaggaggat tacgaccgtc      240
ttcgacctct ttcttacccc gaatctcaag ttatcttgat ttgcttcgcc gttgactctt      300
```

```
ccgactccct cgacaacgtt caggagaagt ggatctgtga ggttctgcac ttctgccagg    360
gtctccctat catccttgtc ggctgatcat ttttgtagac gtcgacgaga ccgttgaact    420
gacggtcacc accggacttg gcgttcttgg catcgttggc aagacgagta cgggcgtagt    480
ccagagagta gacgaataga agagaagtgg caccagcagc accaccggag gcaaggttac    540
cggccatcca catggcgtag ccatccttgt ccttcttgta accgaacatc ttcttgaact    600
tgtcacggaa agcgaagttc agagcctggg tagggaagta tcggatgacg ttggcggtgt    660
ttcctcgcca gagggacatg acaccctcat aaatgcccat caagcccggt atggtcgtta    720
ccttcgctcc ttccaacgtc accactgaag tcaagtccgt tgagatgcac cacgagcagc    780
tcactgaggg ccagcccggt gacaacgttg gtttcaacgt gaagaacgtt tccgtcaagg    840
acatccgacg tggtaacgtc gctggtgact ccaagaacga ccccccatg ggtgccgctt    900 cttttcaccgc ccaggtcatc gtcctcaacc accccggtca ggtcggtgct ggttacgctc    960
ccgtcctcga ttgccacact gcccacattg cctgggcga attctctaga cccagcttt    1019
```

METHOD FOR CREATING BROAD-SPECTRUM RESISTANCE TO FUNGI IN TRANSGENIC PLANTS

CROSS-REFERENCE TO RELATED APPLICATIONS

The present application is a U.S. National Stage entry under 35 U.S.C. §371 of International Application No. PCT/EP2009/001805, filed Mar. 12, 2009, designating the United States of America and published in German on Sep. 17, 2009, which in turn claims priority to European Patent Application No. DE 10 2008 014 041.4 filed Mar. 13, 2008, each of which is incorporated herein by reference in its entirety.

The invention relates to a method for creating broad-spectrum resistance to fungi in transgenic plants, characterized in that a recombinant nucleic acid molecule, comprising at least one nucleic acid sequence, is introduced into the plant, wherein the nucleic acid sequence is identical to and/or complementary to one or more of the nucleic acids selected from SEQ ID NOs: 1-16 and/or a part thereof, or has a sequence identity of at least 85% to one or more of the nucleic acids, selected from SEQ ID NOs: 1-16, and is transcribed in the plant, so that in case of an infection of the plant with a fungus the nucleic acid sequence or parts thereof interact with one or more of the corresponding and/or complementary nucleic acids of the fungus, such that the expression of the fungal nucleic acid sequence is substantially inhibited.

The invention also relates to the nucleic acid molecule according to the invention, and to plants containing said nucleic acid molecule according to the invention.

The present invention relates to creating broad-spectrum resistance in transgenic plants by introducing inhibitory nucleic acid sequences inhibiting the expression of fungal genes.

The nucleic acid sequences of genes which are crucial to development, growth and propagation of fungi, i.e. sequences of genes with an essential function in fungi, are often conserved and/or have a high sequence identity. Regions having a particularly high sequence identity between various fungi are used in order to produce inhibitory gene constructs, e.g. on basis of antisense, siRNA, shRNA, ribozyme technology and other technologies imparting the inhibition of the expression and activation of genes. Since said methods are based on the sequence-specific hybridization of the inhibitory RNA molecules with corresponding target sequences in certain fungal genes, the expression of all corresponding genes from various fungi is thus inhibited as well. On the basis of the high sequence identity of such conserved gene sections, transgenic plants are produced, which have broad-spectrum resistance to various fungi.

Plant diseases, which are caused by various pathogens, such as viruses, bacteria and fungi, may lead to significant crop failure in the cultivation of cultivated plants, resulting in economic consequences and in threatening human food supply. Thus, infestation of cereals by *Blumeria graminis*, the pathogen that causes powdery mildrew, may cause losses of yield of up to 30%.

Since the last century, chemical fungicides have been utilised for controlling fungal diseases. Using these substances has reduced the extent of plant diseases, however, it cannot be excluded to this day that these compounds have adverse effects on humans, animals and the environment. In order to reduce the usage of conventional pesticides to a minimum in the long run, it is important to examine the natural pathogen defence of various plants towards different pathogens and to use the same specifically for the production of pathogen-resistant plants by genetechnological manipulation, e.g. by means of introducing external resistance genes or by means of the manipulation of the endogenous gene expression of the plants.

Resistance is the ability of a plant to inhibit any infestation or population of a pest or at least to limit the same. The plants have a certain degree of natural resistance which is imparted by the formation of specific defence substances, such as isoprenoids, flavonoids, enzymes and reactive oxygen species.

One approach for producing resistant plants is the expression of a plant transgene in said plants, resulting in the formation of said specific defence substances. In this way, chitinase (WO 92/17591) and pathogenesis-related genes (WO 92/20800) as well as genes for various oxidizing enzymes, such as glucose oxidase (WO 95/21924) and oxalate oxidase (WO 99/04013), have already been overexpressed in plants, thus creating plants having increased fungal resistance.

Conversely, it could be shown that it is some of the plant genes that enable the fungus to enter the plant. Thus, an alternative approach for producing transgenic plants having increased fungal resistance is to inhibit the expression of said plant genes in transgenic plants, which code for example for a polyphenoloxidase (WO 02/061101), NADPH-oxidase (WO 2004/009820) and the Mlo-gene (WO 00/01722).

Another alternative for causing resistance to pathogenic fungi is to introduce gene constructs in plants which inhibit the expression and/or activity of fungal genes that are essential for the proliferation and/or development of fungi (US Patent No. 2007/0061918).

To date, resistance strategies against all fungal pathogens are not available. This is particularly serious, since virtually every agricultural crop may be attacked by a plurality of pathogenic fungi. Thus, there is an urgent need for strategies to confer resistance to a plant against a plurality of potential pathogenic fungi at the same time.

It is thus an object of the present invention to provide a method for producing transgenic plants having broad-spectrum resistance to various fungal pathogens.

The features of the independent claims are to solve said and further objects as resulting from the specification.

Preferred embodiments of the present invention are defined by the features of the subclaims.

One aspect of the present invention relates to a method for creating broad-spectrum resistance to fungi in transgenic plants,
characterized in that a recombinant nucleic acid molecule comprising at least one nucleic acid sequence is introduced in the plant, wherein the nucleic acid sequence
  a) is identical and/or complementary to one or more of the nucleic acids selected from SEQ ID NOs: 1-5 and/or a part thereof, or has a sequence identity of at least 85% to one or more of the nucleic acids selected from SEQ ID NOs: 1-5, and/or
  b) is identical and/or complementary to one or more of the nucleic acids selected from SEQ ID NOs: 6-11 and/or a part thereof, or has a sequence identity of at least 85% to one or more of the nucleic acids selected from SEQ ID NOs: 6-11, or
  c) is identical and/or complementary to one or more of the nucleic acids selected from SEQ ID NOs: 12-16 and/or a part thereof, or has a sequence identity of at least 85% to one or more of the nucleic acids selected from SEQ ID NOs: 12-16,
  and is transcribed in the plant, so that in case of an infection of the plant with a fungus, the nucleic acid sequence or parts thereof interacts with one or more of the corresponding and/or complementary nucleic acids of the fungus such that the expression of the fungal nucleic acid sequence is substantially inhibited.

In the sense of the present invention, "sequence identity" denotes the degree of conformity with regard to the 5'-3' sequence within a sequence of nucleotide units within a nucleic acid molecule in comparison to another nucleic acid molecule. The sequence identity is determined using a series of programs, which base on various algorithms, such as BLASTN, ScanProsite, the laser gene software, etc. As an alternative, the BLAST program package of the National Center for Biotechnology Information (<http colon slash slash>www <dot>ncbi <dot>nlm <dot>nih <dot>gov) may be used. Here, in addition, the program Sequencher (Gene Codes Corp., Ann Arbor, MI, USA) using the "dirtydata"-algorithm for sequence comparisons was employed.

In a preferred embodiment, the at least one nucleic acid sequence introduced in the plant is at least 50%, preferably at least 60%, also preferably at least 70%, particularly preferably at least 80%, in particular preferably 90, 92 or 94%, and most preferably to at least 96, 98 or 99% or 100% identical to a nucleic acid sequence from fungi.

In another preferred embodiment, the at least one nucleic acid sequence introduced in the plant is at least 50%, preferably at least 60%, also preferably at least 70%, particularly preferably at least 80%, in particular preferably 90, 92 or 94%, and most preferably at least 96, 98 or 99% or 100% identical to a nucleic acid sequence essential for the fungus.

A "nucleic acid sequence essential for the fungus" in the sense of the present invention, is a nucleic acid sequence which is crucial to the development, growth and propagation of fungi, so that inhibiting the expression of said nucleic acid leads to the death of the fungus and/or stops the propagartion and/or development of the fungus.

In a preferred embodiment of the method according to the invention, conserved sections within essential fungal nucleic acid sequences are used as target sequences for the reduction of the expression level of the corresponding fungal nucleic acid sequence, according to the invention.

A "corresponding" nucleic acid sequence, in the sense of the present invention, is synonymous with a homologous nucleic acid sequence, i.e. a nucleic acid sequence from a fungal species having identical or almost identical biological function, and usually also a high or very high sequence identity. Corresponding fungal nucleic acid sequences are, according to the invention, at least 50%, preferably at least 60%, also preferably at least 70%, particularly preferably at least 80%, in particular preferably 85, 90, 92 or 94%, and most preferably at least 96, 98 or 99% or 100% identical to a nucleic acid sequence from another fungus.

The term "conserved sections" or target sequences relates to the high identity of nucleic acid sequences, usually the DNA sequence of a gene, or the RNA sequence transcribed therefrom and/or mRNA sequence, upon comparison of organisms which are evolutionary closely related. Within the scope of the present invention, regions are considered suitable conserved gene sections, in which due to a sequence comparison with the genome of other fungal species there is the possibility that the reduction of the expression level of the underlying fungal gene will lead to a resistance to said fungus but also possibly to further fungi.

The inventors were able to determine conserved sections in essential fungal genes by means of sequence comparisons. These were used as target sequences in order to derive corresponding RNAi constructs which create broad-spectrum resistance to fungi in transgenic plants. The essential genes are a) the mitochondrial ADP/ATP translocator (AAC)
b) the elongation factor 1 (EF1)
c) gamma-actin (GA)
d) the mitochondrial heat shock protein 70 (Hsp)
e) the Rho-GTPase (Rho).

Using the RNAi constructs derived from the corresponding gene sequences of *Fusarium culmorum* the inventors were able to create resistance in barley to both, *Fusarium culmorum* and *Blumeria graminis*.

Thereby, it was ensured that the corresponding gene sections or a sequence homologous thereto are not endogenous to the plant to be used, as otherwise endogenous processes in the plant may be inhibited as well, which is not desired.

In a preferred embodiment of the method of the present invention, the nucleic acid sequence of the present invention comprises conserved sections within essential fungal genes as target sequences for the reduction of the expression level of the corresponding fungal nucleic acid sequence, according to the invention.

In another preferred embodiment, the at least one nucleic acid sequence of the present invention has, in comparison with corresponding nucleic acid sequences or target sequences in nucleic acid sequences from fungi and especially preferably from pathogenic fungi, over a range of at least 100 bp, preferably 150 bp, preferably 200 bp, especially preferably 250 bp and also especially preferably 300 bp a sequence identity of at least 85%; at least 90% or at least 95%.

In another preferred embodiment, the at least one nucleic acid sequence of the present invention has, in comparison with corresponding nucleic acid sequences from plants, over a "sliding window" of 100 bp a sequence identity of maximal 80%, preferably 75% and most preferably maximal 70%.

A "sliding window", in the sense of the present invention, is a nucleotide sequence with a length of 100 bp, which is randomly relocatable within a given nucleotide sequence.

In an especially preferred embodiment of the method of the present invention, the corresponding and/or complementary nucleic acid of the fungus, the expression of which is basically inhibited by the nucleic acid sequence of the present invention, is a) the mitochondrial ADP/ATP translocator (AAC)
b) the elongation factor 1 (EF1)
c) gamma-actin (GA)
d) the mitochondrial heat shock protein 70 (Hsp)
e) the Rho-GTPase (Rho).

The term "resistance" stands for minimizing or reducing symptoms of disease of a plant due to an infestation by pests and/or pathogens, and preferably by a fungus and especially preferably by several fungi. Said symptoms may be diverse, however, they preferably comprise symptoms that directly or indirectly impair the quality of the plant, the quantity of the yield, the suitability for use as feed or food, or which impede sowing, cultivating, harvesting or processing the harvest. Furthermore, "resistance" also means that pests and/or a pathogen and preferably a fungus and especially preferably several fungi display reduced growth in a plant and reduced or absent propagation. The term "resistance" also includes a so-called transient resistance, i.e. the transgenic plants or plant cells of the present invention have an increased resistance to pests and/or pathogens or fungi only for a limited period of time, compared to the corresponding wild type.

The term "broad-spectrum resistance" according to the invention denotes that the transgenic plants or plant cells of the present invention are infected or attacked less strongly and/or less frequently by more than one fungal species in comparison with non-transformed wild type plants or plant cells, which were—apart from that—treated in the same manner (e.g. climate and cultivation conditions, fungal species, etc.). Preferably, the attack by at least one fungus, by at least two different fungi, especially preferably by at least three different fungi, particularly preferably by at least four different fungi, and most preferably by at least five different fungi is reduced, which results in reducing the formation of disease symptoms. Such fungal resistance may be experimentally proven inter alia by a reduction of haustoria formation and/or hyphen growth.

"Substantially inhibited" in the scope of the present invention means that the expression level of the nucleic acid sequence of the fungus in the transgenic plants is reduced to a level, at which the plants show an increased resistance to fungal infection and/or show signs of recovery after initial symptoms of a fungal infection. "Transgenic plants having broad-spectrum resistance" are plants according to the invention which show few symptoms of a fungal infection, however, said symptoms are relatively weak so that the usability and applicability of the infested plant is not questioned. Plants of the present invention show a phenotype which is substantially unchanged compared to wild type plants, i.e. the use as agricultural crop, food plant or feed plant, etc., is not questioned.

If, in the scope of the present invention, nucleic acid sequences are mentioned, which code for fungal genes or parts thereof, then both the complete coding DNA sequence of the respective fungal gene as well as the complete mRNA sequence or the respective sections thereof are meant.

The expression level of the nucleic acid of the fungus, the expression of which is substantially inhibited by the nucleic acid transcribed in the transgenic plant, may be determined in the infested wild type plants as well as in the transgenic plants, for example, by RT-PCR analysis or Northern Blot analysis with specific primers or probes. A person skilled in the art knows how to select said probes or primers in order to examine the expression of the nucleic acid of the fungus. Preferably, the expression level of the nucleic acid of the fungus is statistically significantly reduced by at least 80%, particularly preferably by at least 90%, also particularly preferably by at least 95%, and most preferably by at least 98% or 99%.

In another preferred embodiment of the method of the present invention, the at least one nucleic acid sequence comprises at least 19 nucleotides, at least 20 nucleotides, at least 21 nucleotides, at least 22 nucleotides, at least 23 nucleotides, at least 24 nucleotides, at least 25 nucleotides or at least 50 nucleotides.

In another preferred embodiment of the method of the present invention, the at least one nucleic acid sequence comprises at least 50 nucleotides, at least 100 nucleotides, at least 150 nucleotides, at least 200 nucleotides, at least 250 nucleotides, at least 300 nucleotides, at least 400 nucleotides or at least 500 nucleotides.

In a preferred embodiment, the at least one nucleic acid sequence of the present invention comprises at least 19 nucleotides, at least 20 nucleotides, at least 21 nucleotides, at least 22 nucleotides, at least 23 nucleotides, at least 24 nucleotides, at least 25 nucleotides or at least 50 nucleotides having a sequence identity of at least 40%, preferably at least 50%, further preferably at least 60%, also preferably at least 70% and/or 75%, especially preferably at least 80%, 82%, 84%, 86% and/or 88%, in particular preferably at least 90%, 92% and/or 94%, and most preferably at least 95%, 96%, 97%, 98% and/or 99% compared to another nucleic acid sequence, wherein the nucleic acid sequence is preferably derived from fungi.

In another preferred embodiment, the at least one nucleic acid sequence of the present invention comprises at least 50 nucleotides, at least 100 nucleotides, at least 150 nucleotides, at least 200 nucleotides, at least 250 nucleotides, at least 300 nucleotides, at least 400 nucleotides or at least 500 nucleotides having a sequence identity of at least 40%, preferably at least 50%, further preferably at least 60%, also preferably at least 70% and/or 75%, especially preferably at least 80%, 82%, 84%, 86% and/or 88%, in particular preferably at least 90%, 92% and/or 94%, and most preferably at least 95%, 96%, 97%, 98% and/or 99% compared to another nucleic acid sequence, wherein the nucleic acid sequence is preferably derived from fungi.

In the sense of the present invention, the term "identical" relates to the degree of sequence identity of a nucleic acid sequence compared to another nucleic acid sequence. Identical nucleic acid sequences, in the sense of the present invention have a sequence identity of at least 40%, at least 50%, at least 60%, preferably at least 70%, especially preferably at least 80%, also especially preferably at least 90%, in particular preferably at least 95% and most preferably at least 98 or 100% compared to another nucleic acid sequence.

The term "complementary" means the ability of a nucleic acid sequence to hybridize with another nucleic acid sequence due to hydrogen bridges between complementary bases. The skilled person knows that two nucleic acid molecules do not need to have a 100% complementarity in order to hybridize with each other. Preferably, a nucleic acid sequence, which is to hybridizes with another nucleic acid sequence, is least 40%, at least 50%, at least 60%, at least 70%, especially preferably at least 80%, also especially preferably at least 90%, in particular preferably to at least 95% and most preferably at least 98 or 100% complementary to said nucleic acid sequence.

According to the invention, the "recombinant nucleic acid molecule" stands for all vectors, plasmids, cosmids, viruses and other vectors common in genetic engineering, for the transfer/introduction of nucleic acid molecules in plants or plant cells.

A high number of cloning vectors is available for preparing the introduction of foreign genes in higher plants or the cells thereof, which contain a replication signal for *E. coli* and a marker gene for selecting transformed bacteria cells. Examples of such vectors are pBR322, pUC-series, M13 mp-series, pACYC184 etc. The desired sequence may be inserted into the vector at a suitable restriction site. The resulting plasmid is used for the transformation of *E. coli* cells. Transformed *E. coli* cells are cultivated in a suitable medium and subsequently harvested and lysed. The plasmid is regained. Analysis methods for characterizing the regained plasmid DNA generally comprise restriction analyses, gel electrophoreses, and other biochemical-molecular biological methods. After each manipulation, the plasmid DNA can be cleaved, and regained DNA fragments can be linked to other DNA sequences. Each plasmid DNA sequence may be cloned into the same or other plasmids. Standard methods for cloning may be taken from Sambrook et al., 2001 (Molecular cloning: A laboratory manual, 3rd edition, Cold Spring Harbor Laboratory Press).

In the method of the invention for producing transgenic plants having broad-spectrum resistance to fungi, the characteristic of the at least one nucleic acid sequence to impart the suppression of the expression of a nucleic acid sequence of a fungus may also make the plant resistant to all other fungi which are comprising the respective highly conserved region in said gene. As discussed below, said methods for suppressing the expression of a nucleic acid sequence are based on specific complementary base pairing of inhibitory nucleic acid molecules with sequences of a fungal cellular nucleic acid molecule. Due to the high sequence identity of conserved regions in one or more essential genes of various fungi, a nucleic acid sequence derived from fungus A may be used, for example, in order to inhibit the infection of a plant by fungus A and fungus B, and/or by fungi A, B, C and D etc. (see below).

In a preferred embodiment, the at least one nucleic acid sequence comprises several nucleic acid sequences which are homologous and/or complementary to several different nucleic acid sequences of a fungus and which are transcribed in the plant, so that upon infection of the plant with said fungus, the nucleic acid sequences transcribed in the plant interact with the respective homogenous and/or complementary nucleic acid sequences of the fungus or with parts thereof, so that the expression of the nucleic acid sequences of the fungus is substantially inhibited. In this way, the expression of several fungal genes may be inhibited by the plant at the same time, and increased resistance to individual or preferably various fungal pathogens may be imparted to the transgenic plant.

In a preferred embodiment of the method of the invention, the recombinant nucleic acid molecule comprises two nucleic acid sequences.

In another preferred embodiment of the method of the invention, the recombinant nucleic acid molecule comprises three nucleic acid sequences.

The inhibition of the expression of a nucleic acid of an organism is referred to as "gene silencing" by those skilled in the art. Said method is also referred to as "host-induced gene silencing" (HIGS), since the "gene silencing" of the fungal gene is caused by a nucleic acid sequence which is formed by the host of the fungus, i.e. the plant.

Those skilled in the art know various techniques which may cause "gene silencing". The expression of the nucleic acid sequence of a fungus may be substantially inhibited in transgenic plants for example by "silencing". For silencing, a nucleic acid sequence which is identical to a nucleic acid sequence of a fungus and/or which is complementary thereto is transferred to the plant. To ensure that the plants are transgenic for the introduced nucleic acids, the nucleic acid to be transferred is normally introduced to the plant by a vector, such as a plasmid, which is able to stably replicate in the plant cell or to integrate the introduced nucleic acid into the plant genome.

In this context, those skilled in the art refer to a nucleic acid sequence complementary to a nucleic acid sequence as antisense nucleic acid, wherein the same is typically antisense RNA. Use of antisense RNA leads to suppression of the corresponding endogenous gene. A nucleic acid sequence identical to a nucleic acid sequence is also referred to as sense nucleic acid. The use of sense RNA may also lead to suppression of the corresponding endogenous gene, by means of a process called "co-suppression".

If, in the scope of the present invention, sense sequences are mentioned, it is referred to those sequences, which correspond to the coding strand of a nucleic acid sequence of a fungus, or which comprise parts thereof. Such sequences do not have to be 100% identical to the fungal genes of interest. It should be sufficient if said sequences are at least 50% identical, preferably at least 60%, especially preferably at least 70%, further especially preferably at least 80%, in particular preferably at least 90% and most preferably at least 95% identical. In case of such degrees of identity, the sequences are regarded, according to the invention, as homologous to each other or comprising a homology. The deviations to the nucleic acids of fungi or parts thereof may originate from deletion, addition, substitution and/or insertion. The skilled person surely knows that with decreasing identity, it becomes more likely that multiple nucleic acids are suppressed in a silencing manner. Sequences having such a low degree of identity or homology that the expression of endogenous genes of the transgenic plant is suppressed, are not specific enough for the method of the present invention, and are not suitable, since they may interfere with the metabolism of the plant.

Respectively, if antisense sequences are mentioned, those sequences of the invention are referred to which correspond to the codogenous DNA strand of the fungal genes. Said sequences are preferably complementary to at least 50%, preferably complementary to at least 60%, especially preferably complementary to at least 70%, further especially preferably complementary to at least 80%, in particular preferably complementary to at least 90%, and most preferably complementary to at least 95%, 98% and/or 99%. As mentioned above, it is sufficient if the antisense sequences are able to hybridize specifically with the mRNA of the respective fungal gene of interest, but not with the endogenous mRNA of the transgenic plant. Hybridization of an antisense sequence with a mRNA sequence of the fungus typically takes place in vivo under cellular conditions, or in vitro.

In a preferred embodiment of the above-mentioned method, the recombinant nucleic acid molecule comprises a promoter functional in plants and operatively linked thereto the at least one nucleic acid sequence.

Said promotors of the present invention may be constitutive, but also inducible or tissue and/or development-specific promotors.

In order to carry out the present invention, promotors which are suitable for the expression of genes in plants may be generally obtained from various sources, such as from plants or plant viruses, for example. The selection of the promotor and other regulatory sequences determines the spatial and temporal expression pattern in transgenic plants.

The at least one nucleic acid sequence of the present invention may be present in antisense or sense orientation (identical or complementary to the nucleic acid sequence of the fungus).

In a preferred embodiment of the present invention, the at least one nucleic acid sequence is present in antisense orientation, so that upon transcription of said sequence in plant cells a RNA molecule is created, the sequence of which being complementary to the nucleic acid of the fungus. By hybridizing the antisense sequence with the nucleic acid sequence of the fungus in vivo, the expression of the nucleic acid sequence of the fungus may be suppressed in plant cells, whereby the plant becomes resistant to said fungus.

In another preferred embodiment of the present invention, the at least one nucleic acid sequence is present in sense orientation, so that upon transcription of said sequence in plant cells a RNA molecule is created, the sequence of which being identical to the nucleic acid of the fungus. Those skilled in the art know that, upon expression of such sense sequences in plants, antisense RNAs (asRNAs) may be formed which may cause silencing of both, the transgene, i.e. the at least one nucleic acid sequence according to the invention, and the endogenous, corresponding gene (co-suppression). By co-suppressing the nucleic acid sequence of the fungus in vivo, the expression of the nucleic acid sequence of the fungus may be suppressed in plant cells, whereby the plant becomes resistant to said fungus.

The nucleic acid sequence of the present invention may consist of or be derived from a naturally occurring nucleic acid sequence or a synthetically produced, by sequence comparison derived or recombinantly produced nucleic acid sequence.

In a preferred embodiment, the at least one nucleic acid sequence of the present invention comprises at least 50 bp, at least 100 bp, at least 150 bp, at least 200 bp, at least 250 bp, or at least 300 bp.

In another embodiment of the method of the present invention, vectors are used for introducing the nucleic acids in the plant cells which comprise a promoter in 5'-3'-orientation functional in plants, operatively linked thereto a DNA sequence coding for a ribozyme which specifically recognizes the nucleic acid sequence of a fungus, and a termination sequence. Those skilled in the art know how ribozymes which exhibit an endonuclease activity directed against a certain nucleic acid sequence, for example a mRNA, may be produced. In the scope of the invention, the term "ribozyme" also refers to those RNA sequences which comprise next to the actual ribozyme leading sequences which are complementary to the nucleic acid sequence of the fungus or parts thereof, and thus directs the mRNA-specific ribozyme even more target-orientedly to the mRNA substrate of the ribozyme.

In another preferred embodiment of the above-mentioned method, the recombinant nucleic acid molecule comprises a promoter which is functional in plants being operatively linked thereto the at least one nucleic acid sequence, another nucleic acid sequence coding for ribonuclease P, and a termination sequence. Upon transcription of such vectors, RNA molecules are formed in the cell having a leading sequence (the antisense sequence), which directs the RNAse P to the mRNA of the fungal gene, thereby causing the cleavage of the mRNA by RNAse P (U.S. Pat. No. 5,168,053). Preferably, the leading sequence comprises 10 to 15 nucleotides which are complementary to the mRNA of a fungal gene and a 3'-NCCA nucleotide sequence, wherein N preferably is a purine. The transcripts of the external leading sequence bind to the target mRNA by the formation of base pairs, thus enabling cleavage of the mRNA by RNAse P at nucleotide 5' from the paired region. Such cleaved mRNA cannot be translated into a functional protein.

The skilled person further knows diverse techniques for suppressing or inhibiting the expression of an endogenous gene by small double-stranded RNA molecules, so-called small interfering RNAs, or siRNAs.

Thereby, the double-stranded RNA molecule confers the specific degradation of the corresponding nucleic acid sequence, i.e. the nucleic acid sequence, from which the double-stranded RNA sequence has been derived. By enzymatic cleavage, e.g. by the dicer enzyme complex, RNA fragments having a length of 19-25 nucleotides, the so-called siRNAs, result from double-stranded RNA substrates. Such double-stranded RNA molecules (dicer substrates) must have at least a length of 25 bp, those skilled in the art know, however, that also substantially longer double-stranded RNA molecules are suitable substrates. Due to the very high sequence identity of both siRNAs, the siRNAs are commonly present as double-stranded RNA. The siRNAs may inhibit or prevent gene expression in many different ways:
  a) transcription (transcriptional gene silencing or TGS)
  b) degradation of the mRNA (post transcriptional gene silencing or PTGS)
  c) translation.

Said method for suppressing the expression of an endogenous nucleic acid sequence by sequence-specific double-stranded RNA is known to those skilled in the art as RNA interference or RNAi (Zamore et al. (2000) *Cell* 101:25-33; Tang et al. (2003) *Genes Dev.* 17:49-63, Smith et al. (2000) *Nature* 407: 319-320).

The use of RNAi constructs according to the invention is based on the above-mentioned mechanisms for inhibiting gene expression of a nucleic acid sequence of a fungus. Thereby, the corresponding polypeptide(s) cannot be formed. As discussed in detail above, according to the invention the expression of essential nucleic acid sequences of the fungus is inhibited. Said nucleic acid sequences are highly conserved in various fungi. Accordingly, those skilled in the art know that the sequence-specific inhibition of the expression of such a nucleic acid sequence in a transgenic plant of the present invention extends to all fungi which have a homologous section in the corresponding nucleic acid sequence.

Those skilled in the art know that various strategies may be chosen to make double-stranded RNA available as dicer substrate in the cell, and thus to trigger a specific RNAi effect.

In a preferred embodiment of the method of the invention, the recombinant nucleic acid molecule comprises a RNAi construct.

In a preferred embodiment of the above-mentioned method, the recombinant nucleic acid molecule comprises a promoter which is functional in plants, operatively linked thereto is the at least one nucleic acid sequence, wherein said sequence has reverse-complementary regions, and a termination sequence. The skilled person knows respective constructs in which a nucleic acid sequence has reverse-complementary regions, so that after transcription of such a construct and self-hybridization within the nucleic acid sequence with the mentioned reverse-complementary regions, again double-stranded RNA is being formed, which is also a substrate for the dicer enzyme complex, for example. Accordingly, siRNA molecules are also formed, which lead to the degradation of a corresponding nucleic acid of a fungus. The above-mentioned reverse-complementary nucleic acid sequences are also referred to as inverted repeats.

In another preferred embodiment, the recombinant nucleic acid molecule comprises a promoter which is functional in plants, operatively linked thereto is the at least one nucleic acid sequence, a "short hairpin" structure-generating nucleic acid and the nucleic acid sequence which is reverse-complementary to the at least one nucleic acid sequence, and a termination sequence.

By refolding the "short hairpin" structure, the at least one nucleic acid sequence and the nucleic acid sequence reverse-complementary thereto may hybridize, form double-stranded RNA and induce the PTGS system. Respective constructs and double-stranded RNA molecules are known to those skilled in the art for example as "short hairpin" RNAs or shRNAs. Typically, such constructs are led by U6 promotor or a CaMV35S promotor (Tuschl (2002) vide supra; Paul et al. (2002) Nat. Biotechnol. 20: 505-508; Paddison et al. (2002) *Genes Dev.* 16(8): 948-958; Brummelkamp et al. (2002) *Science* 296: 550-553).

In another preferred embodiment, the recombinant nucleic acid molecule comprises a RNAi construct, wherein the at least one nucleic acid sequence comprises a sequence selected from the group consisting of SEQ ID NOs: 1-16 or parts thereof, and a sequence reverse-complementary thereto.

In another preferred embodiment, the recombinant nucleic acid molecule comprises a RNAi construct, wherein the at least one nucleic acid sequence comprises two sequences selected from the group consisting of SEQ ID NOs: 1-16 or parts thereof, and one or two sequences reverse-complementary thereto.

In another preferred embodiment, the recombinant nucleic acid molecule comprises a RNAi construct, wherein the at least one nucleic acid sequence comprises three sequences selected from the group consisting of SEQ ID NOs: 1-16 or parts thereof, and one or more sequences reverse-complementary thereto.

In an especially preferred embodiment of the method of the present invention using the RNAi methodology, the recombinant nucleic acid molecule comprises a promoter which is functional in plants, the at least one nucleic acid sequence is operatively linked thereto, an intron comprising splice donor and splice acceptor sequences, the nucleic acid sequence reverse-complementary to the at least one nucleic acid sequence of the present invention, and a termination sequence.

So-called termination sequences are sequences which ensure that the transcription or the translation is terminated properly. If the transmitted nucleic acids are to be translated, said nucleic acids are typically stop codons and corresponding regulatory sequences; if the transmitted nucleic acids are only to be transcribed, said nucleic acids are normally poly-A sequences.

If such vectors are stably introduced in plant cells, first a pre-mRNA is formed upon transcription of said vectors which consists of a first exon comprising the at least one nucleic acid sequence of the present invention, an intron and a second exon comprising the nucleic acid sequence reverse-complementary to the at least one nucleic acid sequence. Since the intron is removed by the splicing procedure, a continuous RNA molecule is formed having regions which are complementary to each other, and thus being a substrate for specific enzyme complexes, such as the dicer enzyme complex. Those skilled in the art know that the position of the antisense (3'-5') and sense (5'-3') sequences may be interchanged in the vector. The same applies of course to the above-mentioned recombinant nucleic acid molecules of the present invention in which several siRNAs are contained. Therefore, e.g. for three various siRNAs, different configurations of the polarity (sense/antisense) are possible, such as:

| siRNA#1 | siRNA#2 | siRNA#3 | (reverse #1 | reverse #2 | reverse #3) |
|---------|---------|---------|-------------|------------|-------------|
| 5'-3'   | 5'-3'   | 5'-3'   | (3'-5'      | 3'-5'      | 3'-5')      |
| 5'-3'   | 5'-3'   | 3'-5'   | (3'-5'      | 3'-5'      | 5'-3')      |
| 5'-3'   | 3'-5'   | 5'-3'   | (3'-5'      | 5'-3'      | 3'-5')      |
| 5'-3'   | 3'-5'   | 3'-5'   | (3'-5'      | 5'-3'      | 5'-3')      |
| 3'-5'   | 5'-3'   | 5'-3'   | (5'-3'      | 3'-5'      | 3'-5')      |
| 3'-5'   | 5'-3'   | 3'-5'   | (5'-3'      | 3'-5'      | 5'-3')      |
| 3'-5'   | 3'-5'   | 5'-3'   | (5'-3'      | 5'-3'      | 3'-5')      |
| 3'-5'   | 3'-5'   | 3'-5'   | (5'-3'      | 5'-3'      | 5'-3')      |

Of course, the present invention also contains such recombinant nucleic acid molecules in which the 5'-3' sequence is varied, e.g.
  siRNA#2 siRNA#1 siRNA#3
  etc. (see below)

In an embodiment of the method of the invention, the recombinant nucleic acid molecule comprises a RNAi construct comprising an intron between the at least one nucleic acid sequence and the sequence reverse-complementary thereto.

In an embodiment of the method of the invention, the recombinant nucleic acid molecule comprises a RNAi construct, comprising an intron between the at least one nucleic acid sequence and the sequence reverse-complementary thereto, wherein the at least one nucleic acid sequence comprises a nucleic acid sequence selected from the group consisting of SEQ ID NOs: 1-16 or parts thereof, and the sequence reverse-complementary thereto.

In an especially preferred embodiment, the recombinant nucleic acid molecule comprises a RNAi construct, comprising an intron between the at least one nucleic acid sequence and the sequence reverse-complementary thereto, wherein the at least one nucleic acid sequence comprises a nucleic acid sequence coding for the mitochondrial ADP/ATP translocator (AAC) from a fungus or a part thereof, and the sequence reverse-complementary thereto.

In an especially preferred embodiment, the recombinant nucleic acid molecule comprises a RNAi construct comprising an intron between the at least one nucleic acid sequence and the sequence reverse-complementary thereto, wherein the at least one nucleic acid sequence comprises a nucleic acid sequence, coding for the mitochondrial heat shock protein 70 from a fungus or a part thereof, and the sequence reverse-complementary thereto.

In an embodiment of the method according to the invention, the recombinant nucleic acid molecule comprises a RNAi construct comprising an intron between the at least one nucleic acid sequence and the sequence reverse-complementary thereto, wherein the at least one nucleic acid sequence comprises two nucleic acid sequences, and the sequences reverse-complementary thereto.

In an embodiment of the method according to the invention, the recombinant nucleic acid molecule comprises a RNAi construct comprising an intron between the at least one nucleic acid sequence and the sequence reverse-complementary thereto, wherein the at least one nucleic acid sequence comprises two nucleic acid sequences selected from the group consisting of SEQ ID NOs: 1-16 or parts thereof, and the sequences reverse-complementary thereto.

In a preferred embodiment of the method according to the invention, the recombinant nucleic acid molecule comprises a RNAi construct comprising an intron between the at least one nucleic acid sequence and the sequence reverse-complementary thereto, wherein the at least one nucleic acid sequence comprises two nucleic acid sequences in random 5'-3' sequence selected from the group consisting of nucleic acid sequences, coding for gamma-actin (GA) from a fungus, the mitochondrial ADP/ATP translocator (AAC) from a fungus, the mitochondrial heat shock protein 70 (Hsp) from a fungus, the elongation factor 1 (EF1) from a fungus and the Rho GTPase (Rho) from a fungus or a respective part of each, and the sequences reverse-complementary thereto.

In an embodiment of the method according to the invention, the recombinant nucleic acid molecule comprises a RNAi construct comprising an intron between the at least one nucleic acid sequence and the sequence reverse-complementary thereto, wherein the at least one nucleic acid sequence comprises three nucleic acid sequences, and the sequences reverse-complementary thereto.

In an embodiment of the method according to the invention, the recombinant nucleic acid molecule comprises a RNAi construct comprising an intron between the at least one nucleic acid sequence and the sequence reverse-complementary thereto, wherein the at least one nucleic acid sequence comprises three nucleic acid sequences selected from the group consisting of SEQ ID NOs: 1-16 or parts thereof, and the sequences reverse-complementary thereto.

In a preferred embodiment of the method of the invention, the recombinant nucleic acid molecule comprises a RNAi construct comprising an intron between the at least one nucleic acid sequence and the sequence reverse-complementary thereto, wherein the at least one nucleic acid sequence comprises three nucleic acid sequences in random 5'-3' sequence selected from the group consisting of nucleic acid sequences coding for gamma-actin (GA) from a fungus, the mitochondrial ADP/ATP translocator (AAC) from a fungus, the mitochondrial heat shock protein 70 (Hsp) from a fungus, the elongation factor 1 (EF1) from a fungus and the Rho GTPase (Rho) from a fungus or a respective part of each, and the sequences reverse-complementary thereto.

In an especially preferred embodiment, the recombinant nucleic acid molecule comprises a RNAi construct comprising an intron between the at least one nucleic acid sequence and the sequence reverse-complementary thereto, wherein the at least one nucleic acid sequence comprises three nucleic acid sequences coding for the gamma-actin (GA) from a fungus or a part thereof, the mitochondrial ADP/ATP translocator (AAC) from a fungus or a part thereof, and the mitochondrial heat shock protein 70 (Hsp) from a fungus or a part thereof, and the sequences reverse-complementary thereto.

In another especially preferred embodiment, the recombinant nucleic acid molecule comprises a RNAi construct comprising an intron between the at least one nucleic acid sequence and the sequence reverse-complementary thereto, wherein the at least one nucleic acid sequence comprises three nucleic acid sequences coding for the gamma-actin (GA) from a fungus or a part thereof, the mitochondrial ADP/ATP translocator (AAC) from a fungus or a part thereof, and the elongation factor 1 (EF1) from a fungus or a part thereof, and the sequences reverse-complementary thereto.

In another especially preferred embodiment, the recombinant nucleic acid molecule comprises a RNAi construct comprising an intron between the at least one nucleic acid sequence and the sequence reverse-complementary thereto, wherein the at least one nucleic acid sequence comprises three nucleic acid sequences coding for the gamma-actin (GA) from a fungus or a part thereof, the Rho GTPase (Rho) from a fungus or a part thereof, and the elongation factor 1 (EF1) from a fungus or a part thereof, and the sequences reverse-complementary thereto.

In another especially preferred embodiment, the recombinant nucleic acid molecule comprises a RNAi construct comprising an intron between the at least one nucleic acid sequence and the sequence reverse-complementary thereto, wherein the at least one nucleic acid sequence comprises three nucleic acid sequences coding for the gamma-actin (GA) from a fungus or a part thereof, the Rho GTPase (Rho) from a fungus or a part thereof, and the mitochondrial heat shock protein 70 (Hsp) from a fungus or a part thereof, and the sequences reverse-complementary thereto.

In another especially preferred embodiment, the recombinant nucleic acid molecule comprises a RNAi construct comprising an intron between the at least one nucleic acid sequence and the sequence reverse-complementary thereto, wherein the at least one nucleic acid sequence comprises three nucleic acid sequences coding for the mitochondrial ADP/ATP translocator (AAC) from a fungus or a part thereof, the Rho GTPase (Rho) from a fungus or a part thereof, and the elongation factor 1 (EF1) from a fungus or a part thereof, and the sequences reverse-complementary thereto.

Of course, embodiments, wherein the inhibition and/or prevention of the expression of various fungal genes is achieved by the simultaneous usage of several RNAi constructs, are also part of the present invention.

In an embodiment, the method according to the invention comprises two recombinant nucleic acid molecules comprising RNAi constructs comprising an intron between the at least one nucleic acid sequence and the sequence reverse-complementary thereto, wherein the at least one nucleic acid sequence comprises one, two or three nucleic acid sequences selected from the group consisting of SEQ ID NOs: 1-16 or parts thereof, and the sequences reverse-complementary thereto.

In an embodiment, the method according to the invention comprises three recombinant nucleic acid molecules comprising RNAi constructs comprising an intron between the at least one nucleic acid sequence and the sequence reverse-complementary thereto, wherein the at least one nucleic acid sequence comprises one, two or three nucleic acid sequences selected from the group consisting of SEQ ID NOs: 1-16 or parts thereof, and the sequences reverse-complementary thereto.

In another preferred embodiment, the at least one nucleic acid sequence comprises a nucleic acid sequence of at least 19 nucleotides, at least 20 nucleotides, at least 21 nucleotides, at least 22 nucleotides, at least 23 nucleotides, at least 24 nucleotides and at least 25 nucleotides having a sequence identity of at least 40%, preferably at least 50%, further preferably at least 60%, also preferably at least 70% and/or 75%, especially preferably at least 80%, 82%, 84%, 86% and/or 88%, in particular preferably at least 90%, 92% and/or 94%, and most preferably at least 95%, 96%, 97%, 98% and/or 99% compared to another nucleic acid sequence selected from the group consisting of SEQ ID NOs: 1-16 or parts thereof.

In a preferred embodiment, the at least one nucleic acid sequence comprises two nucleic acid sequences, each of at least 19 nucleotides, at least 20 nucleotides, at least 21 nucleotides, at least 22 nucleotides, at least 23 nucleotides, at least 24 nucleotides and at least 25 nucleotides having a sequence identity of at least 40%, preferably at least 50%, further preferably at least 60%, also preferably at least 70% and/or 75%, especially preferably at least 80%, 82%, 84%, 86% and/or 88%, in particular preferably at least 90%, 92% and/or 94%, and most preferably at least 95%, 96%, 97%, 98% and/or 99% compared to another nucleic acid sequence selected from the group consisting of SEQ ID NOs: 1-16 or parts thereof.

In another preferred embodiment, the at least one nucleic acid sequence comprises three nucleic acid sequences, each of at least 19 nucleotides, at least 20 nucleotides, at least 21 nucleotides, at least 22 nucleotides, at least 23 nucleotides, at least 24 nucleotides and at least 25 nucleotides having a sequence identity of at least 40%, preferably at least 50%, further preferably at least 60%, also preferably at least 70% and/or 75%, especially preferably at least 80%, 82%, 84%, 86% and/or 88%, in particular preferably at least 90%, 92% and/or 94%, and most preferably at least 95%, 96%, 97%, 98% and/or 99% compared to another nucleic acid sequence selected from the group consisting of SEQ ID NOs: 1-16 or parts thereof.

In a preferred embodiment, the at least one nucleic acid sequence comprises a nucleic acid sequence of at least 50 nucleotides, at least 100 nucleotides, at least 150 nucleotides, at least 200 nucleotides, at least 250 nucleotides, at least 300 nucleotides and at least 350 nucleotides having a sequence identity of at least 40%, preferably at least 50%, further preferably at least 60%, also preferably at least 70% and/or 75%, especially preferably at least 80%, 82%, 84%, 86% and/or 88%, in particular preferably at least 90%, 92% and/or 94%, and most preferably at least 95%, 96%, 97%, 98% and/or 99% compared to another nucleic acid sequence selected from the group consisting of SEQ ID NOs: 1-16 or parts thereof.

In a preferred embodiment, the at least one nucleic acid sequence comprises two nucleic acid sequences of at least 50 nucleotides, at least 100 nucleotides, at least 150 nucleotides, at least 200 nucleotides, at least 250 nucleotides, at least 300 nucleotides and at least 350 nucleotides having a sequence identity of at least 40%, preferably at least 50%, further preferably at least 60%, also preferably at least 70% and/or 75%, especially preferably at least 80%, 82%, 84%, 86% and/or 88%, in particular preferably at least 90%, 92% and/or 94%, and most preferably at least 95%, 96%, 97%, 98% and/or 99% compared to another nucleic acid sequence selected from the group consisting of SEQ ID NOs: 1-16 or parts thereof.

In a preferred embodiment, the at least one nucleic acid sequence comprises three nucleic acid sequences of at least 50 nucleotides, at least 100 nucleotides, at least 150 nucleotides, at least 200 nucleotides, at least 250 nucleotides, at least 300 nucleotides and at least 350 nucleotides having a sequence identity of at least 40%, preferably at least 50%, further preferably at least 60%, also preferably at least 70% and/or 75%, especially preferably at least 80%, 82%, 84%, 86% and/or 88%, in particular preferably at least 90%, 92% and/or 94%, and most preferably at least 95%, 96%, 97%, 98% and/or 99% compared to another nucleic acid sequence selected from the group consisting of SEQ ID NOs: 1-16 or parts thereof.

Those skilled in the art know that for RNAi and/or PTGS the sense and antisense RNAs used for forming double-stranded RNA molecules may be of different sizes (Tuschl (2002) *Nat. Biotechnol.* 20: 446-448).

Another part of the present invention is the method according to the invention, wherein synthetic double-stranded siRNAs are used for inhibiting the expression of a nucleic acid of a fungus, which typically have a length of 19-21 nucleotides. Such synthetic siRNAs may be introduced in the respective plant cell or plant by biolistic transformation techniques. Such synthetic siRNA molecules may activate the PTGS system in plants, and trigger a RNAi effect (Hamilton and Baulcombe (1999) *Science* 286: 950-2).

The selection of the target sequence for siRNA inhibition as well as the siRNA sequence motif may be determined according to the rules and regulations known to those skilled in the art, for example according to Elbashir et al. (2001) *Nature* 411: 494-8. If the target sequence for the siRNA mediated inhibition lies within the coding regions of the gene, or within the mRNA, those skilled in the art know, for example, that the target sequence for a siRNA inhibition may typically be 70 nucleotides downstream from the start codon in 5'-3' direction and 50 nucleotides upstream from the stop codon.

The sequence region may then be searched for the sequence motif AA (N19), wherein N may be each nucleotide. Said sequence motif typically comprises the AA dinucleotide, followed by 19 nucleotides, and preferably two additional uridine or thymidine residues. In general, the thymidine residues may be replaced by uridine residues in the siRNA sequence.

Further, those skilled in the art know the rules and regulations, established by Reynolds et al. ((2004) *Nat. Biotechnol.* 22:326-30):

1. a guanine/cytosine content of 30-50%
2. at least three adenine or uracil groups at positions 15 to 19 of the sense strand
3. no intermolecular "hairpin" structures
4. one adenine residue at position 19 of the sense strand
5. one adenine residue at position 3 of the sense strand
6. one uracil residue at position 10 of the sense strand
7. no guanine or cytosine residue at position 19 of the sense strand
8. no guanine residue at position 13 of the sense strand.

These eight criteria may be rated as follows:
(i) 1 point each for criteria 1, 3, 4, 5 and 6
(ii) 1 point each for each adenine or uridine residue at position 15 to 19, at least 3 corresponding bases (criterion 2)
(iii) minus 1 point each for not fulfilling the criteria 7-8.

According to Reynolds et al., only these siRNAs should be considered which have at least 6 points. Such siRNAs which fulfil the above-mentioned criteria may be checked by respective search programs, e.g. BLAST, whether there are any, if possible no or only little, homologies to nucleic acid sequences of the plant.

In another preferred embodiment of the method of the invention, the at least one nucleic acid sequence is selected from the group consisting of
(i) nucleic acids comprising SEQ ID NOs: 1-16 or fragments thereof, and/or
(ii) nucleic acids which hybridize under stringent conditions with a complementary strand of a nucleic acid of (i).

The term "hybridizing under stringent conditions" denotes in the context of the present invention that the hybridization is implemented in vitro under conditions which are stringent enough to ensure a specific hybridization. Stringent in vitro hybridization conditions are known to those skilled in the art and may be taken from the literature (e.g. Sambrook and Russell (2001) *Molecular Cloning: A Laboratory Manual*, 3rd edition, Cold Spring Harbour Laboratory Press, Cold Spring Harbour, N.Y.). The term "specific hybridization" refers to the circumstance that a molecule, under stringent conditions, preferably binds to a certain nucleic acid sequence, i.e. the target sequence, if the same is part of a complex mixture of, e.g. DNA or RNA molecules, but does not, or at least very rarely, bind to other sequences.

Stringent conditions depend on the circumstances. Longer sequences hybridize specifically at higher temperatures. In general, stringent conditions are chosen such that the hybridization temperature is about 5° C. below the melting point ($T_m$) of the specific sequence at a defined ionic strength and at a defined pH value. $T_m$ is the temperature (at a defined pH value, a defined ionic strength and a defined nucleic acid concentration), at which 50% of the molecules complementary to the target sequence hybridize to the target sequence in the state of equilibrium. Typically, stringent conditions are conditions, where the salt concentration has a sodium ion concentration (or concentration of a different salt) of at least about 0.01 to 1.0 M at a pH value between 7.0 and 8.3, and the temperature is at least 30° C. for small molecules (i.e. 10 to 50 nucleotides, for example). In addition, stringent conditions may include the addition of substances, such as, e.g., formamide which destabilises the hybrids. At hybridization under stringent conditions, as used herein, normally nucleotide sequences which are at least 60% homologous to each other hybridize to each other. Preferably, said stringent conditions are chosen such that sequences which are about 65%, preferably at least about 70%, and especially preferably at least about 75% or higher homologous to each other, normally remain hybridized to each other. A preferred non-restrictive example of stringent hybridization conditions is hybridizations in 6× sodium chloride/sodium citrate (SSC) at about 45° C., followed by one or more washing steps in 0.2×SSC, 0.1% SDS at 50 to 65° C. The temperature fluctuates, e.g. under standard hybridization conditions depending on the type of the nucleic acid, between 42° C. and 58° C. in aqueous buffer having a concentration of 0.1 to 5×SSC (pH value 7.2).

If an organic solvent, e.g. 50% formamide, is present in the above-mentioned buffer, the temperature is about 42° C. under standard conditions. Preferably, the hybridisation conditions for DNA:DNA hybrids are, for example, 0.1×SSC and 20° C. to 45° C., preferably 30° C. to 45° C. Preferably, the hybridisation conditions for DNA:RNA hybrids are, for example, 0.1×SSC and 30° C. to 55° C., preferably between 45° C. and 55° C. The above-mentioned hybridization temperatures are determined, for example, for a nucleic acid which is 100 base pairs long and has a G/C content of 50% in the absence of formamide. Those skilled in the art know how to determine the required hybridization conditions using text books, such as those mentioned above, or the following textbooks, Current Protocols in Molecular Biology, John Wiley & Sons, N.Y. (1989), Hames and Higgins (publ.) 1985, Nucleic Acids Hybridization: A Practical Approach, IRL Press at Oxford University Press, Oxford; Brown (publ.) 1991, Essential Molecular Biology: A Practical Approach, IRL Press at Oxford University Press, Oxford.

Typical hybridization and washing buffers for example have the following composition:
Pre-Hybridization Solution: 0.5% SDS
  5×SSC
  50 mM $NaPO_4$, pH 6.8
  0.1% sodium pyrophosphate
  5×Denhardt's solution
  100 µg/mL salmon sperm DNA
Hybridization Solution: pre-hybridization solution
  1×10$^6$ cpm/mL probe (5-10 min 95° C.)
20×SSC: 3 M NaCl
  0.3 M sodium citrate
  ad pH 7 with HCl
50×Denhardt's Reagent: 5 g Ficoll
  5 g polyvinylpyrrolidone
  5 g bovine serum albumin
  ad 500 mL aqua destillata
A typical procedure for hybridization is as follows:
Optional: wash blot 30 min in 1×SSC/0.1% SDS at 65° C.
Pre-hybridization: at least 2 h at 50-55° C.
Hybridization: over night at 55-60° C.
Washing:

| 05 min | 2x SSC/0.1% SDS   | hybridization temp. |
| 30 min | 2x SSC/0.1% SDS   | hybridization temp. |
| 30 min | 1x SSC/0.1% SDS   | hybridization temp. |
| 45 min | 0.2x SSC/0.1% SDS | 65° C.              |
| 5 min  | 0.1x SSC          | room temperature    |

Those skilled in the art know that the given solutions and the presented protocol may be modified or have to be modified, depending on the application.

In order to produce RNAi constructs, the corresponding sense or antisense nucleic acid sequences for example may be inserted into an appropriate vector by restriction digestion and subsequent ligation.

Alternatively, the corresponding sense or antisense nucleic acid sequences for example may be inserted into the vector by homologous recombination, such as by the GATEWAY® system (Invitrogen) or the BD Creator™ system (BD Biosciences Clontech Co.).

In a preferred embodiment, the corresponding sense or antisense nucleic acid sequences are inserted into a vector by homologous recombination using the GATEWAY® system.

In another preferred embodiment of the above-mentioned method, the promotor is a constitutive promotor, an inducible promotor or a tissue-specific promotor.

Besides constitutive promotors, such as the ubiquitin promotor (Binet et al. (1991) *Plant Science* 79:87-94) and the actin promotor (McElroy et al. (1990) *Plant Cell* 2:163-171), the promotors of phosphoenolpyruvate-carboxylase from corn (Hudspeth et al. (1989) Plant Mol. Biol. 12:579) or of fructose-1,6-bisphosphatase from potato (WO 98/18940), which impart leaf-specific expression, are considered as tissue-specific promotors.

Wound-, light- or pathogen-induced promotors and other development depending promotors or control sequences may also be used (Xu et al. (1993) *Plant Mol. Biol.* 22:573-588; Logemann et al. (1989) *Plant Cell* 1:151-158; Stockhaus et al. (1989) *Plant Cell* 1:805-813; Puente et al. (1996) *EMBO J.* 15:3732-3734; Gough et al. (1995) *Mol. Gen. Genet.* 247: 323-337). A summary of useable control sequences may be found, for example, in Zuo et al. (2000) *Curr. Opin. Biotech.* 11:146-151.

Suitable promotors also include promotors which ensure expression in tissues only, e.g. epidermis-specific promotors, such as the GSTA1 promotor (Altpeter et al. (2005) *Plant Mol Biol.* 57:271-83), or promotors of photosynthetically active tissues, such as the ST-LS1 promotor (Stockhaus et al. (1987) *Proc. Natl. Acad. Sci. USA* 84:7943-7947; Stockhaus et al. (1989) *EMBO J.* 8:2445-2451). Promotors which are active during the plant transformation, plant regeneration or certain stages of said processes, e.g. cell division specific promotors, such as the histone H3 promotor (Kapros et al. (1993) *In Vitro Cell Dev. Biol. Plant* 29:27-32), or the chemically inducible Tet repressor system (Gatz et al. (1991) *Mol. Gen. Genet.* 227:229-237) may also be used. Other suitable promotors may be taken from the literature, e.g. Ward (1993, *Plant Mol. Biol.* 22:361-366). The same applies to inducible and cell- or tissue-specific promotors, such as meristem-specific promotors which have also been described in the literature and which are suitable within the scope of the present invention as well.

Particularly suitable promotors for the implementation of the present invention are fungal inducible promotors, and especially those, which are induced by pathogenic fungi and not by useful fungi (e.g. mycorrhiza in the soil). Such promotors, such as the GER4 promotor (WO 2006/128882), enable a highly specific creation of broad-spectrum resistance in transgenic plants whereby undesired side effects are significantly reduced and eliminated.

Further fungal inducible promotors comprise promotors, such as the GAFP-2 promotor (Sa et al. (2003) *Plant Cell Rep.* 22:79-84), which, e.g., is induced by the fungus *Trichoderma viride*, or the PAL promotor which is induced by inoculation with *Pyricularia oryzae* (Wang et al. (2004) *Plant Cell Rep.* 22:513-518).

Further preferred promotors are those which are in particular active in fruits. Examples of these are the promotor of a polygalacturonase gene, e.g. from tomato, which mediates expression during the ripening process of tomato fruits (Nicholass et al. (1995) *Plant Mol. Biol.* 28:423-435), the promotor of an ACC oxidase, e.g. from apples, which mediates ripening and fruit specificity in transgenic tomatoes (Atkinson et al. (1998) *Plant Mol. Biol.* 38:449-460), or the 2A11 promotor from tomato (van Haaren et al. (1991) *Plant Mol. Biol.* 17:615-630).

Furthermore, those skilled in the art are able to isolate further suitable promotors by means of routine procedures.

The skilled person knows that the use of inducible promotors allows for the production of plants and plant cells which only transiently express the sequences of the present invention, and thus silence transiently. Such transient expression allows for the production of plants which only show transiently increased fungal resistance. Such transiently increased resistance may be desired, if, for example, there is a risk of fungal contamination, and therefore the plants only have to be resistant to the fungus for a certain period of time. Further situations, in which transient resistance is desirable, are known to those skilled in the art. The skilled person also knows that transient expression and thus transient silencing and transient resistance may be achieved using vectors which do not replicate stably in plant cells and which carry the respective sequences for silencing of fungal genes.

In a preferred embodiment of the method of the invention, the ubiquitin promoter is used as constitutive promoter.

In another preferred embodiment of the method according to the invention, the epidermis-specific promoter GSTA1 is used as tissue-specific promoter.

In an especially preferred embodiment of the method according to the invention, the GER4 promoter is used as pathogen-inducible promoter.

The vectors which are used for the silencing of fungal nucleic acids further comprise regulatory elements besides the nucleic acid sequence to be transferred. Which specific regulatory elements must be included in said vectors depends on the respective procedure which is to be used for said vectors. Those skilled in the art, who are familiar with the above-mentioned various methods for producing transgenic plants in which the expression of a protein is inhibited know which regulatory elements and also other elements said vectors must include.

Typically, the regulatory elements which are contained in the vectors ensure the transcription and, if desired, the translation in the plant cell.

The term "operatively linked" related to nucleic acid sequences or DNA sections in vectors refers to the fact that the nucleic acid sequences are linked to the vectors such that the sequence is under transcriptional and/or translational control of a vector suitable for expression in plants.

The vectors of the present invention may for example also comprise enhancer elements as regulatory elements, further, said vectors may contain resistance genes, replication signals and further DNA regions which allow for a propagation of the vectors in bacteria, such as *E. coli*. Regulatory elements also comprise sequences which lead to a stabilization of the vectors in the host cells. In particular, such regulatory elements comprise sequences which enable a stable integration of said vector in the host genome of the plant or autonomous replication of said vector in the plant cells. Such regulatory elements are known to those skilled in the art.

Those skilled in the art also know that various vectors may be employed for the RNAi method. Such vectors may be designed such that the sense and antisense sequences are transcribed from a U6 promotor each, hybridize in the cell and induce the PTGS system (Tuschl (2002) *Nat. Biotechnol.* 20: 446-448; Miyagishi et al. (2002) *Nat. Biotechnol.* 20: 497-500; Lee et al. (2002) *Nat. Biotechnol.* 20: 500-505). A plurality of RNAi compatible vectors is commercially available.

In an especially preferred embodiment, the pIPKb007 vector is used.

In another special embodiment, the pIPKb010 vector is used.

In another special embodiment, the p6UGER4deltaSwaIntronRNAi vector is used.

It is obvious to those skilled in the art that the many different kinds of plants may be attacked by fungi.

A preferred embodiment of the method is a method of creating broad-spectrum resistance to fungi in monocotyledonous plants.

Examples of monocotyledonous plants are plants which belong to the genus *avena* (oat), *triticum* (wheat), *secale* (rye), *hordeum* (barley), *oryza* (rice), *panicum, pennisetum, setaria, sorghum* (millet), *zea* (corn) and the like.

In a particularly preferred embodiment of the method, the plant is a cereal plant, in particular wheat or barley.

In another especially preferred embodiment of the method, the plant is barley.

Another preferred embodiment of the method, the method is for creating broad-spectrum resistance to fungi in dicotyledonous plants.

Dicotyledonous plants or agricultural crops comprise, but are not limited to, cotton, legumes, e.g. pulses, and in particular alfalfa, soy beans, rape, canola, tomato, sugar beet, potato, sunflower, ornamental plants as well as trees. Further agricultural crops may comprise fruit (in particular apples, pears, cherries, grapes, citrus, pineapple and bananas), oil palms, tea, cacao and coffee bushes, tobacco, sisal as well as medicinal plants, such as rauwolfia and digitalis. Especially preferred are the cereals wheat, rye, oat, barley, rice, corn and millet as well as the dicotyledonous plants sugar beet, rape, soy, tomato, potato and tobacco. Further agricultural crops may be taken from U.S. Pat. No. 6,137,030.

Preferred plants are tagetes, sunflower, *arabidopsis*, tobacco, red pepper, soy, tomato, aubergine, pepper, carrot, potato, corn, lettuces and types of cabbage, cereals, alfalfa, oat, barley, rye, wheat, triticale, millet, rice, lucerns, flax, cotton, hemp, brassicacaea, such as rape or canola, sugar beet, sugar cane, nut and wine species or woody plants, such as aspen or yew.

An especially preferred embodiment of the method is a method for creating broad-spectrum resistance to fungi by means of RNAi method for inhibiting expression of a nucleic acid sequence of a fungus, wherein the corresponding transgenic plant is resistant to at least said fungus.

An especially preferred embodiment of the method is a method for creating broad-spectrum resistance to fungi by means of RNAi method for inhibiting expression of a nucleic acid sequence of a fungus, wherein the corresponding transgenic plant is resistant to at least another fungus.

In an especially preferred embodiment of the method according to the invention, broad-spectrum resistance to pathogenic fungi is created.

Especially preferred, the suppression of the expression of a nucleic acid sequence of a fungus creates broad-spectrum resistance to Plasmodiophoromycota, such as *Plasmodiophora brassicae* (clubroot of crucifers), *Spongospora subterranea* (powdery scab of potato tubers), *Polymyxa graminis* (root disease of cereals and grasses);

Oomycota, such as *Bremia lactucae* (downy mildrew on lettuce), *Peronospora* (downy mildrew) on snapdragon (*P. antirrhini*), onion (*P. destructor*), spinach (*P. effusa*), soy bean (*P. manchurica*), tobacco (blue mold; *P. tabacina*) alfalfa and clover (*P. trifolium*), *Pseudoperonospora humuli* (downy mildrew on hop), *Plasmopara* (downy mildrew on grapes) (*P. viticola*) and sunflower (*P. halstedii*), *Sclerophtohra macrospora* (downy mildrew in cereals and grasses), *Pythium* (seed rot, seedling damping-off, and root rot and all types of plants, e.g. leak at beta beet by *P. debaryanum*), *Phytophthora infestans* (late blight in potatoes, blight in tomatoes etc.), *Albugo* spec. (white rust on cruciferous plants);

Ascomycota, such as *Microdochium nivale* (snow mould on rye and wheat), *Fusarium graminearum, Fusarium culmorum* (spike rot, especially on wheat), *Fusarium oxysporum* (fusarium withering on tomato), *Blumeria graminis* (powdery mildrew on barley (f.sp. *hordei*) and wheat (f.sp. *tritici*)), *Erysiphe pisi* (mildrew in peas),

*Nectria galligena* (fruit tree cancer), *Unicnula necator* (powdery mildrew in grapevines), *Pseudopeziza tracheiphila* (red fire disease of grapevines), *Claviceps purpurea* (ergot on, e.g. rye and grasses), *Gaeumannomyces graminis* (blackleg on wheat, rye, and other grasses), *Magnaporthe grisea* (rice blast disease), *Pyrenophora graminea* (leaf strives on barley), *Pyrenophora teres* (net bloch on barley), *Pyrenophora tritici-repentis* (leaf spots (*tritici*) on wheat), *Venturia inaequalis* (apple scab), *Sclerotinia sclerotium* (stem rot, rape cancer), *Pseudopeziza medicaginis* (leaf spots on lucerne, white and red clover);

Basidiomycetes, such as *Typhula incarnata* (typhula rot on barley, rye, wheat), *Ustilago maydis* (smut on corn), *Ustilago nuda* (loose smut on barley), *Ustilago tritici* (loose smut on wheat, spelt), *Ustilago avenae* (loose smut on oat), *Rhizoctonia solani* (rhizoctonia disease on potatoes), *Sphacelotheca* spp. (head smut of sorghum), *Melampsora lini* (rust of flax), *Puccinia graminis* (black rust on wheat, barley, rye, oat), *Puccinia recondita* (brown rust on wheat), *Puccinia dispersa* (brown rust on rye), *Puccinia hordei* (brown rust on barley), *Puccinia coronata* (crown rust on oat), *Puccinia striiformis* (yellow rust on wheat, barley, rye and numerous grasses), *Uromyces appendiculatus* (rust), *Sclerotium rolfsii* (root and stem rots of many plants);

Deuteromycetes (Fungi imperfecti), such as *Septoria nodorum* (rust blotch) on wheat (*Septoria tritici*), *Pseudocercosporella herpotrichoides* (root rot on wheat, barley, rye), *Rynchosporium secalis* (leaf spot disease on rye and barley), *Alternaria solani* (early blight of potato, tomato), *Phoma betae* (leak on beta-root), *Cercospora beticola* (Cercospora leaf spot disease on beta-root), *Alternaria brassicae* (dark leaf spots of crucifers on rape, cabbage, and other cruciferous plants), *Verticillium dahliae* (verticillium wilt and root rot), *Colletotrichum lindemuthianum* (bean spot disease), *Phoma lingam*-damping off (take-all on cabbage; root and stem rot on rape), *Botrytis cinerea* (grey mould on grapevine, strawberry, tomato, hop etc.).

In an especially preferred embodiment of the method according to the invention, broad-spectrum resistance is created in a transgenic monocotyledonous plant to *Fusarium graminearum, Fusarium culmorum, Septoria tritici, Puccinia recondita, Puccinia striiformis, Puccinia triticina, Puccinia hordei, Blumeria graminis* ffssp., *Rhynchosporium secalis, Bipolaris sorokiniana, Magnaporte oryzae* and *Pyrenophora teres.*

In another especially preferred embodiment of the method according to the invention, broad-spectrum resistance is created in a transgenic dicotyledonous plant to *Phytophtora infestans, Uncinula necator, Plasmopora viticola, Uromyces* spec., *Phakopsora pachyrhizi* and *Erysiphe* sp.

In a preferred embodiment for creating broad-spectrum resistance to fungi by means of RNAi method directed against nucleic acid sequences from *Fusarium culmorum*, the transgenic plant is resistant at least to *Fusarium culmorum.*

In an especially preferred embodiment for creating broad-spectrum resistance to fungi by means of RNAi method directed against nucleic acid sequences from *Fusarium culmorum*, the transgenic plant is resistant at least to *Fusarium culmorum* and *Blumeria graminis.*

In the most preferred embodiment, the plant is barley (*Hordeum vulgare*).

Another aspect of the present invention refers to a transgenic plant cell having broad-spectrum resistance being produced according to the above-mentioned method.

In the sense of the present invention, a transgenic plant or plant cell is, as mentioned-above, a plant containing nucleic acid sequences which do not naturally occur in the plant, but which are homologous and/or complementary to a nucleic acid of a fungus. Said nucleic acid sequences are not able to interact with endogenous plant sequences, and to influence the expression thereof.

In a preferred embodiment, the transgenic plant cell contains a recombinant nucleic acid molecule comprising a promotor which is operatively linked to at least one nucleic acid sequence.

In a preferred embodiment, the transgenic plant cell contains one of the recombinant nucleic acid molecules, as defined above.

Another aspect of the present invention relates to a transgenic plant which contains one of the plant cells defined above.

A number of well-known techniques are available for introducing DNA into a plant host cell, and those skilled in the art may easily determine the suitable technique for each case. Said techniques comprise the transformation of plant cells with T-DNA using *Agrobacterium tumefaciens* or *Agrobacterium rhizogenes* as transformation means, the fusion of protoplasts, the direct gene transfer of isolated DNA in protoplasts, the electroporation of DNA, the introduction of DNA by the biolistic procedure, as well as other possibilities. Thereby, stable as well as transient transformants may be produced.

For injection and electroporation of DNA in plant cells, the used plasmids do not need to fulfil special requirements per se. The same applies to direct gene transfer.

Simple plasmids, such as pUC derivatives, may be used. If, however, entire plants are to be regenerated from cells which were transformed in such manner, the presence of a selectable marker gene becomes necessary. Those skilled in the art know all common selection markers, and thus there is no difficulty to select a suitable marker. Common selection markers create resistance in the transformed plant cells to a biocide or antibiotic, such as kanamycin, G418, bleomycin, hygromycin, methotrexate, glyphosate, streptomycin, sulfonyl urea, gentamycin or phosphinotricin and the like.

Depending on the introduction method of the desired genes into the plant cell, further DNA sequences may become necessary. If, for example, the Ti or Ri plasmid is used for the transformation of the plant cell, at least the right border, or very often both, the right and the left border of the T-DNA contained in the Ti and Ri plasmid needs to be linked to the genes to be inserted.

If agrobacteria are used for the transformation, the DNA to be inserted needs to be cloned into special plasmids, i.e. either into an intermediary vector or into a binary vector. The intermediary vectors may be integrated into the Ti or Ri plasmid of the agrobacteria by means of homologous recombination due to sequences which are homologous to sequences in the T-DNA. Same contains the vir region, required for the transfer of the T-DNA. Intermediary vectors are not able to replicate in agrobacteria. By means of a helper plasmid, the intermediary vector may be transferred to *Agrobacterium tumefaciens* (conjugation). Binary vectors are able to replicate in both, *E. coli* and in agrobacteria. Said vectors contain a selection marker gene and a linker or polylinker which are enframed by the right and left T-DNA border region. Same may be transformed directly into the agrobacteria (Holsters et al. (1978) *Molecular and General Genetics* 163: 181-187). The *agrobacterium*, serving as host cell, is to contain a plasmid which includes a vir region. The vir region is necessary for the transfer of the T-DNA into the plant cell. In addition, T-DNA may be present. The *agrobacterium*, transformed in such manner, is used for the transformation of plant cells.

For the transfer of the DNA into the plant cell, plant explants may be cultivated expediently with *Agrobacterium tumefaciens* or *Agrobacterium rhizogenes*. From the infected plant material (e.g. leaf cuttings, stem sections, roots, but also protoplasts or suspension-cultivated plant cells) entire plants may be regenerated in a suitable medium containing antibiotics or biocides for the selection of transformed cells. The regeneration of the plants is performed according to standard regeneration procedures using well-known culture media. The plants or plant cells obtained this way may then be examined in respect to the presence of the introduced DNA.

Other possibilities for introducing foreign DNA using the biolistic method or by protoplast transformation are well-known to those skilled in the art (see L. Willmitzer (1993) *Transgenic Plants in: Biotechnology, A Multi-Volume Comprehensive Treatise* (publisher: H. J. Rehm et al.), volume 2, 627-659, VCH Weinheim, Germany).

Whereas transformation of dicotyledonous plants or the cells thereof by Ti plasmid vector systems with the help of *Agrobacterium tumefaciens* has well been established for a period of time, monocotyledonous plants or the cells thereof may now also be transformed using vectors which are based on *agrobacteria* (see e.g. Chan et al. (1993) *Plant. Mol. Biol.* 22: 491-506).

Alternative systems for the transformation of monocotyledonous plants or the cells thereof are transformation by biolistic approach (Wan and Lemaux (1994) *Plant Physiol.* 104: 37-48; Vasil et al. (1993) *Bio/Technology* 11: 1553-1558; Ritala et al. (1994) *Plant␣Mol. Biol.* 24: 317-325; Spencer et al. (1990) *Theor. Appl. Genet.* 79: 625-631), the protoplast transformation, the electroporation of partially permeabilized cells, and the insertion of DNA by means of glass fibres.

The transformed cells grow within the plant in the usual manner (see also McCormick et al. (1986) *Plant Cell Reports* 5: 81-84). The resulting plants may be cultivated in the usual manner, and may be crossed with plants which have the same transformed genes or other genes. The hybrid individuals resulting therefrom have the respective phenotypical properties.

Two or more generations should be cultivated in order to ensure that the phenotypical feature is stably maintained and inherited. Seeds should also be harvested in order to ensure that the corresponding phenotype or other characteristics remain conserved.

According to common procedures, transgenic lines may also be determined, which are homozygous for the new nucleic acid molecules, and the phenotypical behaviour thereof may be examined with respect to a present or absent pathogen responsiveness, and said behaviour may be compared to the behaviour of hemizygous lines.

Of course, plant cells which contain the recombinant nucleic acid molecules of the present invention may also be further cultivated as plant cells (including protoplasts, calli, suspension cultures and the like).

The vectors represented above may be transmitted to plant cells in different ways. It depends on the chosen application, whether the vectors must be present in linear or circular form. Those skilled in the art know, if and when to use corresponding linearized vectors.

According to the invention, the term "transgenic plant" includes both the plant in its entity as well as all parts of the plant, in which the nucleic acid sequences homologous and/or complementary to fungal genes are transcribed. Such parts of a plant may be plant cells, plant seeds, leaves, petals and pollen. A "transgenic plant" is, according to the invention, also the propagating material of transgenic plants of the present invention, e.g. seeds, fruits, cuttings, tubers, pieces of root, etc., wherein said propagating material contains above-mentioned transgenic plant cells, and if necessary, transgenic parts of said plants, such as protoplasts, plant cells and calli.

Various procedures and possibilities may be used in the production of transgenic plants, as already discussed above. In general, plants or plant cells may be modified by means of common genetically-engineered transformation procedures such that the new nucleic acid molecules are integrated into the plant genome, i.e. that stable transformants are produced and the transmitted nucleic acid molecules are replicated with the plant genome. Depending on the vector system used, according to the invention, also transgenic plants may be produced in which the nucleic acids to be transferred are contained in the plant cell or the plant as autonomously replicating system. The vectors used for transforming the plants, must therefore contain DNA sequences which enable the replication of plasmids used for transformation within the cell.

Another object of the present invention is transgenic plants or plant cells which have been produced according to one of the methods of the present invention, and which have higher resistance to fungi compared to the wild type.

Another object of the present invention is transgenic plants or plant cells which have been produced according to one of the methods of the present invention, and which have broad-spectrum resistance to fungi compared to the wild type.

According to the invention, a "wild type" is the corresponding parental organism which has not been genetically modified.

Transforming plants with the recombinant nucleic acid molecule of the present invention may be performed by any known transformation procedure; suitable are, for example, the biolistic method, the *agrobacterium* mediated transformation, the protoplast transformation, the electroporation of partially permeabilized cells, and the introduction of DNA by means of glass fibres. Which respective procedure may best be employed for the transformation depends on the used test plant.

Preferably, the test plants are transformed by means of the biolistic transformation, since this approach results particularly fast and effectively in a transformation with a plurality of various recombinant nucleic acid molecules.

A transgenic plant or plant cell in the sense of the present invention is, as mentioned-above, a plant containing nucleic acid sequences which do not naturally occur in the plant but which are homologous and/or complementary to parts of the fungal genome. Said nucleic acid sequences are not able to interact with endogenous plant sequences and to influence the expression thereof.

Another object of the present invention relates to the usage of the transgenic plants of the present invention and the cells, cell cultures, parts and transgenic propagating materials derived thereof for the production of food and feed, pharmaceuticals or fine chemicals.

The infection of test plants with fungal organisms in order to examine potential resistance phenomena is a method well-known to those skilled in the art. The used test plants must be responsive to said used fungus, i.e. they must be able to serve as host plant for said fungus, and the fungal attack must be detectable by simple means. Preferred test plants are wheat or barley plants, which are, for example, inoculated with the powdery mildew fungus *Blumeria graminis*. "Inoculating" denotes contacting the plant with that fungus the plant is to be infected with, or with the infectious parts thereof, under conditions in which the fungus may enter a wild type plant.

The fungal infestation of the plant may then be evaluated by means of a suitable evaluation procedure. The visual evaluation, in which the formed fungal structures are detected in the plant and quantified, is particularly suitable. In order to identify the successfully transformed cells, a reporter gene, such as the β-glucuronidase (GUS) gene from *E. coli*, a fluorescence gene, such as the green fluorescence protein (GFP) gene from *Aequorea victoria*, the luciferase gene from *Photinus pyralis* or the β-galactosidase (lacZ) gene from *E. coli*, the expression of which in the plant cells may be proven by simple methods, is co-transformed in a suitable vector, preferably along with the RNAi construct. Optionally, the formed fungal structures may be stained by methods well-known to those skilled in the art in order to improve the determination thereof, e.g. by staining with coomassie or trypan blue.

Another aspect of the present invention relates to the above-defined recombinant nucleic acid molecules comprising at least one nucleic acid sequence, operatively linked to a promotor functional in plant cells, wherein the nucleic acid sequence
  a) is identical and/or complementary to one or more of the nucleic acids selected from SEQ ID NOs: 1-5 and/or a part thereof, or has a sequence identity of at least 85% to one or more of the nucleic acids selected from SEQ ID NOs: 1-5, and/or
  b) is identical and/or complementary to one or more of the nucleic acids, selected from SEQ ID NOs: 6-11 and/or a part thereof, or has a sequence identity of at least 85% to one or more of the nucleic acids selected from SEQ ID NOs: 6-11, or
  c) is identical and/or complementary to one or more of the nucleic acids, selected from SEQ ID NOs: 12-16 and/or a part thereof, or has a sequence identity of at least 85% to one or more of the nucleic acids selected from SEQ ID NOs: 12-16.

The nucleic acid molecules used in the method may be isolated using molecular biological standard techniques and the sequence information provided herein. With the help of comparison algorithms, which may be found for example on the NCBI homepage at <http colon slash slash>www <dot>ncbi <dot>nlm <dot>nih <dot>gov, a homologous sequence or homologous, conserved sequence regions on DNA or amino acid level may also be identified. Substantial parts of said sequence or the entire homologous sequence may be used as hybridization probe using standard hybridization techniques (such as, for example, described in Sambrook et al., vide supra) for the isolation of further nucleic acid sequences, which are useful in the method, from other organisms by screening cDNA and/or genomic libraries. Furthermore, a nucleic acid molecule may be isolated by polymerase chain reaction, wherein oligonucleotide primers are used on the basis of the sequences, or parts thereof, contained in the libraries (e.g. a nucleic acid molecule, comprising the entire sequence or a part thereof, may be isolated by polymerase chain reaction, using oligonucleotide primers, which have been created on the basis of said same sequence). For example, mRNA may be isolated from cells (e.g. by the guanidinium thiocyanate extraction method from Chirgwin et al. (1979) Biochemistry 18: 5294-5299), and cDNA may be produced using reverse transcriptase (e.g. Moloney MLV reverse transcriptase, available from Gibco/BRL, Bethesda, MD, or AMV reverse transcriptase, available from Seikagaku America, Inc, St. Petersburg, Fla.). A nucleic acid may be amplified using cDNA or, alternatively, using genomic DNA as matrix and suitable oligonucleotide primers by means of standard PCR amplification techniques. The thus amplified nucleic acid may be cloned into a suitable vector, and may be characterized by means of DNA sequence analysis. Oligonucleotides, which are suitable for amplifying the desired sequence, may be produced by standard synthesis methods, e.g. with an automatic DNA synthesis device.

The exemplary identification of fungal genes which are suitable for the method of the present invention and the use thereof for creating broad-spectrum resistance in transgenic plants, will be described in the following. The following examples shall not limit the scope of the present invention. The content of all literature references, patent applications, patent specifications and patent publications, which are cited in this patent application, is incorporated herein by reference.

EXAMPLES

A. Method for Producing Triple RNAi Constructs

Producing the RNAi constructs of the present invention is based on the modified GATEWAY technology according to Douchkov et al. (2005) *Mol. Plant. Microbe. Interact.* 18:755-61.

Conserved proteins, or the genes encoding said conserved proteins, of phytopathogenic fungi serve as a basis for the RNAi constructs of the present invention. Examples here are gamma-actin, the mitochondrial ADP/ATP carrier protein, the RhoGTPase, the elongation factor 1, and the mitochondrial heat shock protein 70 chaperone.

Sequence sections within the genes, which are conserved in various fungi, encoding the above-mentioned proteins were determined by sequence comparisons.

For this purpose, corresponding DNA sequence data from various fungi were compared by the Sequencher software (Gene Codes Corp., Ann Arbor, Mich., USA) using the "dirtydata" algorithm, and a consensus sequence was derived.

The following sequences from the COGEME data base (<http colon slash slash>cogeme <dot>ex <dot>ac <dot>uk) and from the NCBI database (<http colon slash slash>www <dot>ncbi <dot>nlm <dot>nih <dot>gov <slash>sites <slash>entrez) were used as basis for the sequence comparisons of the different genes:

Gamma-actin (GA) BfCon[0048], Contig[0009], CpCon [0433], FsCon[0011], FsCon[0012], GzCon[0219], MagCon [0535], MagCon[10153a], MagCon[11943a], mg[1255], MGT_4266, Pi10229566, PiCon[0102], PsCon[0011], UmCon[0226], VD0108G03, YDL029W Chr4, YFL039C Chr6, YHR129C Chr8, YJR065C Chr10.

Elongation factor 1 (EF1): BfCon[0035], BfCon81924], BfCon[2093], Cf8667247, CtCon[0128], DQ522321, GzCon [0015], Mag3392227, MagCon[2061], MagCon[2896], MagCon[3191], MagCon[4553], MagCon[4838], MagCon [5002], MagCon[5960], MagCon[6041], MagCon[690a], MagCon[10107a], MagCon [12375a], MagCon[12727a], MagCon[13104a], MagCon[13904a], mg[0073], mg[0358], SSPG1015, Um34332478, UmCon[0014], UmCon[1272], UmCon[2780], VD0110B10, VD0201A10

Mitochondrial ADP/ATP translocator (AAC): BfCon [0014], BfCon[1221], Cf8667327, CfCon[0008], Contig [0005], FsCon[0026], FsCon[0406], GzCon[0025], mg[0104], SSPG985, VD0100D40, VD0203D11.

Mitochondrial heat shock protein 70 (Hsp70): BfCon [0098], Cf8667122, Cf8667223, FsCon[1028], FsCon [1857], Gz47835892, GzCon[1242], GzCon[2886], GzCon [3587], MagCon[2045], MagCon[10827a], mg[1360], mga0294f, UmCon[1735], UmCon[3134], VD0204G10.

Rho GTPase (Rho): AF395859, BfCon[0909], Bg13902524, Bg27453832, BgCon[2092], CfCon[0041], Contig[0007], CpCon[0819], CtCon[0239], FsCon[0840], Gz47836309, GzCon[0911], GzCon[7209], Lm13259684, Mag14180535, Mag30400635, Mag30403197, MagCon[0027a], MagCon[1398], MagCon[4208a], MagCon[6895], MagCon[11651a], mg[1439], mga0839f, SSPG240R, Um34331745, Um37403496, Um37407871, UmCon[0162], UmCon[0987], UmCon[1018], UmCon[2074], W0AA016ZE09C1.

As a result of the sequence comparisons, a consensus sequence was established for each gene (for nucleotide symbols, see table on page 87):

Consensus Sequence of AAC

```
GC:AGACCGTTCTTGGGCATGCCCCCCTTCGTCGCTGACTTCCTCATGGG
TGGTGTCTCCGCCGCTGTCTCCAAGACCGCTGCYGCCCCCATYGAGCGTG
TCAAGCTCCTCATCCAGAACCAGGATGAGATGCTGAAGACCGGTCGTCTY
GACCGCAAGTACGACGGCATTGGTGASTGCTTCAAGCGYACCACCGCSGA
TGAGGGTGTCATGTCCCTCTGGCGWGGHAACACTGCCAACGTCATCCGTT
ACTTCCCTACCCAGGCCCTGAACTTCGCTTTCCGTGACAAGTTCAAGTCG
ATGTTCGGCTACAAGAAGGACCGTGATGGCTACGCCATGTGGATGGCYGG
TAACYTKGCCTCCGGTGGTGCTGCTGGTGCCACTTCCCTCCTCTTCGTCT
ACTCCCTCGACTACGCCCGTACYCGTCTTGCCAACGACGCCAAGAACGCC
AAGACCGGTGGTGACCGTCAGTTCAACGGTCTSGTCGATGTCTACAAGAA
GACCCTCGCCTCTGACGGTATTGCCGGTCTCTACCGTGGTTTCGGT:CCT
TCCGTTGCTGGTATCGTCGTYTACCGTGGTCTCTACTTCGGWATGTACGA
YTCCATCAAGCCAGTCCTCCTCAYYGGWMMYCTYGAGGGYAACTTCCTT
GCWTCCTTCTTGCTCGGATGGACCGTCACCACTGGTGCCGGTATCGCCTC
TTACCCATTGGACACCATCCGTCGTCGTATGATGATGACTTCTGGTGAGG
CCGTCAAGTACAAGTCTTCCTTGGATGCTGSYCGYCARATCGTYGCCAAG
GAGGGWGTYAAGTCTCTCTTCAAGGGTGCTGGTGCCAACATTCTCCGTG
GTGTTGCAGGTGCTGGTGTCYTGTCCATCTACGATCARATGCARGTCYTG
ATGTTCGGAAAGGCATTCAAGTAAAYGWATCGTA:GA:ATGGAGTGAAGG
::G::ATGAG:T:TGAKTG:TAGA:GGTGGT:TGATGATAATGCGAAATG
AG:C:GCCT::TGRGGTCG:GTC:C:G:TGGTT:GA:AA::CT::AAAAG
GTTG:AG:ATSGTAG:TACAG::ATCSATTGC:ATTG:TG:T:TRSAGAT
AC:TT:GMCGTG:TAGTCTGMCAC::AR:CAWGATCT:AT:ACRA:TYTG
AGT:SGCTTMTG:CA:C:AGAGT::::CTT:TAT:CTA:ATCTTKCWTT:
GCCTTCCGTTCTATGCCKV:T:GTA:ATT::T::A:TACACCAATTCAAV
T::TCC:CTTTA:CTGTCTRTTCNCTTA:A:CTGAGDDTTMAATTTKRMK
CMTSTMKTCATCCTKKTCAKTGCTGACYCYTRTKTCTMCACTCTRTCTWT
TCSYTTTCWTCCATTTGCYMYVVCYCMCTCCTATCMKTAGCATACTWCGT
AYWATCYKTSTTGCCTAACGTMYKWACTACCYCYMTTTMYTRCTTWKCGA
TTACTMTYYCTWTMTYYCTYCGKTWMCMYTCWCSTWYMTGTTKCATTMTC
TCTGACTCTCTCTMTYCTCCCCTCTMTAYACYYKYYTTRTYCTKTYGCCM
YTMRYCCTMTCTTCTMATTTTCCTACTTCTATTCTCTTGCTATTTCTCTC
CTATCTGTTCCATCCCTTCATTCATCATTTCTCTCTCTGCTTCAACGA
TTATCATCACTATTCTATCTC
```

Consensus Sequence of EF1

```
ATGGGTAAAGGAGAAGACTCACATCAACGTCGTCGTCATCGGCCACGTC
GACTCCGGCAAGTCGACCACCACCGGTCACTTGATCTACAAGTGCGGTGG
TATCGACAAGCGTACCATCGAGAAGTTCGAGAAGGAAGCCGCCGAGCTC
GGYAAGGGTTCCTTCAAGTACGCCTGGGTTCTTGACAAGCTCAAGGCCGA
GCGTGAGCGTGGTATCACCATCGACATCGCCCTCTGGAAGTTCGAGACYC
CCAAGTACTATGTTACCGTCATTGACGCCCCTGGTCACCGTGACTTCATC
AAGAACATGATCACTGGTACCTCCCAGGCCGACTGCGCCATTCTCATCAT
TGCCGCTGGTACTGGTGAGTTCGAGGCTGGTATCTCCAAGGATGGCCAGA
CTCGTGAGCACGCTCTCCTCGCCTACACCCTCGGTGTCAAGCAGCTCATC
GTYGCCATCAACAAGATGGACACCACCAAGTGGTCCGAGGACCGTTWCC
AGGAGATCATCAAGGAGACCTCCAACTTCATCAAGAAGGTCGGCTACAA
CCCCAAGACYGTCGCCTTCGTCCCCATCTCCGGTTTCAACGGTGACAACA
TGMTCGACGCCTCCACCAACTGCCCCTGGTACAAGGGTTGGGAGAAGGA
GACCAAGKCWGGCAAGGYCACCGGCAAGACCCTCCTCGAGGCCATCGA
CGCCATCGAGCCCCCAAGCGTCCCACCGACAAGCCCCTCCGTCTTCCCC
TCCAGGATGTCTACAAGATCGGYGGTATTGGMACTGTTCCCGTCGGCCGT
RTCGAGACYGGTATCATCAAGCCCGGYATGGTCGTCACCTTCGCTCCCGC
CAACGTCACCACTGAAGTCAAGTCCGTCGAGATGCACCACGAGCAGCTC
ACTGAGGGTSTTCCCGGTGACAACGTCGGTTTCAACGTCAAGAACGTTTC
CGTCAAGGACATTCGCCGTGGTAACGTCGCTGGTGACTCCAAGAACGAC
CCCCCCAAGGGTGCCGCTTCCTTCAACGCYCAGGTCATYGTCCTYAACCA
CCCTGGTCAGGTCGGTGCTGGTTACGCCCCCGTTCTCGATTGCCACACTG
CCCACATTGCCTGCAAGTTCTCCGAGCTCCTCGAGAAGATCGACCGCCGT
ACCGGTAAGTCCATTGAGGACTCCCCCAAGTTCATCAAGTCTGGTGACGC
TGCCATCGTCAAGATGGTTCCCTCCAAGCCCATGTGTGTTGAGGCCTTCA
CYGACTACCCTCCTCTGGGMCGTTTCGCCGTCCGTGACATGCGTCAGACC
GTCGCTGTCGGTGTCATCAAGTCCGTCGACAAGTCCACGACACTGCCGGT
AAGGTCACCAAGKCCGCCGYCAAGGCTGGTGCCAAGAAATAAACTTATT
TATG:AATGA::CGA:CCT:TCA:G:TBGGATSTTGCGASTTTG::WT:T
CAYGCTCA:TGAGGCTGATC:T:ACTGGCTT:GT:ACGCC:GAATCGATC
AT:TTG:CA:TGAG:C:AC:TC:GKGTAATGACT:TGSA:G:A:KT:C:T
TSAGA:G:ATWTT:CAAATGCCT:GCTGATS:A:C:GTTGT:G:GCA:CA
TCA:C:ATA:GAACACT:TMGTCKA::G:AA:AT:G:ACTTC:ARAG:AA
AAAAAAAAAAACAW:GT:CATG:ACCAAACGCCGAGATCACTTCTGAG:
GACTCTA:TGTAG:ACTAAAGC:ACAT:GT:CAAGAATTTTTTGAGTTA
CGAAATCCCAAACCGTCATTTCATCATGTGCCCCAATAAAAACCGAGTAC
TCTTTTGTGATAAAGCCAAAATTGACCGGAAAACCTGCGTTTGCGAACGA
GGAAAGTGCCCAAGATGCTACGACATGCTTCCTGGCTTGTCGTGGCTCGA
CATTAGATGTTTGCTGKTTGGTTGATCGCAGCVTYATATTTCTTTKGGCS
```

```
GGCCCCTTGGCCACGCGGGRACCTTGGGTGACCCTTGSCCCTGGGGTACC
CTGGGGACTTGGTCGACGGCTCTTGATGACACCGAACAGCGACGGTCTGA
CGCATGTCACGGACGGCGAAACGACCAAGGGGAGGGTACTCGGAGAAAGT
CTCGACACACATGGGCTTGGACTCGTSCGCBCMMGRATMMCTAGCAGACC
GGRGG
```

Consensus Sequence of GA

```
CCACGCGTCCGCCCTTTTCTGCCCAACAACTTTCCT:CTCYBTCAACGAT
CTWCT::TTTCC:CA:TCAACT:T:GTCGCCTG:CAACA::A:TCTCT:G
C:TCTA:CATCT::TCAG:A:TCTAT::C::ATTCCTCC:GCGACTT:TC
G:C:GA:TTC:TTCT:WTC:TCCTGAC:CT:TG:ATT:CA:TC::CG:::
C:C::AG:C:TCTC:TTM:ATCTCC:CTATTCCACT:A:CACA:CCT:TA
:ATCMATCA:CGATGGAGGAAGAAGTCGCWGCTC:TCGTCATYGACAATGG
TTCGGGTATGTGCAAGGCCGGTTTCGCCGGTGACGATGCTCCCCGAGCTG
TCTTCCCTTCCATTGTCGGTCGCCCCCGTCACCATGGTATCATGATTGGT
ATGGGCCAGAAGGACTCGTACGTTGGTGATGAGGCCCAGTCCAAGCGTGG
TATCCTCACTCTGCGGTACCCCATCGAGCACGGTGTYGTCACCAACTGGG
ACGA:CATGGAGAAGATCTGGCACCACACCTTCTACAACGAGCTGCGTGT
CGCCCCCGAGGAGCAC:CCCGTCCTGCTGACTGAGG:CTCCCATCAACCC
CAAGTCCAACCGTGAGAAGATGACGCAGATCGTC:TTCG:AGACCTTCAA
CGCCCCCGCCTTCTACGTCTCCATCCAGGCCGTKCTGTCCCTGTACGCCT
CCGGTCGTACCACTGG:TATCGTGCTCGACTCYGGTGACGGTGTTACTCA
CGTTGTGCCCATCTACGAGGGTTTCKCCCCTKCCCCACGCCATTGCCCGTG
TCGACATGGCTGGTC:GTG:A:CTTG:A:CCG::AC:T::ACCTG:ATGA
AGA:TCTTGGCTGAGCGCGGTTACA:CCTT:CTCC:ACCAC::T:GCCGA
GCGWGAAATC:GTC:CGTGA:CATCAAGGAGAAGCTCT:::GCTACGTCG
CCCTT:::GA:CTTCGAGCAGGAGATCCAGACTGCTGCCCAGTCCTCCAG
C:YTGGAGAAGTCCTACGAGCTTCCCGACGGACAGGTTATCACCATCG:G
CAACGAGCGC:T:TCCG:TG:CT:CCTGAGGCTCTGTTCCAGCC::TTCT
GT:CC:TGGGTCTTGAGA:GCGG:TGGTATCC:ACGT:CACCACTTTCAA
CTCCATCATGAAGTGTGATGTCGA:TGTCCGAAAGGATCT:GTACGGCAA
CATTGTCATGTCGGTGG:TACCACC::ATG:TACCC:TGGTATCTCCGA
C:CGTATGCA:GAAG:GAGATCACTGCT:CTTGCCCCK:TCCTCSATGAA
GGTCAAGATCATTGCTCCTCCCGAGCGCAAGTACTCCGTCTGGATCGGTG
GTTCCATTCTCGCTT:CG:C::TGTCGACCTT:CCAGCAGATGTG::GAT
CTCGAAGCAGGAGTACGACGAGAGCGGACCTTCSATCGTSCACCGCAAGT
GCTTCTAAGC:G:CCTGACCG:A:CGA:TT::GTGC:TCCAACT:CG::C
:TT:ACGAA:CTG:GAK:CAGAA:ATGTC:GCGA:CAG:ACGC:TA:AGC
:KTCGDGAGG:TTG:GG:T:GCTT:CGAAG:CTCG:TCCGAAACTCGTRT
CTG:CG:AAC:A:TTTA::TTACATG:G::TCGA:T:GAGTSAACGTTGC
GCATG:TACG:AGAGATG:GATGGCCTGWT:T:T:CTTGCAGGTCGAGTA
C::AATG:CGT::CTAGGGC:TASAAG:BCGA:GGTTGACATAC:GAATA
:CG:TGTCTACTW::TCC::G:C:::TTAGARCTG:ACGACA:T:AW:TC:
GAGGGGTTGA:TCAT:GCARCGYGAG::T::CHG:TC:CC:TTGCT:CTA
GAGAATCRAMTTAMAWGGTMGWAAM:TGA:AAAGAGBTCRGTGGMCATCC
TGSCRMRCARTRAWMSATMYGMYAACGMMAMWMARWARAMRWRDMAMMWW
MAAAAAAAAAAAAAAAAAAAAAAAAAAAAAAAAAAAAAAAAAAAGGGC
GGCCGCTCTAN
```

Consensus Sequence of Hsp

```
GCACGAGGAGAAGGTTGAGGGTGAGCGCAACGTCCTCATCTTCGATCTT
GGYGSWSGWRSCTTCGATGTCTCTCTCCTTACCATTGAGGAGGGTATCTT
CGAGGTCAAGTCTACTGCCGGTGACACTCACTTGGGTGGTGAAGATTTCG
ACAACCGCCTCGTTAACCACTTCGTTAACGAGTTCAAGCGAAAGCATAAG
AAGGATCTAAGCACCAACGTCCGTGCTCTTCGACGTCTCCGAACCGCTTG
TGAGCGCGCCAAGCGAACTCTCTCTTCTTCCGCTCAGACCTCCATTGAGA
TCGACTCKCTSTWCGAGGGTATTGACTTCTACACCTCCATCACCCGTGCC
CGTTTCGAGGAGCTCTGCCAGGATCTCTTCCGATCCACCATCCAGCCCGT
CGACCGTGTCCTTACCGACGCCAAGATCGACAAGTCCCTBGTCCACGAGA
TCGTCCTCGTYGGYGGWTCYACCCGTATCCCCCGTGTCCAGAAGCTCATC
ACCGACTACTTCAACGGAAAGGAGCCCAACAAGTCCATCAACCCYGATG
AGGCTGTTGCCTACGTGCTGCCGTCCAGGCTGCCATTCTCTCTGGTGAC
ACCACCTCCAAGTCCACCAACGAGATCCTGCTYCTCGATGTCGCCCCSCT
STCTCTCGGTATCGAGACCGCTGGTGGTATGATGACCAAGCTCATCCCCC
GCAACACCACCATCCCCACCAAGAAGTCYGAGGTCTTCTCCACCTTCTCC
GACAACCAGCCTGGTGTGCTCATCCAGGTCTACGAGGGTGAGCGCCAGC
GCACCAAGGACAACAACCTSCTGGGCAAGTTCGAGCTTACCGGCA:TCCC
MCCTGCTCCCCGTGGTGTTCCCCAGATTGAGGTCACCTTCGACCTSGATG
CCAACGGTATCATGAACGTCTCCGCCGTCGAGAAGGGCACCGGCAAGAC
CAACAAGATTGTCATCACCAACGACAAGGGCCGYCTGTCCAAGGAGGAG
ATYGAGCGCATGCTTGCYGAGGCCGAGAAGTACAAGGAGGAGGATGAG
GCYGAGGSCRMCCGTGTCTCTGCCAAGAACGGCCTYG:AGTCKTACGCCT
ACTCCCTSCGCAA:CACCCTSTCCG:ACYCCAAGGTCGASG:AGAAGCT:
TGAKGCTKCCGACAAGGAGAMSCTCAMYGCTGAGATYRACAAGRTYGTCC
AGCTGGCTYGAYGASARCCAGCAGGCTACYMRKGAGGAGTAYGAGGAGC
ACCAGAAGGAGCTYGAGGSYRWKGCYAACCCCATCATGATGAATTCTA
CGGAGCTGSTGGTGAGGGYGCTCCCGGTGGCATGCCCGGYRYRCCCGGTS
GTGCCCCTGGTGGCTTCCCTGGTGCYGGTGGCCCYGCYCCYGGYGCCGG
YGGYGACGATGGYCCCACGTCGAGGAGGTCGACTAAAYWMYTYGMTA
CYCYWRTAMCATCAKTCYCKAMTTSTWKWKYGRKCAYAKMTSSRTKKK
TWTWATGCGGWKKYTAGTMGTTTKMAYGSKMTGGRTSWGATTASATTG
TTCMTTTTCTYCWRTTTTTMTCGTAAYGACWTYACGRWTRKRAAAAGTC
```

-continued

WMMGGYGVTYYATRYACGTGGKGRWTGTATWTYAATTAGRATCWTWC

AWTSRDAAMAAMARWWMAAAAWAAAAAAAACTCGAAACTAGTTCTCT

CTCTCTCTCCTCGTGC

Consensus Sequence of Rho

AATCCATMACCATGGCTGAAATCCGCCGAAAGCTCGTCATTGTCGGHGA

YGGTGCTTGTGGTAAGACYTGTTTGTTGATTGTCTTCTCCAAGGGCACHT

TCCCMGAGGTCTACGTCCCMACCGTCTTCGAGAACTATGTCGCCGATGTC

GAGGTCGATGGCAAGCACGTCGAGCTCGCGCTATGGGATACBGCTGGTC

AGGAGGATTACGACCGTCTTCGACCTCTCTCATACCCCGACTCSCACGTT

ATCCTGATCTGCTTCGCCGTTGACTCTCCCGATTCCCTCGAYAACGTYCA

GGAGAAGTGGATCTCCGAGGTCCTSCAYTTCTGCCAGGGTCTCCCTATCA

TCCTTGTCGGCTGCAAGAAGGATTTGCGAYACGACCAGAAGACCATTGA

GGAGCTCCACAAGACCASCCAGAASCCCGTCACCCCWGARCAGGGTGAA

GAGGTCCGCAAGAAGATTGGTGCTTACAAGTATCTTGAGTGCTCAGCCAA

GACCAATGAAGGTGTCCGYGAGGTGTTCGAGCACGCCACTCGCGCYGCT

CTCCTGACGCGGAAGAAGCAGAAGAAGCGCGCAAG

Employing the BLAST algorithm (<http colon slash slash>www <dot>ncbi <dot>nlm <dot>nih <dot>gov <slash>blast <slash>Blast <dot>cgi), the sequence with the highest sequence homology to the respective consensus sequence (SEQ IDs NOs: 1-5) was determined from the above-mentioned COGEME or NCBI sequences:

| GA: | GzCon[0219] | (95% identity to GA consensus sequence) |
| EF1: | GzCon[0015] | (91% identity to EF1 consensus sequence) |
| AAC: | FsCon[0026] | (93% identity to AAC consensus sequence) |
| Hsp: | GzCon[2886] | (92% identity to Hsp consensus sequence) |
| Rho: | FsCon[0840] | (93% identity to Rho consensus sequence) |

Suitable regions for the identification of siRNA target sequences within said sequences were—in turn—determined employing the RNAiscan-algorithm (<http colon slash slash>bioinfo2<dot>noble <dot>org). Thereby, the target sequences were selected such that no or only minimal "cross-silencing" to corresponding sequences from barley and/or wheat was to be expected.

Primer were derived from the respective target sequences, and fragments having about 300-350 bp (SEQ ID NOs: 6-11) were isolated from *Fusarium* cDNA and/or DNA samples, and cloned in RNAi vectors (see below). In the case of GA, two different GA fragments ("GA":300 bp; "GA-1":350 bp) may be presented.

The sections within the consensus sequences, to which the above-mentioned contigs show the described high homology, i.e. the conserved regions within the consensus sequences, are listed as SEQ ID NOs: 12-16 further below.

A1. Preparation of the "Entry Vector" (pIPKTA38)

Bacteria, which contained the plasmid, were grown in LB+kanamycin (50 µg/mL). Plasmid DNA was prepared with the Jetstar midi DNA kit.

A control digestion with the restriction enzyme Apa I was carried out in the following. The DNA concentration was measured and adjusted to 150 ng/µL subsequently.

A2. Preparation of the "Destination Vectors"

The vectors pIPKb007, pIPKb010 and GER4 (p6UGLP4deltaSwaIntronRNAi) were used as "destination vectors". Bacteria, which contained the respective plasmid, were grown in LB+spectinomycin (100 µg/mL). Plasmid DNA was prepared with the Jetstar midi DNA kit. The plasmid preparations were digested for control with EcoR V (bands: pIPKb007-12039, 3953 bp; pIPKb010-12039, 3821 and 1148 bp; GER4-12039, 3869 and 1721 bp).

The DNA concentration was measured and adjusted to 150 ng/µL.

A3. PCR Amplification of the Target Sequences of Conserved Fungal Genes

Fragments, which were amplified by PCR from *Fusarium culmorum* DNA/cDNA, of about 300 bp length from the coding sequence regions from the selected conserved fungal genes were fist ligated in pIPKTA38 as entry vector (see FIGS. 1 and 2). For this purpose, various enzymatic cleavage sites (Swa I, EcoR V, Sma I) within the multiple cloning site were used. Said enzymatic cleavage sites were selected according to the desired sequence combination of the RNAi target constructs (see table 5). The ligation of the first sequence took place at the Swa I site of pIPKTA38. In insert two further sequences, the pIPKTA38 construct was used, which contained the first successfully inserted sequence. Said resulting construct was obtained by two further ligations to form a construct comprising three different sequences (see FIG. 2).

"Master Mixes" for 20 μL PCR Reactions with Two Specific Primers

Specific primers were designed in order to amplify ~300 bp fragments from *Fusarium culmorum* DNA or cDNA. The melting temperature (Tm) of the primer was~65° C.

A "master mix" (see table 1) was prepared, and 3.75 μL/well were added to wells of a 96-well PCR plate. 8.5 μL "target"-specific "forward" and "reverse" primer each were added to each well.

TABLE 1

Composition of master mix:

| Component | 1x | 10x |
|---|---|---|
| Thermal ace buffer (10×) | .2 μL | 20 μL |
| dNTPs (50x, 10 mM each) | 0.5 μL | 5 μL |
| Thermal Ace DNA polymerase (2 U/μL) | 0.25 μL | 2.5 μL |
| Template (Fusarium culmorum DNA) | 1.0 μL | 10 μL |
| | 3.75 μL Master mix per well | |
| Target-specific primer - forward (1 μM) | 8.5 μL | |
| Target-specific primer - reverse (1 μM) | 8.5 μL | |

PCR Cycle Conditions

| | | |
|---|---|---|
| 95° C. | 3 min | |
| 95° C. | 30 sec | 30 Cycles |
| 65° C. | 30 sec | 30 Cycles |
| 74° C. | 60 sec | 30 Cycles |
| 74° C. | 10 min | |
| 4° C. | Pause | |

Purification of the PCR Product

30 μA, $H_2O$ were added to each PCR reaction in order to adjust to a total volume of 50 μl. Purification was carried out using the Qiagen MinElute UF 96-well kit, wherein 20 μL $H_2O$ were used for elution subsequently (see Qiagen MinElute protocol). For control, 2 μL each of the purified PCR product were separated by agarose gel electrophoresis.

A4. Cloning of the PCR Products

A ligation mix was prepared (see table 2), 6 μA, each of this ligation mix was added to each well and 4 μl of the purified PCR product were added.

The samples were incubated for 1 h at 25° C. and the reaction was stopped by heating up to 65° C. for 10 min subsequently. 5 μL Swa I/EcoR V/Sma I-mix (see table 3) each was added to each well, following by an incubation at 25° C. for 1 h. Next, the ligation samples were transformed into competent bacteria and suitable clones were isolated after miniprep and control digestion.

TABLE 2

Ligation mix for 10 μL reactions (6 μL mix + 4 μL PCR product per reaction)

| Components | 1x |
| --- | --- |
| $H_2O$ | 1 μL |
| 1) pIPKTA38 (150 ng/μL) | 1 μL |
| 2) pIPKTA38_target1 (150 ng/μL) | |
| 3) pIPKTA38_target1_target2 (150 ng/μL) | |
| Ligation buffer (10×) | 1 μL |
| 50% PEG 4000 | 1 μL |
| NaCl (0.5M) | 1 μL |
| 1) Swa I (10 U/μL) | 0.5 μL |
| 2) EcoR V (10 U/μL) | |
| 3) Sma I (10 U/μL) | |
| T4 DNA ligase (5 U/μL) | 0.5 μL |
| PCR product (purified) | 4 μL |
| 1) target 1 | |
| 2) target 2 | |
| 3) target 3 | |

TABLE 3

Swa I/EcoR V/Sma I mix (5 μL per reaction)

| Components | 1x |
| --- | --- |
| 1) Swa I buffer (10×) | 0.5 μL |
| 2) EcoR V buffer (10×) | |
| 3) Sma I buffer (10×) | |

TABLE 3-continued

Swa I/EcoR V/Sma I mix (5 μL per reaction)

| Components | 1x |
| --- | --- |
| NaCl (0.5M) | 1 μL |
| $H_2O$ | 3 μL |
| 1) Swa I (10 U/μL) | 0.5 μL |
| 2) EcoR V (10 U/μL) | |
| 3) Sma I (10 U/μL) | |

A5. LR Reaction

According to their purpose, the constructs with one or three sequence fragments (targets) were transferred from the intermediate vector pIPKTA38 (entry vector) to a RNAi vector using the LR clonase system. pIPKb007 (formerly p6UUbiRNAi), pIPKb010 (formerly p6U-pGSTA1-RNAi) and p6UGLP4deltaSwaIntronRNAi (p6UGer4deltaSwaIntronRNAi) were used as RNAi vectors (destination vector).

A graphic representation of the components of all three vectors of the triple target RNAi constructs can be found in the annex, where as example the sequence combination of gamma-actin, RhoGTPase and the mitochondrial heat shock protein chaperone 70 (GA-Rho-Hsp) is shown.

Master Mixes for 6 μL LR Reactions

TABLE 4

LR master mix (5 μL master mix + 1 μL IPKTA38_target1_target2_target3 DNA per reaction).

| Component | 1x | for 96 samples |
| --- | --- | --- |
| 1) pIPK007 (150 ng/μL) | 1 μL | 100 μL |
| 2) pIPK010 (150 ng/μL) | | |
| 3) GER4 (p6UGLP4deltaSwaIntronRNAi) (150 ng/μL) | | |
| $H_2O$ | 3 μL | 200 μL |
| LR clonase mix II | 1 μL | 80 μL |
| | | 5 μL Master mix per well |
| pIPKTA38_target1_traget2_target3 | | 1 μL per reaction |

Incubation at room temperature over night (or at least 6 h).

TABLE 5

Overview of the RNAi constructs in combination of three different vector systems, five different conserved fungal proteins, and three different enzyme cleavage sites for the ligation of the respective RNAi targets.

| | | Insertion of the RNAi sequence (target) into enzymatic cleavage site | | |
| --- | --- | --- | --- | --- |
| No. | Vector system | Swa I target 1 | EcoR V target 2 | Sma I target 3 |
| 1 | pIPKb007 | GA (gamma-actin) | | |
| 2 | pIPKb007 | AAC (mitochondrial ADP/ATP carrier) | | |
| 3 | pIPKb007 | Hsp (mitochondrial heat shock protein chaperone) | | |
| 4 | pIPKb007 | Rho (Rho-GTPase) | | |
| 5 | pIPKb007 | EF1 (elongation factor 1) | | |
| 6 | pIPKb007 | GA | AAC | Rho |
| 7 | pIPKb007 | GA | AAC | Hsp |
| 8 | pIPKb007 | GA | AAC | EF1 |
| 9 | pIPKb007 | GA | Rho | EF1 |
| 10 | pIPKb007 | GA | Rho | Hsp |
| 11 | pIPKb007 | AAC | Rho | EF1 |
| 12 | GER4 (p6UGLP4deltaSwaIntronRNAi) | GA | AAC | Rho |
| 13 | GER4 (p6UGLP4deltaSwaIntronRNAi) | GA | AAC | Hsp |

TABLE 5-continued

Overview of the RNAi constructs in combination of three different vector systems, five different conserved fungal proteins, and three different enzyme cleavage sites for the ligation of the respective RNAi targets.

| | | Insertion of the RNAi sequence (target) into enzymatic cleavage site | | |
|---|---|---|---|---|
| No. | Vector system | Swa I target 1 | EcoR V target 2 | Sma I target 3 |
| 14 | GER4 (p6UGLP4deltaSwaIntronRNAi) | GA | AAC | EF1 |
| 15 | GER4 (p6UGLP4deltaSwaIntronRNAi) | GA | Rho | EF1 |
| 16 | GER4 (p6UGLP4deltaSwaIntronRNAi) | GA | Rho | Hsp |
| 17 | GER4 (p6UGLP4deltaSwaIntronRNAi) | AAC | Rho | EF1 |
| 18 | pIPKb010 | GA | AAC | Rho |
| 19 | pIPKb010 | GA | AAC | Hsp |
| 20 | pIPKb010 | GA | AAC | EF1 |
| 21 | pIPKb010 | GA | Rho | EF1 |
| 22 | pIPKb010 | GA | Rho | Hsp |
| 23 | pIPKb010 | AAC | Rho | EF1 |

TABLE 6

Overview of further RNAi constructs in combination of three different vector systems, five different conserved fungal proteins, and three different enzyme cleavage sites for the ligation (4. Cloning of the PCR products) of the respective RNAi targets.

| | | Insertion of the RNAi sequence (target) into enzymatic cleavage site | | |
|---|---|---|---|---|
| No. | Vector system | Swa I target 1 | EcoR V target 2 | Sma I target 3 |
| 24 | pIPKb007 | GA-1 (gamma-actin) | | |
| like 2 | pIPKb007 | AAC (mitochondrial ADP/ATP carrier) | | |
| like 3 | pIPKb007 | Hsp (mitochondrial heat shock protein chaperone) | | |
| like 4 | pIPKb007 | Rho (Rho-GTPase) | | |
| like 5 | pIPKb007 | EF1 (elongation factor 1) | | |
| 25 | pIPKb007 | AAC | GA-1 | Rho |
| 26 | pIPKb007 | AAC | GA-1 | Hsp |
| 27 | pIPKb007 | AAC | GA-1 | EF1 |
| 28 | pIPKb007 | Rho | GA-1 | EF1 |
| 29 | pIPKb007 | Rho | GA-1 | Hsp |
| 30 | pIPKb007 | Rho | AAC | EF1 |
| 31 | GER4 (p6UGLP4deltaSwaIntronRNAi) | AAC | GA-1 | Rho |
| 32 | GER4 (p6UGLP4deltaSwaIntronRNAi) | AAC | GA-1 | Hsp |
| 33 | GER4 (p6UGLP4deltaSwaIntronRNAi) | AAC | GA-1 | EF1 |
| 34 | GER4 (p6UGLP4deltaSwaIntronRNAi) | Rho | GA-1 | EF1 |
| 35 | GER4 (p6UGLP4deltaSwaIntronRNAi) | Rho | GA-1 | Hsp |
| 36 | GER4 (p6UGLP4deltaSwaIntronRNAi) | Rho | AAC | EF1 |
| 37 | pIPKb010 | AAC | GA-1 | Rho |
| 38 | pIPKb010 | AAC | GA-1 | Hsp |
| 39 | pIPKb010 | AAC | GA-1 | EF1 |
| 40 | pIPKb010 | Rho | GA-1 | EF1 |
| 41 | pIPKb010 | Rho | GA-1 | Hsp |
| 42 | pIPKb010 | Rho | AAC | EF1 |

A6. Materials
Jetstar Plasmid Midi prep kit
Genomed
Cat. No. 210250 (250 midipreps)
NucleoSpin Robot-96 plasmid kit
Macherey-Nagel
Cat. No. 740708.4 (4×96 minipreps)
Qiagen MinElute UF 96-well
Qiagen
Cat. No. 2853 (4×96)
Thermal ace DNA polymerase kit
Invitrogen Cat. No. E1000 (1000 U)
Library Efficient DB3.1 competent cells
Invitrogen
Cat. No. 11782-018
Gateway® LR Clonase™ II enzyme mix
Invitrogen
Cat. No. 11791-100 (100 reactions)
T4 DNA ligase (5 U/μL)
Fermentas
Cat No. EL0331 (1000 U)
Swa I (10 U/μL)
New England BioLabs
Cat. No. R0604S (2000 U)
EcoR V (10 U/μL)
Fermantas
Cat. No. #ER0301 (2000 U)
Sma I (10 U/μL)
Fermantas
Cat. No. #ER0661 (1200 U)
Vectors
pIPKTA38—Gateway entry vector, kanamycin resistance.
pIPKb007—binary RNAi vector, spectinomycin resistance. ccdB negative selection marker (needs DB3.1 cells), chloramphenicol resistance (not tested), ubiquitin promotor.
pIPKb010—binary RNAi vector, spectinomycin resistance. ccdB negative selection marker (needs DB3.1 cells), chloramphenicol resistance (not tested), GstA1 promotor.
GER4 (p6UGLP4deltaSwaIntronRNAi)—binary RNAi vector, spectinomycin resistance. ccdB negative selection marker (needs DB3.1 cells), chloramphenicol resistance (not tested), GER4 promotor.

B. TransGen Test and TIGS Protocol

Preparation of the Plant Material:

Barley was cultivated in IPK cereal soil for 7 days without fertilization in a Sanyo phyto-cultivator, at constantly 20° C., 60-70% relative humidity and a 16 h light-cycle. Primary leaves (about 7 cm) were cut off and were arranged in parallel on a phytoagar Petri dish (adaxial side up). Thereby, magnetic stirrers were put onto the leaves such that they repel each other.

Coating of Gold Particles with DNA or RNA:

7 μL=7 μg DNA (plasmid) were used per bombardment. A Bio-Rad Hepta-Adaptor (7 macro carrier slides) was used.

| | | |
|---|---|---|
| 7.0 μl | pUbiGUS (reporter gene) | |
| 0.7 μl | pUbi-Mlo-nos (resistance neutralization) | |
| 7.0 μl | pIPK007_Mlo, pIPK010_Mlo, Ger4_Mlo (resistant control) | |
| Sum: 14.7 μl | | |

Per bombardment, N μL 1 M Ca(NO$_3$)$_2$ pH 10 were added drop wise to 87.5 μL (gold particles, 25 mg/mL in 50% of glycerol; storage at 4° C.) coating suspension during vortexing (N=volume of DNA in μL). The particle suspension was left for at least 10 min at room temperature and was occasionally tipped. The suspension was centrifugated (15 sec, 14000 rpm) and the supernatant was removed with a pipette and discarded. The pellet was washed with 500 μL ethanol (70%), and the ethanol was removed with a pipette. The pellet was again washed with 500 μL ethanol (absolute) and resuspended in 30 μL ethanol (absolute) subsequently.

Coating of Macro Carrier:

Tensile disks and macro carriers were placed in ethanol (absolute) for 30 sec, subsequently dried at room temperature, and placed in the macro carrier holder using a pipette. The tube containing the coating suspension (DNA/particle mixture) was placed in an ultrasonic bath for 3 sec, and the coating suspension was mixed with a pipette subsequently. 3 μL of the coating suspension were applied to each macro carrier by pipette and the suspension was left to dry for 2 min to 5 min.

Biolistic Transformation:

Leaves and macro carrier holder with the treated macro carriers as well as grids (Hepta Stop Screen) were placed in the chamber for biolistic transformation. Vacuum was applied for biolistic transformation, wherein the bombardment was made at a pressure of 27.5 mm Hg.

Incubation and Inoculation of the Leaves with Mildrew:

Bombarded leaves were first incubated for 4 h in slightly opened Petri dishes. 24 h after the bombardment, the leaves were transferred in large, square Petri dishes containing 1% w/v phytoagar with 20 ppm of benzimidazole. Thereby, leaves of all preparations were mixed thoroughly. For inoculation, open Petri dishes were put in dishes with nylon nets (100 μm aperture mesh width) stretched thereover. The leaves were inoculated with mildrew (about 150-200 conidia/mm$^2$). For inoculation, conidia as fresh as possible were used, i.e. either from older plants, which were shaken 24 h-48 h prior to inoculation, or from fresh plants, which were inoculated seven days before. The dishes were placed in the incubation chamber, subsequently.

GUS Staining (for Staining the Transformed Cells):

48 h after inoculation, the leaves were collected, the leaf tips were cut off and the resulting leaves were transferred to Greiner tubes containing 10 mL of X-glucose solution. The tubes were placed in a suction bottle and vacuum was applied thereto 2-3 times. The infiltration is complete, once the leaves become transparent and start to sink. The X-glucose solution was refilled to 14 mL and the tubes were sealed. The tubes were incubated over night at 37° C. in the incubator.

TCA Staining:

The leaves were placed in destaining solution (7.5% TCA, 50% methanol) for 10 min. Leaves were washed with aqua destillata, subsequently. Then, the leaves were carefully removed from the tube and were placed onto an object slide with their adaxial side facing upwards.

200 μL aqua destillata were added to each object slide and the cover glass was carefully applied.

Solutions:

Gus Staining Solution (X-Glucose Solution):
  100 mM trisodium phosphate, final pH 7.0
  10 mM sodium EDTA
  1.4 mM potassium hexacyanoferrate(II)
  1.4 mM potassium hexacyanoferrate(III)
  0.1% triton X-100
  20% methanol
  1 mg/mL X-glucose Ca(NO$_3$)$_2$
  23.61 g Ca(NO$_3$)$_2$ per 100 mL millipore water=1M
  by addition of 0.1 M KOH set ph 10

Benzimidazole Stock Solution
  40 mg/mL of benzimidazole in ethanol (absolute)

Phytoagar
  0.5-1% (w/v) agarose in millipore water with 50 μL of benzimidazole stock solution (see above)

Preparation of Gold Suspension:
  27.5 mg of Bio-Rad gold particles (1 μm diameter, prod. No. LLP892) were vortexed in 1 mL sterile H$_2$O and treated with ultrasonic for 20 sec. After centrifugation (30 sec. 14.000 rpm), the supernatant was removed with a pipette, the particles were again vortexed in 1 mL of sterile $H_2O$, treated with ultrasonic for 20 sec. and centrifugated (as above). The supernatant was removed and 1 mL of EtOH absolute was added to the pellet and the sample was treated with ultrasonic for 20 sec. After another centrifugation (as above), the supernatant was removed with a pipette and the pellet was dried with open lid at 40° C. for about 20 min in a thermomixer. After addition of 1 mL 50% sterile glycerol, the preparation was vortexed and treated with ultrasonic until the pellet was suspended. The suspension was stored at −20° C.

C. Experiment for Primary Data Acquisition

For checking the resistance effect of the RNAi constructs, in particular the single and triple constructs in combination with the pIPKb007 vector were used in the transient experiments.

The barley plants used (*Hordeum vulgare*, cultivar, Ingrid BC mlo5') were cultivated in soil without fertilization in a phyto-cultivator (from Sanyo, at constantly 20° C., 60-70% rel. humidity, 16 h light). On the day of bombardment, plants were 7 days old. The primary leaves were cut off, placed on 0.5% phytoagar with 200 ppm benzimidazole and bombarded with 2.2 mg of gold particles, which were coated with a mixture of 7 μg reporter gene vector (pUbiGUS), 0.7 μg pUbi-Mlo-nos (resistance neutralization) and 7 μg of a control vector (pIPKb007_MLO, pIPKb010_MLO or Ger4_MLO (resistant control) according to the RNAi constructs to be tested) or with a RNAi construct. In closed Petri dishes, the leaves were stored at 20° C. at a north-facing window until inoculation.

One day after bombardment, the leaves were ransferred to 1% phytoagar with 2% benzimidazole. A nylon net (aperture mesh width of 200 μm) was stretched over the leaves, and the same were inoculated with a conidia density of about 200 conidia/$mm^2$. The conidia (from the pathogen *Blumeria graminis* hordei) originated from barley plants (cultivar, Golden Promise'), which were inoculated 6-7 days before. Until GUS staining, the leaves were stored in closed Petri dishes with holes for ventilation at 20° C. at a north-facing window.

About 48 h after inoculation, GUS staining was performed. Said staining was stopped after 20 h by incubation in 7.5% trichloroacetic acid, 50% v/v methanol, and the leaves were bleached.

Every experiment contained 3-4 parallel bombardments to 7 leaf sections each of the HIGS negative control (respective empty vector). Further, each experiment contained 2 parallel bombardments of a TIGS positive control (pIPKb007_MLO, pIPKb010_MLO, Ger4_MLO, causes resistance by inhibiting the Mlo gene of barley). Data per experiment are based on the comparison of the effect of the test constructs with the average value of the 4 negative controls of the respective experiment.

In all test series of the experiments in Ingrid BC mlo5, pUbi-MLO-nos was bombarded as well, which causes a neutralization of the resistance of the Ingrid BCmlo5 cells. This allows for the analysis of haustoria development as well as hyphen development, since hyphens are only able to grow from transformed epithermal cells and thus do not mix with hyphens from adjacent infection events on non-transformed cells.

D. Examples of Use

D1 result of the HIGS Screening

For transient experiments, barley leaves of the sort Ingrid BC mlo5 (*Hordeum vulgare*) were used. Spores of the phytopathogen *Blumeria graminis* f. sp. *hordei* (barley powdery mildrew) were used as inoculum. In said system, all single and triple target RNAi constructs were tested in combination with the vector pIPKb007. In these experiments, it could be shown that a significant infestation-reduced effect is detectable in six out of the tested constructs (see table 8). In order to control the functionality of the system and to measure the resistance effect, a construct having a known resistant Mlo sequence (ubi_mlo) was carried along, which showed in all experiments a significant reduction of the haustoria index with a very high significance ($p=0.0001$). The results demonstrate that the RNAi constructs which are directed against highly conserved target genes of a fungus (in this case: *Fusarium culmorum*) are effective against another fungus (in this case: *Blumeria graminis*).

TABLE 7

Average values, standard deviations and p-values of significant constructs from transient experiments using Ingrid mlo5 (*Hordeum vulgare*) and the pathogen *Blumeria graminis* f. sp. *hordei*

| | Construct (No. cf. tab. 5) (repeats) | | | | | | | |
|---|---|---|---|---|---|---|---|---|
| | pIPKb007 (empty vector) | pIPKb007_mlo | 2 AAC | 3 Hsp | 8 AAC-GA-EF1 | 9 Rho-GA-EF1 | 10 Rho-GA-Hsp | 11 Rho-AAC-EF1 |
| n1 (number of evaluated leaves) | 84 | 64 | 23 | 27 | 29 | 28 | 30 | 22 |
| n2 (number of evaluated GUS cells) | 5967 | 4141 | 1419 | 1598 | 1413 | 1533 | 1533 | 1185 |
| Average value in % (of the haustoria index* in relation to the empty ubi vector (=100%)) | 100 | 41.88 | 56.03 | 78.02 | 82.62 | 74.93 | 72.65 | 69.14 |
| Standard deviation | — | 36.97 | 33.50 | 41.67 | 44.70 | 38.66 | 48.93 | 51.52 |
| p-value from t-test, two tailed | — | <0.0001 | <0.0001 | 0.011 | 0.0455 | 0.002 | 0.0047 | 0.0105 |

*the haustoria index corresponds to the ratio between the number of haustoria formed and the number of the evaluated GUS cells

D2. Production of Transgenic Barley Plants

By way of the above-mentioned vectors or RNAi constructs, transgenic barley plants have been produced by the *Agrobacterium* methodology. Transgenic plants were selected by hygromycin resistance. The following constructs were used:

| Vector (promotor) | RNAi insert(s) |
|---|---|
| pIPKb007(ubiquitin) | AAC |
| | GA-AAC-Rho |
| | GA-AAC-Hsp |
| | GA-AAC-EF1 |
| | GA-Rho-EF1 |
| | GA-Rho-Hsp |
| | AAC-Rho-EF1 |
| | Empty vector |
| pIPKb010 (GSTA1) | GA-Rho-Hsp |
| | AAC-Rho-EF1 |
| | Empty vector |
| p6UGLP4deltaSwaIntronRNAi (GER4) | GA-Rho-Hsp |
| | AAC-Rho-EF1 |
| | Empty vector |

In initial inoculation experiments, plants transgenic for pIPKb007_GA-AAC-Hsp and pIPKb007_GA-AAC-Rho showed resistance to *Fusarium culmorum* and *Blumeria graminis*, compared to wild type plants.

D3. Effect of RNAi Construct Against Barley Mildrew and *Fusarium* Head Blight in Transgenic Plants

| | Fusarium assay (% infected blossoms) | | Mildrew assay (% infected leaf area, rel. to GP) | |
|---|---|---|---|---|
| Sample | MW ± SDM | p | MW ± SDM | p |
| GP (wt) | 5.1 ± 0.5 | | 100 | |
| K26 transgenic | 1.57 ± 0.5 | 0.0256 | 74.8 ± 9.3 | 0.0092 |
| K26 azygous | 3.45 ± 2.56 | NS | 122.8 ± 24.4 | Precipitation |

Four independent transgenic barley lines, which were transformed with construct No. 26 (K26), showed increased resistance to both, *fusarium* head blight and barley mildrew. Azygous segregants of the examined transgenic lines (T1 generation) showed no significant resistance phenotype.

D4. Sequences of the Vectors and Triple Target RNAi Constructs

In the following, the sequences of the triple RNAi-targets are listed, which are inserted into the various vectors using the above-described GATEWAY procedure. The GATEWAY cleavage sites in the binary RNAi vectors are marked in colour code in all 6 different triple combinations (see table 6).

The sequences as well as the components of the three different vectors (pIKPb007, pIPKb010, GER4 (p6UGLP4deltaSwaIntronRNAi)) are annexed as genebank library file.

As an example of the triple target RNAi constructs, the combination of gamma-actin, RhoGTPase and mitochondrial heat shock protein 70 chaperone is presented schematically in all three vector systems.

Colour code within the insert sequences:
GATEWAY Site
E' en R V Site
Swa I Site
Sma I Site Targets of the conserved proteins:
GA
AAC
Rho
EF1
Hsp >AAC insert
GTACAAAAAAGCAGGCTTTAAAGGAACCAATTCAGTCGACCTCGAGCA
CCTGCGCGGCCGCGAATTCGATATCATTTCTTGTAGACGTCGACGAGAC
CGTTGAACTGACGGTCACCACCGGACTTGGCGTTCTTGGCATCGTTGG
CAAGACGAGTACGGGCGTAGTCCAGAGAGTAGACGAAGAGCAGAGA
AGTGGCACCAGCAGCACCACCGGAGGCAAGGTTACCAGCCATCCACA
TGGCGTAGCCATCCTTGTCCTTCTTGTAGCCGAACATCTTCTTGAACTT
GTCACGGAAAGCGAAGTTCAGGGCCTGGGTGGGAAGTATCGGATGA
CGTTGGCGGTGTTTCCTCGCCAGAGGGACATGACACCCTCATCGAAAT
GCCCGGGCGAATTCTCTAGACCCAGCTTT The above-mentioned sequence of the AAC siRNA insert is in antisense orientation (3'-5'), the complementary "sense" sequence (5'-3') corresponds to SEQ ID NO: 6.

>EF1 insert
GTACAAAAAAGCAGGCTTTAAAGGAACCAATTCAGTCGACCTCGAGCA
CCTGCGCGGCCGCGAATTCGATATCATTTGCAGGCAATGTGGGCAGTG
TGGCAATCGAGGACGGGAGCGTAACCAGCACCGACCTGACCGGGGT
GGTTGAGGACGATGACCTGGGCGGTGAAAGAAGCGGCACCCATGGG
GGGGGTCGTTCTTGGAGTCACCAGCGACGTTACCACGTCGGATGTCCT
TGACGGAAACGTTCTTCACGTTGAAACCAACGTTGTCACCGGGCTGTC
CCTCAGTGAGCTGCTCGTGGTGCATCTCAACGGACTTGACTTCAGTGG
TGACGTTGGAAGGAGCGAAGGTAACGACCATACCGGGCTTGATAAAT
GCCCGGGCGAATTCTCTAGACCCAGCTTT The above-mentioned sequence of the EF1 siRNA insert is in antisense orientation (3'-5'), the complementary "sense" sequence (5'-3') corresponds to SEQ ID NO: 7.

>GA insert
GTACAAAAAAGCAGGCTTTAAAGGAACCAATTCAGTCGACCTCGAGCA
CCTGCGCGGCCGCGAATTCGATATCATTTGGAAGAAGGAGCAAGAGCA
GTGATCTCCTTCTGCATACGGTCGGAGAGACCGGGGTACATGGTGGT
ACCACCAGACATGACAATGTTTCCGTAGAGATCCTTTCGGACATCGA
CATCACACTTCATGATGGAGTTGAAAGTGGTGACGTGGATACCACCG
CTCTCAAGACCAAGGACAGAAGGCTGGAAGAGAGCCTCAGGAGCAC
GGAATCGCTCGTTACCAATGGTGATAACCTGACCGTCAGGAAGCTCG
TAAGACTTCTCCAAGCTGGAGCTCTGGGCAGCAGTCTGGATCTCCTG
CTCGAAAATGCCCGGGCGAATTCTCTAGACCCAGCTTT The above-mentioned sequence of the GA siRNA insert is in antisense orientation (3'-5'), the complementary "sense" sequence (5'-3') corresponds to SEQ ID NO: 8

>22GA-1 insert
GTACAAAAAAGCAGGCTTTAAAGGAACCAATTCAGTCGACCTCGAGCA
CCTGCGCGGCCGCTAATTCGATATCATTTGGAAGAAGGAGCAAGAGCA
GTGATCTCCTTCTGCATACGGTCGGAGAGACCGGGGTACATGGTGGT
ACCACCAGACTAAAGACATGTTAGAACAGTTGGAGTGCTTTCGATTT
GCAGAACTTACCATGACAATGTTTCCGTAGAGATCCTTTCGGACATC
GACATCACACTTCATGATGGAGTTGAAAGTGGTGACGTGGATACCAC
CGCTCTCAAGACCAAGGACAGAAGGCTGGAAGAGAGCCTCAGGAGC
ACGGAATCGCTCGTTACCAATGGTGATAACCTGACCGTCAGGAAGCT
CGTAAGACTTCTCCAAGCTGGAGCTCTGGGCAGCAGTCTGGATCTCC
TGCTCGAAAAATGCCCGGGCGAATTCTCTAGACCCAGCTTT The above-mentioned sequence of the GA-1 siRNA insert is in antisense orientation (3'-5'), the complementary "sense" sequence (5'-3') corresponds to SEQ ID NO: 9.

>Hsp insert
GTACAAAAAAGCAGGCTTTAAAGGAACCAATTCAGTCGACCTCGAGCA
CCTGCGCGGCCGCGAATTCGATATCATTTACTTGCCCATGAGGTTGTTG
TCCTTGGTGCGCTGGCGCTCACCCTCGTAGACCTGGATAAGGACACC
AGGCTGGTTGTCGGAGAAGGTAGAGAAGACCTCGGACTTCTTGGTGG
GAATGGTGGTGTTGCGGGGATGAGCTTGGTCATCATACCACCAGCG
GTCTCGATACCGAGAGAGAGGGGGGCGACGTCGAGGAGCAGAATCT
CGTTGGTGGCCTTGCTAGAGGTGTCACCAGAGAGAATAGCAGCCTGG
ACAGCGGCACCGTAGGCAACAGCCTCATCAGGATTGATGGACTTGTT
GGGCTCCTTTCCGTTGAAGTAGTCGGTGATGAGCTTCTGGACACGGG
GATACGGAAATGCCCGGGCGAATTCTCTAGACCCAGCTTT The above-mentioned sequence of the Hsp siRNA insert is in antisense orientation (3'-5'), the complementary "sense" sequence (5'-3') corresponds to SEQ ID NO: 10.

>Rho insert
GTACAAAAAAGCAGGCTTTAAAGGAACCAATTCAGTCGACCTCGAGCA
CCTGCGCGGCCGCGAATTCGATATCATTTTGCTTGTGGTAAAACCTGTTT
GTTGATCGTTTTCTCCAAGGGCACTTTCCCCGAGGTCTACGTCCCCAC
CGTCTTCGAGAACTATGTCGCCGATGTCGAGGTTGACGGCAAGCACG
TCGAGCTCGCCCTATGGGATACTGCTGGTCAGGAGGATTACGACCGT
CTTCGACCTCTCTCTTACCCCGACTCCCACGTTATCTTGATCTGCTTCG
CTGTTGACTCTCCCGACTCTCTCGACAACGTCCAGGAGAAGTGGATCT
CTGAGGTTCTGCACTTCTGCCAGGGKCTCCCTATCATCCTTGTCGGCT
AAATGCCCGGGCGAATTCTCTAGACCCAGCTTT The above-mentioned sequence of the Rho siRNA insert is in antisense orientation (3'-5'), the complementary "sense" sequence (5'-3') corresponds to SEQ ID NO: 11.

>GA_AAC_Rho insert
GTACAAAAAAGCAGGCTTTAAAGGAACCAATTCAGTCGACCTCGAGCA
CCTGCGCGGCCGCGAATTCGATCTTGTAGACGTCGACGAGACCGTTGA
ACTGACGGTCACCACCGGACTTGGCGTTCTTGGCATCGTTGGCAAGAC
GAGTACGGGCGTAGTCCAGAGAGTAGACGAAGAGCAGAGAAGTGGC
ACCAGCAGCACCACCGGAGGCAAGGTTACCAGCCATCCACATGGCGT
AGCCATCCTTGTCCTTCTTGTAGCCGAACATCTTCTTGAACTTGTCACG
GAAAGCGAAGTTCAGGGCCTGGGTGGGGAAGTATCGGATGACGTTGG
CGGTGTTTCCTCGCCAGAGGGACATGACACCCTCATCGATCATTTGGA
AGAAGGAGCAAGAGCAGTGATCTCCTTCTGCATACGGTCGGAGAGA
CCGGGGTACATGGTGGTACCACCAGACATGACAATGTTTCCGTAGAG
ATCCTTTCGGACATCGACATCACACTTCATGATGGAGTTGAAAGTGG
TGACGTGGATACCACCGCTCTCAAGACCAAGGACAGAAGGCTGGAA
GAGAGCCTCAGGAGCACGGAATCGCTCGTTACCAATGGTGATAACCT
GACCGTCAGGAAGCTCGTAAGACTTCTCCAAGCTGGAGCTCTGGGCA
GCAGTCTGGATCTCCTGCTCGAAAATGCCCTGCTTGTGGTAAAACCTG
TTTGTTGATCGTTTTCTCCAAGGGCACTTTCCCCGAGGTCTACGTCCCC
ACCGTCTTCGAGAACTATGTCGCCGATGTCGAGGTTGACGGCAAGCA
CGTCGAGCTCGCCCTATGGGATACTGCTGGTCAGGAGGATTACGACC
GTCTTCGACCTCTCTCTTACCCCGACTCCCACGTTATCTTGATCTGCTT
CGCTGTTGACTCTCCCGACTCTCTCGACAACGTCCAGGAGAAGTGGAT
CTCTGAGGTTCTGCACTTCTGCCAGGGKCTCCCTATCATCCTTGTCGG
CTGGGCGAATTCTCTAGACCCAGCTTT >GA_AAC_mHspCh insert
GTACAAAAAAGCAGGCTTTAAAGGAACCAATTCAGTCGACCTCGAGCA
CCTGCGCGGCCGCGAATTCGATCTTGTAGACGTCGACGAGACCGTTGA
ACTGACGGTCACCACCGGACTTGGCGTTCTTGGCATCGTTGGCAAGAC
GAGTACGGGCGTAGTCCAGAGAGTAGACGAAGAGCAGAGAAGTGGC
ACCAGCAGCACCACCGGAGGCAAGGTTACCAGCCATCCACATGGCGT
AGCCATCCTTGTCCTTCTTGTAGCCGAACATCTTCTTGAACTTGTCACG
GAAAGCGAAGTTCAGGGCCTGGGTGGGGAAGTATCGGATGACGTTGG
CGGTGTTTCCTCGCCAGAGGGACATGACACCCTCATCGATCATTTGGA
AGAAGGAGCAAGAGCAGTGATCTCCTTCTGCATACGGTCGGAGAGA
CCGGGGTACATGGTGGTACCACCAGACATGACAATGTTTCCGTAGAG
ATCCTTTCGGACATCGACATCACACTTCATGATGGAGTTGAAAGTGG
TGACGTGGATACCACCGCTCTCAAGACCAAGGACAGAAGGCTGGAA
GAGAGCCTCAGGAGCACGGAATCGCTCGTTACCAATGGTGATAACCT
GACCGTCAGGAAGCTCGTAAGACTTCTCCAAGCTGGAGCTCTGGGCA
GCAGTCTGGATCTCCTGCTCGAAAATGCCCCTCACCCTCGTAGACCTG
GATAAGGACACCAGGCTGGTTGTCGGAGAAGGTAGAGAAGACCTCGG
ACTTCTTGGTGGGAATGGTGGTGTTGCGGGGATGAGCTTGGTCATCA
TACCACCAGCGGTCTCGATACCGAGAGAGAGGGGGGCGACGTCGAG

```
GAGCAGAATCTCGTTGGTGGCCTTGCTAGAGGTGTCACCAGAGAGAA
TAGCAGCCTGGACAGCGGCACCGTAGGCAACAGCCTCATCAGGATTG
ATGGACTTGTTGGGCTCCTTTCCGTTGAAGTAGTCGGTGATGAGCTTCT
GGGGGCGAATTCTCTAGACCCAGCTTT
>GA_AAC_EF1 insert
TACAAAAAAGCAGGCTTTAAAGGAACCAATTCAGTCGACCTCGAGCAC
CTGCGCGGCCGCGAATTCGATCTTGTAGACGTCGACGAGACCGTTGAA
CTGACGGTCACCACCGGACTTGGCGTTCTTGGCATCGTTGGCAAGAC
GAGTACGGGCGTAGTCCAGAGAGTAGACGAAGAGCAGAGAAGTGGC
ACCAGCAGCACCACCGGAGGCAAGGTTACCAGCCATCCACATGGCGT
AGCCATCCTTGTCCTTCTTGTAGCCGAACATCTTCTTGAACTTGTCACG
GAAAGCGAAGTTCAGGGCCTGGGTGGGAAGTATCGGATGACGTTGG
CGGTGTTTCCTCGCCAGAGGGACATGACACCCTCATCGATCATTTGGA
AGAAGGAGCAAGAGCAGTGATCTCCTTCTGCATACGGTCGGAGAGA
CCGGGGTACATGGTGGTACCACCAGACATGACAATGTTTCCGTAGAG
ATCCTTTCGGACATCGACATCACACTTCATGATGGAGTTGAAAGTGG
TGACGTGGATACCACCGCTCTCAAGACCAAGGACAGAAGGCTGGAA
GAGAGCCTCAGGAGCACGGAATCGCTCGTTACCAATGGTGATAACCT
GACCGTCAGGAAGCTCGTAAGACTTCTCCAAGCTGGAGCTCTGGGCA
GCAGTCTGGATCTCCTGCTCGAAAATGCCCGCAGGCAATGTGGGCAG
TGTGGCAATCGAGGACGGGAGCGTAACCAGCACCGACCTGACCGGG
GTGGTTGAGGACGATGACCTGGGCGGTGAAAGAAGCGGCACCCATG
GGGGGGGTCGTTCTTGGAGTCACCAGCGACGTTACCACGTCGGATGT
CCTTGACGGAAACGTTCTTCACGTTGAAACCAACGTTGTCACCGGGCT
GTCCCTCAGTGAGCTGCTCGTGGTGCATCTCAACGGACTTGACTTCAG
TGGTGACGTTGGAAGGAGCGAAGGTAACGACCATACCGGGCTTGATG
GGCGAATTCTCTAGACCCAGCTTT
>GA_Rho_EF1 insert
GTACAAAAAAGCAGGCTTTAAAGGAACCAATTCAGTCGACCTCGAGCA
CCTGCGCGGCCGCGAATTCGATTCGGCTGTTCCTACTATCCCTCKGGGA
CCGTCTTCACGTCTTGGAGTCTCTAGGTGAAGAGGACCTGCAACAGCT
CTCTCAGCCCTCTCAGTTGTCGCTTCGTCTAGTTCTATTGCACCCTCAG
CCCCATTCTCTCTCCAGCTTCTGCCAGCATTAGGAGGACTGGTCGTCA
TAGGGTATCCCGCTCGAGCTGCACGAACGGCAGTTGGAGCTGTAGCC
GCTGTATCAAGAGCTTCTGCCACCCCTGCATCTGGAGCCCCTTTCACG
GGAACCTCTTTTGCTAGTTGTTTGTCCAAAATGGTGTTCGTATCATTTG
GAAGAAGGAGCAAGAGCAGTGATCTCCTTCTGCATACGGTCGGAGA
GACCGGGGTACATGGTGGTACCACCAGACATGACAATGTTTCCGTAG
AGATCCTTTCGGACATCGACATCACACTTCATGATGGAGTTGAAAGT
GGTGACGTGGATACCACCGCTCTCAAGACCAAGGACAGAAGGCTGG
AAGAGAGCCTCAGGAGCACGGAATCGCTCGTTACCAATGGTGATAAC
CTGACCGTCAGGAAGCTCGTAAGACTTCTCCAAGCTGGAGCTCTGGG
```

```
CAGCAGTCTGGATCTCCTGCTCGAAAATGCCCGCAGGCAATGTGGGC
AGTGTGGCAATCGAGGACGGGAGCGTAACCAGCACCGACCTGACCG
GGGTGGTTGAGGACGATGACCTGGGCGGTGAAAGAAGCGGCACCCA
TGGGGGGGGTCGTTCTTGGAGTCACCAGCGACGTTACCACGTCGGAT
GTCCTTGACGGAAACGTTCTTCACGTTGAAACCAACGTTGTCACCGGG
CTGTCCCTCAGTGAGCTGCTCGTGGTGCATCTCAACGGACTTGACTTC
AGTGGTGACGTTGGAAGGAGCGAAGGTAACGACCATACCGGGCTTGA
TGGGCGAATTCTCTAGACCCAGCTTT
>GA_Rho_mHspCh insert
GTACAAAAAAGCAGGCTTTAAAGGAACCAATTCAGTCGACCTCGAGCA
CCTGCGCGGCCGCGAATTCGATAGCCGACAAGGATGATAGGGAGMCC
CTGGCAGAAGTGCAGAACCTCAGAGATCCACTTCTCCTGGACGTTGTC
GAGAGAGTCGGGAGAGTCAACAGCGAAGCAGATCAAGATAACGTGG
GAGTCGGGGTAAGAGAGAGGTCGAAGACGGTCGTAATCCTCCTGACC
AGCAGTATCCCATAGGGCGAGCTCGACGTGCTTGCCGTCAACCTCGA
CATCGGCGACATAGTTCTCGAAGACGGTGGGGACGTAGACCTCGGGG
AAAGTGCCCTTGGAGAAAACGATCAACAAACAGGTTTTACCACAAGC
AATCATTTGGAAGAAGGAGCAAGAGCAGTGATCTCCTTCTGCATACG
GTCGGAGAGACCGGGGTACATGGTGGTACCACCAGACATGACAATG
TTTCCGTAGAGATCCTTTCGGACATCGACATCACACTTCATGATGGA
GTTGAAAGTGGTGACGTGGATACCACCGCTCTCAAGACCAAGGACA
GAAGGCTGGAAGAGAGCCTCAGGAGCACGGAATCGCTCGTTACCAA
TGGTGATAACCTGACCGTCAGGAAGCTCGTAAGACTTCTCCAAGCTG
GAGCTCTGGGCAGCAGTCTGGATCTCCTGCTCGAAAATGCCCTCAC
CCTCGTAGACCTGGATAAGGACACCAGGCTGGTTGTCGGAGAAGGTA
GAGAAGACCTCGGACTTCTTGGTGGGAATGGTGGTGTTGCGGGGAT
GAGCTTGGTCATCATACCACCAGCGGTCTCGATACCGAGAGAGAGGG
GGGCGACGTCGAGGAGCAGAATCTCGTTGGTGGCCTTGCTAGAGGTG
TCACCAGAGAGAATAGCAGCCTGGACAGCGGCACCGTAGGCAACAG
CCTCATCAGGATTGATGGACTTGTTGGGCTCCTTTCCGTTGAAGTAGTC
GGTGATGAGCTTCTGGGGGCGAATTCTCTAGACCCAGCTTT
>AAC_Rho_EF1 insert
GTACAAAAAAGCAGGCTTTAAAGGAACCAATTCAGTCGACCTCGAGCA
CCTGCGCGGCCGCGAATTCGATTGCTTGTGGTAAAACCTGTTTGTTGAT
CGTTTTCTCCAAGGGCACTTTCCCCGAGGTCTACGTCCCACCGTCTT
CGAGAACTATGTCGCCGATGTCGAGGTTGACGGCAAGCACGTCGAGC
TCGCCCTATGGGATACTGCTGGTCAGGAGGATTACGACCGTCTTCGAC
CTCTCTCTTACCCCGACTCCCACGTTATCTTGATCTGCTTCGCTGTTGA
CTCTCCCGACTCTCTCGACAACGTCCAGGAGAAGTGGATCTCTGAGGT
TCTGCACTTCTGCCAGGGKCTCCCTATCATCCTTGTCGGCTATCATTTC
TTGTAGACGTCGACGACCGTTGAACTGACGGTCACCACCGGACTT
GGCGTTCTTGGCATCGTTGGCAAGACGAGTACGGGCGTAGTCCAGAG
```

```
AGTAGACGAAGAGCAGAGAAGTGGCACCAGCAGCACCACCGGAGGC
AAGGTTACCAGCCATCCACATGGCGTAGCCATCCTTGTCCTTCTTGTA
GCCGAACATCTTCTTGAACTTGTCACGGAAAGCGAAGTTCAGGGCCTG
GGTGGGGAAGTATCGGATGACGTTGGCGGTGTTTCCTCGCCAGAGGG
ACATGACACCCTCATCGAAATGCCCATCAAGCCCGGTATGGTCGTTAC
CTTCGCTCCTTCCAACGTCACCACTGAAGTCAAGTCCGTTGAGATGCA
CCACGAGCAGCTCACTGAGGGACAGCCCGGTGACAACGTTGGTTTCA
ACGTGAAGAACGTTTCCGTCAAGGACATCCGACGTGGTAACGTCGCT
GGTGACTCCAAGAACGACCCCCCCCATGGGTGCCGCTTCTTTCACCG
CCCAGGTCATCGTCCTCAACCACCCCGGTCAGGTCGGTGCTGGTTAC
GCTCCCGTCCTCGATTGCCACACTGCCCACATTGCCTGCGGGCGAATT
CTCTAGACCCAGCTTT
>AAC_GA-1_Rho insert
GTACAAAAAAGCAGGCTTTAAAGGAACCAATTCAGTCGACCTCGAGCACC
TGCGCGGCCGCGAATTCGATCTTGTAGACGTCGACGAGACCGTTGAACTG
ACGGTCACCACCGGACTTGGCGTTCTTGGCATCGTTGGCAAGACGAGTAC
GGGCGTAGTCCAGAGAGTAGACGAAGAGCAGAGAAGTGGCACCAGCAGCA
CCACCGGAGGCAAGGTTACCAGCCATCCACATGGCGTAGCCATCCTTGTC
CTTCTTGTAGCCGAACATCTTCTTGAACTTGTCACGGAAAGCGAAGTTCA
GGGCCTGGGTGGGAAGTATCGGATGACGTTGGCGGTGTTTCCTCGCCAG
AGGGACATGACACCCTCATCGATCATTTGGAAGAAGGAGCAAGAGCAGTG
ATCTCCTTCTGCATACGGTCGGAGAGACCGGGGTACATGGTGGTACCACC
AGACTAAAGACATGTTAGAACAGTTGGAGTGCTTTCGATTTGCAGAACTT
ACCATGACAATGTTTCCGTAGAGATCCTTTCGGACATCGACATCACACTT
CATGATGGAGTTGAAAGTGGTGACGTGGATACCACCGCTCTCAAGACCAA
GGACAGAAGGCTGGAAGAGAGCCTCAGGAGCACGGAATCGCTCGTTACCA
ATGGTGATAACCTGACCGTCAGGAAGCTCGTAAGACTTCTCCAAGCTGGA
GCTCTGGGCAGCAGTCTGGATCTCCTGCTCGAAAATGCCCTGCTTGTGGT
AAAACCTGTTTGTTGATCGTTTTCTCCAAGGGCACTTTCCCCGAGGTCTA
CGTCCCCACCGTCTTCGAGAACTATGTCGCCGATGTCGAGGTTGACGGCA
AGCACGTCGAGCTCGCCCTATGGGATACTGCTGGTCAGGAGGATTACGAC
CGTCTTCGACCTCTCTCTTACCCCGACTCCCACGTTATCTTGATCTGCTT
CGCTGTTGACTCTCCCGACTCTCTCGACAACGTCCAGGAGAAGTGGATCT
CTGAGGTTCTGCACTTCTGCCAGGGKCTCCCTATCATCCTTGTCGGCTGG
GCGAATTCTCTAGACCCAGCTTT
>AAC_GA-1_mHspCh insert
GTACAAAAAAGCAGGCTTTAAAGGAACCAATTCAGTCGACCTCGAGCACC
TGCGCGGCCGCTAATTCGATTGTAGACGTCGACGAGACCGTTGAACTGAC
GGTCACCACCGGACTTGGCGTTCTTGGCATCGTTGGCAAGACGAGTACGG
GCGTAGTCCAGAGAGTAGACGAATAGAAGAGAAGTGGCACCAGCAGCACC
ACCGGAGGCAAGGTTACCGGCCATCCACATGGCGTAGCCATCCTTGTCCT
TCTTGTAACCGAACATCTTCTTGAACTTGTCACGGAAAGCGAAGTTCAGA
```

```
GCCTGGGTAGGGAAGTATCGGATGACGTTGGCGGTGTTTCCTCGCCAGAG
GGACATGACACCCTCATCGATCATTTGGAAGAAGGAGCAAGAGCAGTGAT
CTCCTTCTGCATACGGTCGGAGAGACCGGGGTACATGGTGGTACCACCAG
ACTAAAGACATGTTAGAACAGTTGGAGTGCTTTCGATTTGCAGAACTTAC
CATGACAATGTTTCCGTAGAGATCCTTTCGGACATCGACATCACACTTCA
TGATGGAGTTGAAAGTGGTGACGTGGATACCACCGCTCTCAAGACCAAGG
ACAGAAGGCTGGAAGAGAGCCTCAGGAGCACGGAATCGCTCGTTACCAAT
GGTGATAACCTGACCGTCAGGAAGCTCGTAAGACTTCTCCAAGCTGGAGC
TCTGGGCAGCAGTCTGGATCTCCTGCTCGAAAAATGCCCTCGTAGACCTG
GATAAGGACACCAGGCTGGTTGTCGGAGAAAGTAGAGAAGACCTCGGACT
TCTTGGTGGGAATGGTGGTGTTGCGGGGGATGAGCTTGGTCATCATACCA
CCAGCGGTCTCGATACCGAGAGAGAGAGGGGCAACGTCGAGGAGCAGAAT
CTCGTTGGTGGCCTTGCTAGAGGTGTCACCAGAGAGAATAGCAGCCTGGA
CAGCGGCACCGTAGGCAACAGCCTCATCAGGGTTGATGGACTTGTTGGGC
TCCTTTCCGTTGAAGTAGTCGGTGATGAGCTTCTGGGGGCGAATTCTCTA
GACCCAGCTTT
>AAC_GA-1_EF1 insert
GTACAAAAAAGCAGGCTTTAAAGGAACCAATTCAGTCGACCTCGAGCACC
TGCGCGGCCGCTAATTCGATTGTAGACGTCGACGAGACCGTTGAACTGAC
GGTCACCACCGGACTTGGCGTTCTTGGCATCGTTGGCAAGACGAGTACGG
GCGTAGTCCAGAGAGTAGACGAATAGAAGAGAAGTGGCACCAGCAGCACC
ACCGGAGGCAAGGTTACCGGCCATCCACATGGCGTAGCCATCCTTGTCCT
TCTTGTAACCGAACATCTTCTTGAACTTGTCACGGAAAGCGAAGTTCAGA
GCCTGGGTAGGGAAGTATCGGATGACGTTGGCGGTGTTTCCTCGCCAGAG
GGACATGACACCCTCATCGATCATTTGGAAGAAGGAGCAAGAGCAGTGAT
CTCCTTCTGCATACGGTCGGAGAGACCGGGGTACATGGTGGTACCACCAG
ACTAAAGACATGTTAGAACAGTTGGAGTGCTTTCGATTTGCAGAACTTAC
CATGACAATGTTTCCGTAGAGATCCTTTCGGACATCGACATCACACTTCA
TGATGGAGTTGAAAGTGGTGACGTGGATACCACCGCTCTCAAGACCAAGG
ACAGAAGGCTGGAAGAGAGCCTCAGGAGCACGGAATCGCTCGTTACCAAT
GGTGATAACCTGACCGTCAGGAAGCTCGTAAGACTTCTCCAAGCTGGAGC
TCTGGGCAGCAGTCTGGATCTCCTGCTCGAAAAATGCCCGCAGGCAATGT
GGGCAGTGTGGCAATCGAGGACGGGAGCGTAACCAGCACCGACCTGACCG
GGGTGGTTGAGGACGATGACCTGGGCGGTGAAAGAAGCGGCACCCATGGG
GGGGTCGTTCTTGGAGTCACCAGCGACGTTACCACGTCGGATGTCCTTGA
CGGAAACGTTCTTCACGTTGAAACCAACGTTGTCACCGGGCTGGCCCTCA
GTGAGCTGCTCGTGGTGCATCTCAACGGACTTGACTTCAGTGGTGACGTT
GGAAGGAGCGAAGGTAACGACCATACCGGGCTTGATGGAATTCTCTAGAC
CCAGCTTT
>Rho_GA-1_EF1 insert
GTACAAAAAAGCAGGCTTTAAAGGAACCAATTCAGTCGACCTCGAGCACC
TGCGCGGCCGCGAATTCGATTGCTTGTGGTAAAACCTGTTTGTTGATCGT
```

-continued
TTTCTCCAAGGGCACTTTCCCCGAGGTCTACGTCCCCACCGTCTTCGAGA
ACTATGTCGCCGATGTCGAGGTTGACGGCAAGCACGTCGAGCTCGCCCTA
TGGGATACTGCTGGTCAGGAGGATTACGACCGTCTTCGACCTCTCTCTTA
CCCCGACTCCCACGTTATCTTGATCTGCTTCGCTGTTGACTCTCCCGACT
CTCTCGACAACGTCCAGGAGAAGTGGATCTCTGAGGTTCTGCACTTCTGC
CAGGGKCTCCCTATCATCCTTGTCGGCTATCATTTGGAAGAAGGAGCAAG
AGCAGTGATCTCCTTCTGCATACGGTCGGAGAGACCGGGGTACATGGTGG
TACCACCAGACTAAAGACATGTTAGAACAGTTGGAGTGCTTTCGATTTGC
AGAACTTACCATGACAATGTTTCCGTAGAGATCCTTTCGGACATCGACAT
CACACTTCATGATGGAGTTGAAAGTGGTGACGTGGATACCACCGCTCTCA
AGACCAAGGACAGAAGGCTGGAAGAGAGCCTCAGGAGCACGGAATCGCTC
GTTACCAATGGTGATAACCTGACCGTCAGGAAGCTCGTAAGACTTCTCCA
AGCTGGAGCTCTGGGCAGCAGTCTGGATCTCCTGCTCGAAAATGCCCGCA
GGCAATGTGGGCAGTGTGGCAATCGAGGACGGGAGCGTAACCAGCACCGA
CCTGACCGGGGTGGTTGAGGACGATGACCTGGGCGGTGAAAGAAGCGGCA
CCCATGGGGGGGTCGTTCTTGGAGTCACCAGCGACGTTACCACGTCGGA
TGTCCTTGACGGAAACGTTCTTCACGTTGAAACCAACGTTGTCACCGGGC
TGTCCCTCAGTGAGCTGCTCGTGGTGCATCTCAACGGACTTGACTTCAGT
GGTGACGTTGGAAGGAGCGAAGGTAACGACCATACCGGGCTTGATGGGCG
AATTCTCTAGACCCAGCTTT >Rho_GA-1_mHspCh insert
GTACAAAAAAGCAGGCTTTAAAGGAACCAATTCAGTCGACCTCGAGCACC
TGCGCGGCCGCTAATTCGATCAGCCGACAAGGATGATAGGGAGACCCTGG
CAGAAGTGCAGAACCTCAGAGATCCACTTCTCCTGAACGTTGTCGAGGGA
GTCGGGAGAGTCAACGGCGAAGCAGATCAAGATAACGTGGGAGTCGGGGT
AAGAAAGAGGTCGAAGACGGTCGTAATCCTCCTGACCAGCAGTATCCCAT
AGGGCGAGCTCGACGTGCTTGCCGTCAACCTCGACATCGGCAACATAGTT
CTCGAAGACGGTGGGGACGTAAACCTCGGGAAAGTGCCCTTGGAGAAAAC
AATCAACAAACAGGTTTTACCACAAGCACCATCGATCATTTGGAAGAAGG
AGCAAGAGCAGTGATCTCCTTCTGCATACGGTCGGAGAGACCGGGGTACA
TGGTGGTACCACCAGACTAAAGACATGTTAGAACAGTTGGAGTGCTTTCG
ATTTGCAGAACTTACCATGACAATGTTTCCGTAGAGATCCTTTCGGACAT
CGACATCACACTTCATGATGGAGTTGAAAGTGGTGACGTGGATACCACCG
CTCTCAAGACCAAGGACAGAAGGCTGGAAGAGAGCCTCAGGAGCACGGAA
TCGCTCGTTACCAATGGTGATAACCTGACCGTCAGGAAGCTCGTAAGACT
TCTCCAAGCTGGAGCTCTGGGCAGCAGTCTGGATCTCCTGCTCGAAAAT
TGCCCTCGTAGACCTGGATAAGGACACCAGGCTGGGTGTCGGAGAAGGTA
GAGAAGACCTCGGACTTCTTGGTGGGAATGGTGGTGTTGCGGGGGATGAG
CTTGGTCATCATACCACCAGCGGTCTCGATACCGAGAGAGAGAGGGGCAA
CGTCGAGGAGCAGAATCTCGTTGGTGGTCTTGCTAGAGGTGTCACCAGAG
AGAATAGCAGCCTGGACAGCGGCACCGTAGGCAACAGCCTCATCAGGGTT -continued
GATGGACTTGTTGGGCTCCTTTCCGTTGAAGTAGTCGGTGATGAGCTTCT
GGGGGCGAATTCTCTAGACCCAGCTTT >Rho_AAC_EF1 insert
GTACAAAAAAGCAGGCTTTAAAGGAACCAATTCAGTCGACCTCGAGCACC
TGCGCGGCCGCTAATTCGATCGATGGTGCTTGTGGTAAAACCTGTTTGTT
GATTGTTTTCTCCAAGGGCACTTTCCCCGAGGTTTACGTCCCCACCGTCT
TCGAGAACTATGTTGCCGATGTCGAGGTTGACGGCAAGCACGTCGAGCTC
GCCCTATGGGATACTGCTGGTCAGGAGGATTACGACCGTCTTCGACCTCT
TTCTTACCCCGAATCTCAAGTTATCTTGATTTGCTTCGCCGTTGACTCTT
CCGACTCCCTCGACAACGTTCAGGAGAAGTGGATCTGTGAGGTTCTGCAC
TTCTGCCAGGGTCTCCCTATCATCCTTGTCGGCTGATCATTTTTGTAGAC
GTCGACGAGACCGTTGAACTGACGGTCACCACCGGACTTGGCGTTCTTGG
CATCGTTGGCAAGACGAGTACGGGCGTAGTCCAGAGAGTAGACGAATAGA
AGAGAAGTGGCACCAGCAGCACCACCGGAGGCAAGGTTACCGGCCATCCA
CATGGCGTAGCCATCCTTGTCCTTCTTGTAACCGAACATCTTCTTGAACT
TGTCACGGAAAGCGAAGTTCAGAGCCTGGGTAGGGAAGTATCGGATGACG
TTGGCGGTGTTTCCTCGCCAGAGGGACATGACACCCTCATAAATGCCCAT
CAAGCCCGGTATGGTCGTTACCTTCGCTCCTTCCAACGTCACCACTGAAG
TCAAGTCCGTTGAGATGCACCACGAGCAGCTCACTGAGGGCCAGCCCGGT
GACAACGTTGGTTTCAACGTGAAGAACGTTTCCGTCAAGGACATCCGACG
TGGTAACGTCGCTGGTGACTCCAAGAACGACCCCCCCATGGGTGCCGCTT
CTTTCACCGCCCAGGTCATCGTCCTCAACCACCCCGGTCAGGTCGGTGCT
GGTTACGCTCCCGTCCTCGATTGCCACACTGCCCACATTGCCTGGGCGA
ATTCTCTAGACCCAGCTTT Description of the Figures FIG. 1: Flow diagram for the high-throughput production of RNAi constructs. I, PCR amplification of cDNA fragments of fungal genes of interest; IIa, Ligation of the PCR fragments in the intermediate vector pIPKTA38 in the presence of the restriction endonuclease Swa I, which inhibits the re-ligation of the vector; IIb, Re-cutting of all re-ligated vector molecules; III, Recombination of the cloned cDNA fragments in the RNAi vector pIPKTA30 by means of LR clonase.

FIG. 2: Schematic representation of the synthesis pathway of simple (single) as well as combined (triple) RNAi constructs by means of the modified GATEWAY technology as to Douchkov et al. (2005) using the example of a sequence from gamma-actin (single RNAi construct), and a sequence combination of three components (gamma-actin, ADP/ATP carrier as well as RhoGTPase; triple RNAi construct). pIPKb007 (ubi), p6UGER4deltaSwaIntronRNAi (Ger4) and pIPKb010 (GSTA1) were used as binary RNAi destination vectors.

FIG. 3: Schematic representation of an alternative synthesis pathway of simple (single) and combined (triple) RNAi constructs by means of the modified GATEWAY technology as to Douchkov et al. (2005) using the example of a sequence from gamma-actin (single RNAi construct), and a sequence combination of three components (gamma-actin, ADP/ATP carrier as well as RhoGTPase; triple RNAi construct). pIPKb007 (ubi), p6UGER4deltaSwaIntronRNAi (Ger4) and pIPKb010 (GSTA1) were used as binary RNAi destination vectors.

FIG. 4: Flow diagram of the HIGS system. The RNAi constructs are directed against fungal transcripts.

FIG. 5: Transient transformation experiments with barley leaves of the sort Ingrid BC mlo5 (*Hordeum vulgare*). Spores of the phytopathogen *Blumeria graminis* f. sp. *hordei* (barley powdery mildrew) served as inoculum. In said system, single and triple target RNAi constructs were tested in combination with the vector pIPKb007.

FIGS. 6 to 11: Schematic representation of various triple siRNA vectors.

In the nucleotide sequences, the below-mentioned symbols were used for nucleic acids:

| Symbol | Meaning | Derivation of the designation |
|---|---|---|
| a | a | adenine |
| g | g | guanine |
| c | c | cytosine |
| t | t | thymine |
| u | u | uracil |
| r | g or a | purine |
| y | t/u or c | pyrimidine |
| m | a or c | amino |
| k | g or t/u | keto |
| s | g or c | strong bonds 3 H bridges |
| w | a or t/u | weak bonds 2 H bridges |
| b | b or c or t/u | not a |
| d | a or g or t/u | not c |
| h | a or c or t/u | not g |
| v | a or g or c | not t, not u |
| n | a or g or c or t/u, unknown or other | any |

SEQ ID NO: 1
FsCon[0026] AAC
>FsCon[0026]
TTTTCTCTCGACTCCCTCCATTCTCTCTTCCTTCTTTCATCCTCAATCTC
CCCTCAATCCTTTCTTCTTGTTCAAGGGAAAGACCATCACAGCCGCTACC
ATGTCTCCTCCTGCTGATCAAGGACCCCAGAAGGTCTTGGGCATGCCCCC
CTTCGTCGCTGACTTCCTCATGGGTGGTGTCTCCGCCGCTGTCTCCAAGA
CTGCTGCTGCCCCCATCGAGCGTGTCAAGCTCCTCATCCAGAACCAGGAT
GAGATGCTCAAGACCGGTCGTCTCGACCGCAAGTACAACGGCATTGGTG
ACTGCTTCAAGCGCACCATGGCCGATGAGGGTGTCATGTCCCTCGGCGA
GGAAACACCGCCAACGTCATCCGATACTTCCCCACCCAGGCCCTGAACTT
CGCTTTCCGTGACAAGTTCAAGAAGATGTTCGGCTACAAGAAGGACAAG
GATGGCTACGCCATGTGGATGGCTGGTAACCTTGCCTCCGGTGGTGCTGC
TGGTGCCACTTCTCTGCTCTTCGTCTACTCTCTGGACTACGCCCGTACTC
GTCTTGCCAACGATGCCAAGAACGCCAAGTCCGGTGGTGACCGTCAGTTC
AACGGTCTCGTCGACGTCTACAAGAAGACCCTCGCCTCTGACGGTATTGC
CGGTCTCTACCGTGGTTTCATGCCCTCCGTTGCTGGTATCGTTGTCTACC
GTGGTCTCTACTTCGGAATGTACGACTCCATCAAGCCCGTCGTCCTCACC
GGTAACCTCCAGGGCAACTTCCTTGC

SEQ ID NO: 2
GzCon[0015] EF1
>GzCon[0015]
CTGAGAAGCWMGTCGCACGAGGCCCGGCACGAGCATCCGATCTGCGAA
TCTCACGTTCATCACAAACGTACACACAAACCATCCACAACCGTCAAAAT
GGGTAAGGAGGAGAAGACTCACCTTAACGTCGTCGTCATCGGCCACGTC
GACTCTGGCAAGTCGACCACTACCGGTCACTTGATCTACCAGTGCGGTGG
TATCGACAAGCGAACCATCGAGAAGTTCGAGAAGGAAGCCGCCGAGCTC
GGTAAGGGTTCCTTCAAGTACGCCTGGGTTCTTGACAAGCTCAAAGCCGA
GCGTGAGCGTGGTATCACCATTGATATCGCCCTCTGGAAGTTCGAGACTC
CTCGCTACTATGTCACCGTCATTGACGCTCCCGGTCACCGTGATTTCATC
AAGAACATGATCACTGGTACTTCCCAGGCCGATTGCGCCATTCTCATCAT
TGCCGCCGGTACTGGTGAGTTCGAGGCTGGTATCTCCAAGGATGGCCAGA
CCCGTGAGCACGCTCTCCTTGCCTACACCCTTGGTGTCAAGAACCTCATT
GTTGCCATCAACAAGATGGACACCACCAAGTGGTCTGAGGCCCGTTACC
AGGAGATCATCAAGGAGACCTCTTCTTTCATCAAGAAGGTCGGCTACAAC
CCCAAGGCTGTCGCTTTCGTCCCCATCTCCGGTTTCAACGGTGACAACAT
GCTTACTGCCTCCACCAACTGCCCCTGGTACAAGGGTTGGGAGCGTGAGA
TCAAGTCTGGCAAGCTCTCCGGAAAGACCCTCCTTGAGGCCATTGACTCC
ATCGAGCCCCCAAGCGTCCCAACGACAAGCCCCTCCGACTTCCCCTCCA
GGATGTCTACAAGATTGGCGGTATTGGAACGGTTCCTGTCGGCCGTATCG
AGACTGGTATCATCAAGCCCGGTATGGTCGTTACCTTCGCTCCTTCCAAC
GTCACCACTGAAGTCAAGTCCGTTGAGATGCACCACGAGCAGCTCACTG
AGGGACAGCCCGGTGACAACGTTGGTTTCAACGTGAAGAACGTTTCCGTC
AAGGACATCCGACGTGGTAACGTCGCTGGTGACTCCAAGAACGACCCCC
CCCATGGGTGCCGCTTCTTTCACCGCCCAGGTCATCGTCCTCAACCACCC
CGGTCAGGTCGGTGCTGGTTACGCTCCCGTCCTCGATTGCCACACTGCCC
ACATTGCCTGCAAGTTCGCCGAGATCCAGGAGAAGATCGACCGCCGAAC
CGGTAAGGCTACTGAGGCCGCCCCCAAGTTCATCAAGTCTGGTGACTCCG
CCATCGTCAAGATGGTTCCCTCCAAGCCCATGTGTGTTGAGGCTTTCACC
GACTACCCTCCTCGGGTCGTTTCGCCGTCCGTGACATGCGACAGACCGT
CGCCGTCGGTGTCATCAAGGCCGTCGAGAAGTCCACTGGCGCTGCTGGCA
AGGTCACCAAGTCCGCTGCCAAGGCTGGTAAGAAATAAGCGCATTATTTC
TGAAATGACAACCTTCGGTGGGATCTTACGACTCTGGTCTCACGCCCAAG
GGCTGATGTACTCGCTTCTACGACGAAATGATCATGTTGGCATGAGCACT
CGGCTTATGTCTGGGGGCACGAGATGAGGCGAAAATAAAAGCCTGGGAT
CTTGTGCAAATCAAAAATAGGAATAGAGAGTCTAGAAGTGATTCGTGCA
AAAAAAAAAAAAAAAAAAAAAAAAAAAAAAAAAAAACTCGAGAAA
CTCGAGACTAGTTCTCTCTCTCCCTCGTGC

SEQ ID NO: 3
GzCon[0219] GA
>GzCon[0219]
GCTCTTCTTTTCCCGTAAGCTTGCTCCTCACTAATTCTAGCATCGCATCT
CATCACATTTGTCTTCTTTATACCACTTTGTCCTTTCTTTTTCTTCCTCG

-continued
CCTTGCAATCTTGGGCACGAGGCGTCTCTTCTTTTCCCCTTTCCCATACA
CACACCGTAATCCACAGCCATGGAGGAAGAAGTTGCTGCTCTCGTCATTG
ACAATGGTTCGGGTATGTGCAAGGCCGGTTTCGCCGGTGATGATGCTCCC
CGAGCTGTTTTCCCTTCCATTGTCGGTCGCCCCCGTCACCATGGTATCAT
GATCGGTATGGGTCAGAAGGACTCTTACGTTGGTGATGAGGCTCAGTCCA
AGCGTGGTATCCTCACACTGCGATACCCCATCGAGCACGGTGTTGTTACC
AACTGGGACGACATGGAGAAGATTTGGCACCACACCTTCTACAACGAGC
TGCGTGTCGCCCCCGAGGAGCACCCCGTCCTGCTCACCGAGGCTCCCATC
AACCCCAAGTCCAACCGTGAGAAGATGACCCAGATTGTCTTCGAGACCTT
CAACGCCCCCGCTTTCTACGTCTCTATCCAGGCCGTTCTGTCCCTGTACG
CCTCCGGTCGTACCACCGGTATCGTTCTGGACTCTGGTGATGGTGTCACT
CACGTTGTCCCCATTTACGAGGGTTTCGCCCTTCCCCACGCCATTGCCCG
TGTCGACATGGCTGGTCGTGATCTTACCGACTACCTCATGAAGATTCTTG
CTGAGCGCGGTTACACCTTCTCCACCACTGCCGAGCGAGAAATCGTCCGT
GACATCAAGGAGAAGCTCTGCTACGTCGCCCTTGACTTCGAGCAGGAGAT
CCAGACTGCTGCCCAGAGCTCCAGCTTGGAGAAGTCTTACGAGCTTCCTG
ACGGTCAGGTTATCACCATTGGTAACGAGCGATTCCGTGCTCCTGAGGCT
CTCTTCCAGCCTTCTGTCCTTGGTCTTGAGAGCGGTGGTATCCACGTCAC
CACTTTCAACTCCATCATGAAGTGTGATGTCGATGTCCGAAAGGATCTCT
ACGGAAACATTGTCATGTCTGGTGGTACCACCATGTACCCCGGTCTCTCC
GACCGTATGCAGAAGGAGATCACTGCTCTTGCTCCTTCTTCCATGAAGGT
CAAGATCATTGCTCCTCCCGAGCGAAAGTACTCCGTCTGGATCGGTGGTT
CCATTCTCGCTTCCCTGTCCACCTTCCAGCAAATGTGGATCTCCAAGCAG
GAGTACGACGAGAGCGGTCCTTCAATCGTTCACCGCAAGTGCTTCTAAGC
TACCCGACCGACAAATTAAATCCTCCCACTCGCCTAACGACAAGATCATG
GAGGTGGCGACAGACGCTAAGCTTTGGGTGGTTGGCCAACGTCAATGTCG
AATCTCGTATCTACGAAAAGTTTTTGACATGGTCGAAAGAGTGGGCGTTG
CGCTTGTTACGAAGAGATGTGATGGCCCCTTTTCTTGTAGTTCGCGTATA
ATGCGTGCCTAGGGGTAGAAGCCGAGGTTGACATACAAATACTTTTTAC
TTTCCGMWWARAAAAAAAAAAACTCGAGGG SEQ ID NO: 4
GzCon[2886] Hsp
>GzCon[2886]
GCACGAGGAGAGAGAGAGAGAACTAGTTTCGAGTTTTTTTTTTTTTTT
TTTTTTWTGAATGTATGATTCATTGATTCATTMAAGTACATARAYCACC
TTAGCTTTTCATAACCGTAAAGTCGCATAAAAACAGAAAAAAGGAAAAT
CTAATCTCATCATCCCATGAAAACGACTAGCCTCCGCATTATACCCATGG
ATATATGACCGCTCTAGAAGTCGAGACTGATGTTATTGGGGTATCAAGA
ATTTAGTCGACCTCCTCGACGGTGGGACCATCGTCACCACCGGCACGGG
GGCGGGGCCACCAGCACCAGGGAAGCCACCAGGGCCGCCGGGCATGCCG
GGCATGCCACCGGGAGCACCCTCACCACCAGCTCCGTAGAACTTCATCAT
GATGGGGTTAGCCTTGCCCTCGAGCTCCTTCTGGTGCTCCTCATACTCCT -continued
CACGAGTAGCCTGCTGGTTGTCATCGAGCCACTGGACGACCTTGTCAATC
TCAGCAGTGAGGGTCTCCTTGTCGGAAGCCTCAATCTTCTCCTCGACCTT
GGGGTCGGAGAGAGTGTTGCGGAGAGAGTAAGCGTAAGACTCAAGACCGT
TCTTGGCAGCGACACGCTTGCCCTCGGCCTCATCCTCCTCCTTGTACTTC
TCAGCATCGTTGAGCATGCGCTCGATCTCCTCCTTGGACAGGCGGCCCTT
GTCGTTGGTGATGACGATCTTGTTGGACTTGCCGGTACCCTTCTCGACGG
CGGAAACGTTCATGATACCGTTGGCATCGAGATCGAAGGTGACCTCAATC
TGGGGAACACCACGGGGAGCAGGGGGGATACCAGTGAGCTCGAACTTGCC
CATGAGGTTGTTGTCCTTGGTGCGCTGGCGCTCACCCTCGTAGACCTGGA
TAAGGACACCAGGCTGGTTGTCGGAGAAGGTAGAGAAGACCTCGGACTT
CTTGGTGGGAATGGTGGTGTTGCGGGGGATGAGCTTGGTCATCATACCAC
CAGCGGTCTCGATACCGAGAGAGAGGGGGGCGACGTCGAGGAGCAGAA
TCTCGTTGGTGGCCTTGCTAGAGGTGTCACCAGAGAGAATAGCAGCCTGG
ACAGCGGCACCGTAGGCAACAGCCTCATCAGGATTGATGGACTTGTTGG
GCTCCTTTCCGTTGAAGTAGTCGGTGATGAGCTTCTGGACACGGGGGATA
CGGGTAGATCCACCGACGAGGACGATCTCGTGGACGAGGGACTTGTCGA
TCTTGGCGTCGGTAAGGACACGGTCGACGGGCTGGATGGTGGATCGGAA
GAGATCCTGGCAGAGCTCCTCGAAACGAGCACGGGTGATGGAAGTGTAG
AAATCAATACCCTCGAAGAGAGTCGATCTCAATGGAGGTCTGAGCGG
AAGAAGAGAGAGTTCGCTTGGCGCGCTCACAAGCGGTTCGGAGACGTCG
AAGAGCACGGACGTTGGTGCTTAGATCCTTCTTATGCTTTCGCTTGAACT
CGTTAACGAAGTGGTTAACGAGGCGGTTGTCGAAATCTTCACCACCCAAG
TGAGTGTCACCGGCAGTAGACTTGACCTCGAAGATACCCTCCTCAATGGT
AAGGAGAGAGACATCGAAGSYWCSWSCRCCAAGATCGAAGATGAGGAC
GTTGCGCTCACCCTCAACCTTCTCCTCGTGC SEQ ID NO: 5
FsCon[0840] Rho
>FsCon[0840]
CCAAGCTCAACTCAAGCTCAAGCTCGCATTCTACGCCAGCAAATTCGTCC
ATTTCTCACAACTTCTTCACCCAAAAACACTTCTAATCAATAACCATGGC
TGAGATCCGCCGAAAGCTCGTCATTGTCGGCGATGGTGCTTGTGGTAAAA
CCTGTTTGTTGATCGTTTTCTCCAAGGGCACTTTCCCCGAGGTCTACGTC
CCCACCGTCTTCGAGAACTATGTCGCCGATGTCGAGGTTGACGGCAAGCA
CGTCGAGCTCGCCCTATGGGATACTGCTGGTCAGGAGGATTACGACCGTC
TTCGACCTCTCTCTTACCCCGACTCCACGTTATCTTGATCTGCTTCGCT
GTTGACTCTCCCGACTCTCTCGACAACGTCCAGGAGAAGTGGATCTCTGA
GGTTCTGCACTTCTGCCAGGGKCTCCCTATCATCCTTGTCGGCTGCAAGA
AGGATTTGCGATACGACC SEQ ID NO: 6
FsCon[0026] AAC Nt. 322-622
CGATGAGGGTGTCATGTCCCTCTGGCGAGGAAACACCGCCAACGTCATCC
GATACTTCCCCACCCAGGCCCTGAACTTCGCTTTCCGTGACAAGTTCAAG
AAGATGTTCGGCTACAAGAAGGACAAGGATGGCTACGCCATGTGGATGG SEQ ID NO: 7
GzCon[0015] EF1 Nt. 907-1204
ATCAAGCCCGGTATGGTCGTTACCTTCGCTCCTTCCAACGTCACCACTGA
AGTCAAGTCCGTTGAGATGCACCACGAGCAGCTCACTGAGGGACAGCCC
GGTGACAACGTTGGTTTCAACGTGAAGAACGTTTCCGTCAAGGACATCCG
ACGTGGTAACGTCGCTGGTGACTCCAAGAACGACCCCCCCCATGGGTGCC
GCTTCTTTCACCGCCCAGGTCATCGTCCTCAACCACCCCGGTCAGGTCGG
TGCTGGTTACGCTCCCGTCCTCGATTGCCACACTGCCCACATTGCCTGC SEQ ID NO: 8
GzCon[0219] GA Nt. 837-1141
TCGAGCAGGAGATCCAGACTGCTGCCCAGAGCTCCAGCTTGGAGAAGTC
TTACGAGCTTCCTGACGGTCAGGTTATCACCATTGGTAACGAGCGATTCC
GTGCTCCTGAGGCTCTCTTCCAGCCTTCTGTCCTTGGTCTTGAGAGCGGT
GGTATCCACGTCACCACTTTCAACTCCATCATGAAGTGTGATGTCGATGT
CCGAAAGGATCTCTACGGAAACATTGTCATGTCTGGTGGTACCACCATGT
ACCCCGGTCTCTCCGACCGTATGCAGAAGGAGATCACTGCTCTTGCTCCT
TCTTCC SEQ ID NO: 9
GA-1
TTCGAGCAGGAGATCCAGACTGCTGCCCAGAGCTCCAGCTTGGAGAAGT
CTTACGAGCTTCCTGACGGTCAGGTTATCACCATTGGTAACGAGCGATTC
CGTGCTCCTGAGGCTCTCTTCCAGCCTTCTGTCCTTGGTCTTGAGAGCGG
TGGTATCCACGTCACCACTTTCAACTCCATCATGAAGTGTGATGTCGATG
TCCGAAAGGATCTCTACGGAAACATTGTCATGGTAAGTTCTGCAAATCGA
AAGCACTCCAACTGTTCTAACATGTCTTTAGTCTGGTGGTACCACCATGT
ACCCCGGTCTCTCCGACCGTATGCAGAAGGAGATCACTGCTCTTGCTCCT
TCTTCCA SEQ ID NO: 10
GzCon[2886] Hsp Nt. 842-1197
ACTTGCCCATGAGGTTGTTGTCCTTGGTGCGCTGGCGCTCACCCTCGTAG
ACCTGGATAAGGACACCAGGCTGGTTGTCGGAGAAGGTAGAGAAGACCTC
GGACTTCTTGGTGGGAATGGTGGTGTTGCGGGGGATGAGCTTGGTCATCA
TACCACCAGCGGTCTCGATACCGAGAGAGAGGGGGCGACGTCGAGGAGC
AGAATCTCGTTGGTGGCCTTGCTAGAGGTGTCACCAGAGAGAATAGCAGC
CTGGACAGCGGCACCGTAGGCAACAGCCTCATCAGGATTGATGGACTTGT
TGGGCTCCTTTCCGTTGAAGTAGTCGGTGATGAGCTTCTGGACACGGGGG
ATACGG SEQ ID NO: 11
FsCon[0840] Rho Nt. 137-444
TGCTTGTGGTAAAACCTGTTTGTTGATCGTTTTCTCCAAGGGCACTTTCC
CCGAGGTCTACGTCCCCACCGTCTTCGAGAACTATGTCGCCGATGTCGAG
GTTGACGGCAAGCACGTCGAGCTCGCCCTATGGGATACTGCTGGTCAGGA
GGATTACGACCGTCTTCGACCTCTCTCTTACCCCGACTCCCACGTTATCT
TGATCTGCTTCGCTGTTGACTCTCCCGACTCTCTCGACAACGTCCAGGAG
AAGTGGATCTCTGAGGTTCTGCACTTCTGCCAGGGKCTCCCTATCATCCT
TGTCGGCT SEQ ID NO: 12
AAC consensus shortened
GCAGACCGTTCTTGGGCATGCCCCCCTTCGTCGCTGACTTCCTCATGGGT
GGTGTCTCCGCCGCTGTCTCCAAGACCGCTGCYGCCCCCATYGAGCGTGT
CAAGCTCCTCATCCAGAACCAGGATGAGATGCTGAAGACCGGTCGTCTY
GACCGCAAGTACGACGGCATTGGTGASTGCTTCAAGCGYACCACCGCSGA
TGAGGGTGTCATGTCCCTCTGGCGWGGHAACACTGCCAACGTCATCCGTT
ACTTCCCTACCCAGGCCCTGAACTTCGCTTTCCGTGACAAGYTCAAGTCG
ATGTTCGGCTACAAGAAGGACCGTGATGGCTACGCCATGTGGATGGCYG
GTAACYTKGCCTCCGGTGGTGCTGCTGGTGCCACTTCCCTCCTCTTCGTC
TACTCCCTCGACTACGCCCGTACYCGTCTTGCCAACGACGCCAAGAACGC
CAAGACCGGTGGTGACCGTCAGTTCAACGGTCTSGTCGATGTCTACAAGA
AGACCCTCGCCTCTGACGGTATTGCCGGTCTCTACCGTGGTTTCGGT:CC
TTCCGTTGCTGGTATCGTCGTYACCGTGGTCTCTACTTCG SEQ ID NO: 13
EF1 consensus shortened
ATGGGTAAAGGAGAAGACTCACATCAACGTCGTCGTCATCGGCCACGTC
GACTCCGGCAAGTCGACCACCACCGGTCACTTGATCTACAAGTGCGGTGG
TATCGACAAGCGTACCATCGAGAAGTTCGAGAAGGAAGCCGCCGAGCTC
GGYAAGGGTTCCTTCAAGTACGCCTGGGTTCTTGACAAGCTCAAGGCCGA
GCGTGAGCGTGGTATCACCATCGACATCGCCCTCTGGAAGTTCGAGACYC
CAAGTACTATGTTACCGTCATTGACGCCCCTGGTCACCGTGACTTCATC
AAGAACATGATCACTGGTACCTCCCAGGCCGACTGCGCCATTCTCATCAT
TGCCGCTGGTACTGGTGAGTTCGAGGCTGGTATCTCCAAGGATGGCCAGA
CTCGTGAGCACGCTCTCCTCGCCTACACCCTCGGTGTCAAGCAGCTCATC
GTYGCCATCAACAAGATGGACACCACCAAGTGGTCCGAGGACCGTTWCC
AGGAGATCATCAAGGAGACCTCCAACTTCATCAAGAAGGTCGGCTACAA
CCCCAAGACYGTCGCCTTCGTCCCCATCTCCGGTTTCAACGGTGACAACA
TGMTCGACGCCTCCACCAACTGCCCCTGGTACAAGGGTTGGGAGAAGGA
GACCAAGKCWGGCAAGGYCACCGGCAAGACCCTCCTCGAGGCCATCGA
CGCCATCGAGCCCCCCAAGCGTCCCACCGACAAGCCCCTCCGTCTTCCCC
TCCAGGATGTCTACAAGATCGGYGGTATTGGMACTGTTCCCGTCGGCCGT
RTCGAGACYGGTATCATCAAGCCCGGYATGGTCGTCACCTTCGCTCCCGC
CAACGTCACCACTGAAGTCAAGTCCGTCGAGATGCACCACGAGCAGCTC
ACTGAGGGTSTTCCCGGTGACAACGTCGGTTTCAACGTCAAGAACGTTTC
CGTCAAGGACATTCGCCGTGGTAACGTCGCTGGTGACTCCAAGAACGAC
CCCCCCAAGGGTGCCGCTTCCTTCAACGCYCAGGTCATYGTCCTYAACCA
CCCTGGTCAGGTCGGTGCTGGTTACGCCCCCGTTCTCGATTGCCACACTG
CCCACATTGCCTGCAAGTTCTCCGAGCTCCTCGAGAAGATCGACCGCCGT

ACCGGTAAGTCCATTGAGGACTCCCCCAAGTTCATCAAGTCTGGTGACGC

TGCCATCGTCAAGATGGTTCCCTCCAAGCCCATGTGTGTTGAGGCCTTCA

CYGACTACCCTCCTCTGGGMCGTTTCGCCGTCCGTGACATGCGTCAGACC

GTCGCTGTCGGTGTCATCAAGTCCGTCGACAAGTCCACGACACTGCCGGT

AAGGTCACCAAG

SEQ ID NO: 14
GA consensus shortened
ATGGAGGAAGAAGTCGCWGCTCTCGTCATYGACAATGGTTCGGGTATGT

GCAAGGCCGGTTTCGCCGGTGACGATGCTCCCCGAGCTGTCTTCCCTTCC

ATTGTCGGTCGCCCCCGTCACCATGGTATCATGATTGGTATGGGCCAGAA

GGACTCGTACGTTGGTGATGAGGCCCAGTCCAAGCGTGGTATCCTCACTC

TGCGGTACCCCATCGAGCACGGTGTYGTCACCAACTGGGACGACATGGA

GAAGATCTGGCACCACACCTTCTACAACGAGCTGCGTGTCGCCCCCGAGG

AGCACCCCGTCCTGCTGACTGAGGCTCCCATCAACCCCAAGTCCAACCGT

GAGAAGATGACGCAGATCGTCTTCGAGACCTTCAACGCCCCCGCCTTCTA

CGTCTCCATCCAGGCCGTKCTGTCCCTGTACGCCTCCGGTCGTACCACTG

GTATCGTGCTCGACTCYGGTGACGGTGTTACTCACGTTGTGCCCATCTAC

GAGGGTTTCKCCCTKCCCCACGCCATTGCCCGTGTCGACATGGCTGGTCG

TGACTTGACCGACTACCTGATGAAGATCTTGGCTGAGCGCGGTTACACCT

TCTCCACCACTGCCGAGCGWGAAATCGTCCGTGACATCAAGGAGAAGCT

CTGCTACGTCGCCCTTGACTTCGAGCAGGAGATCCAGACTGCTGCCCAGT

CCTCCAGCYTGGAGAAGTCCTACGAGCTTCCCGACGGACAGGTTATCACC

ATCGGCAACGAGCGCTTCCGTGCTCCTGAGGCTCTGTTCCAGCCTTCTGT

CCTGGGTCTTGAGAGCGGTGGTATCCACGTCACCACTTTCAACTCCATCA

TGAAGTGTGATGTCGATGTCCGAAAGGATCTGTACGGCAACATTGTCATG

TCTGGTGGTACCACCATGTACCCTGGTATCTCCGACCGTATGCAGAAGGA

GATCACTGCTCTTGCCCCKTCCTCSATGAAGGTCAAGATCATTGCTCCTC

CCGAGCGCAAGTACTCCGTCTGGATCGGTGGT:TCCATTCTC

SEQ ID NO: 15
Hsp consensus shortened
TCCACGAGATCGTCCTCGTYGGYGGWTCYACCCGTATCCCCCGTGTCCAG

AAGCTCATCACCGACTACTTCAACGGAAAGGAGCCCAACAAGTCCATCA

ACCCYGATGAGGCTGTTGCCTACGGTGCTGCCGTCCAGGCTGCCATTCTC

TCTGGTGACACCACCTCCAAGTCCACCAACGAGATCCTGCTYCTCGATGT

CGCCCCSCTSTCTCTCGGTATCGAGACCGCTGGTGGTATGATGACCAAGC

TCATCCCCCGCAACACCACCATCCCCACCAAGAAGTCYGAGGTCTTCTCC

ACCTTCTCCGACAACCAGCCTGGTGTGCTCATCCAGGTCTACGAGGGTGA

GCGCCAGCGCACCAAGGACAACAACCTSCTGGGCAAGTTCGAGCTTACC

GGCATCCCMCCTGCTCCCCGTGGTGTTCCCCAGATTGAGGTCACCTTCGA

CCTSGATGCCAACGGTATCATGAACGTCTCCGCCGTCGAGAAGGGCACCG

GCAAGACCAACAAGATTGTCATCACCAACGACAAGGGCCGYCTGTCCAA

GGAGGAGATYGAGCGCATGCTTGCYGAGGCCGAGAAGTACAAGGAGGA

GGATGA

SEQ ID NO: 16
Rho consensus shortened
AATCCATMACCATGGCTGAAATCCGCCGAAAGCTCGTCATTGTCGGHGA

YGGTGCTTGTGGTAAGACYTGTTTGTTGATTGTCTTCTCCAAGGGCACHT

TCCCMGAGGTCTACGTCCCMACCGTCTTCGAGAACTATGTCGCCGATGTC

GAGGTCGATGGCAAGCACGTCGAGCTCGCGCTATGGGATACBGCTGGTC

AGGAGGATTACGACCGTCTTCGACCTCTCTCATACCCCGACTCSCACGTT

ATCCTGATCTGCTTCGCCGTTGACTCTCCCGATTCCCTCGAYAACGTYCA

GGAGAAGTGGATCTCCGAGGTCCTSCAYTTCTGCCAGGGTCTCCCTATCA

TCCTTGTCGGCTGCAAGAAGGATTTGCGAYACGACCAGAAGACCATTGA

GGAGCTCCACAAGACCA

---

What is claimed is:

1. A method for creating broad-spectrum resistance to fungi in a transgenic plant, characterized in that a recombinant nucleic acid molecule comprising at least one nucleic acid sequence is introduced into the plant, wherein the at least one nucleic acid sequence is identical and/or complementary to the nucleic acid sequence according to SEQ ID NO 12, and/or a part thereof comprising at least 100 nucleotides, or has a sequence identity of at least 98% to the nucleic acid sequence according to SEQ ID NO: 12, and is transcribed in the plant, so that in case of an infection of the plant with a fungus, the nucleic acid sequence, or part thereof, interacts with one or more corresponding and/or complementary nucleic acids of the fungus, such that the expression of the fungal nucleic acid sequence is reduced by at least 80%, thereby creating broad-spectrum resistance to fungi in the transgenic plant, wherein the nucleic acid sequence comprises at least 100 nucleotides and wherein the nucleic acid sequence according to SED ID NO: 12 is the conserved region within the mitochondrial ADP/ATP translocator consensus sequence.

2. The method according to claim 1, wherein the recombinant nucleic acid molecule comprises:
   (a) a promoter functional in plants, and
   (b) operatively linked thereto the at least one nucleic acid sequence.

3. The method according to claim 1, wherein the recombinant nucleic acid molecule comprises:
   (a) a promoter functional in plants,
   (b) operatively linked thereto the at least one nucleic acid sequence,
   (c) an intron comprising a splice donor sequence and a splice acceptor sequence,
   (d) the nucleic acid sequence being reverse-complementary to the nucleic acid sequence mentioned in (b), and
   (e) a termination sequence.

4. The method according to claim 1, wherein the recombinant nucleic acid molecule comprises:
   (a) a promoter functional in plants,
   (b) operatively linked thereto the at least one nucleic acid sequence, wherein said sequence has reverse-complementary regions, and
   (c) a termination sequence.

5. The method according to claim 1, wherein the recombinant nucleic acid molecule comprises:
   (a) a promoter functional in plants,
   (b) operatively linked thereto the at least one nucleic acid sequence,
   (c) a second nucleic acid sequence encoding a ribonuclease P, and
   (d) a termination sequence.

6. The method according to claim 2, wherein the promoter is a constitutive promoter, an inducible promoter or a tissue-specific promoter.

7. The method according to claim 1, wherein the transgenic plant is a dicotyledonous or monocotyledonous plant.

8. The method according to claim 7, wherein the plant is a cereal plant.

9. The method according to claim 1, wherein the broad-spectrum resistance is against pathogenic fungi.

10. The method according to claim 3, wherein the promoter is a constitutive promoter, an inducible promoter or a tissue-specific promoter.

11. The method according to claim 4, wherein the promoter is a constitutive promoter, an inducible promoter or a tissue-specific promoter.

12. The method according to claim 5, wherein the promoter is a constitutive promoter, an inducible promoter or a tissue-specific promoter.

13. The method of claim 8 wherein the cereal plant is wheat or barley.

* * * * *